United States Patent [19]

Ben-Bassat et al.

[11] Patent Number: 5,268,274
[45] Date of Patent: Dec. 7, 1993

[54] METHODS AND NUCLEIC ACID SEQUENCES FOR THE EXPRESSION OF THE CELLULOSE SYNTHASE OPERON

[75] Inventors: Arie Ben-Bassat, Walnut Creek; Roger D. Calhoon, Concord; Anna L. Fear; David H. Gelfand, both of Oakland; James H. Meade, Pinole; Rony Tal, Richmond; Hing Wong, San Ramon, all of Calif.; Moshe Benziman, Jerusalem, Israel

[73] Assignee: Cetus Corporation, Emeryville, Calif.

[21] Appl. No.: 689,008

[22] Filed: Apr. 22, 1991

Related U.S. Application Data

[63] Continuation-in-part of Ser. No. 496,236, Mar. 23, 1990, abandoned, which is a continuation-in-part of Ser. No. 337,194, Apr. 12, 1989, abandoned.

[30] Foreign Application Priority Data

| Apr. 4, 1990 | [WO] | PCT Int'l Appl. | PCT/US90/01811 |
| Apr. 9, 1990 | [IL] | Israel | 94053 |
| Apr. 10, 1990 | [CA] | Canada | 2014264 |
| Apr. 11, 1990 | [IE] | Ireland | 1317/90 |
| Apr. 12, 1990 | [NZ] | New Zealand | 233312 |

[51] Int. Cl.$^5$ .................... C12N 15/00; C12N 15/54; C12N 15/74; C12P 19/04
[52] U.S. Cl. .................... 435/69.1; 435/101; 435/194; 435/252.3; 435/252.33; 435/320.1; 435/823; 536/23.2; 935/9; 935/14; 935/29; 935/40; 935/60; 935/72; 935/73
[58] Field of Search .............. 435/193, 194, 101, 69.1, 435/252.3, 252.33, 320.1; 530/350; 536/27

[56] References Cited

U.S. PATENT DOCUMENTS

| 4,942,128 | 9/1990 | Brown, Jr. et al. | 435/101 |
| 4,948,733 | 8/1990 | Easson, Jr. et al. | 435/172.3 |
| 4,950,597 | 8/1990 | Saxena et al. | 435/101 |
| 4,954,439 | 7/1990 | Brown, Jr. et al. | 435/101 |

FOREIGN PATENT DOCUMENTS

260093 3/1988 European Pat. Off. .

OTHER PUBLICATIONS

Ross, P., et al., 1987, Nature, 325:279-281.
Lin, F. C., et al., 1989, In Schuerch, C., Ed., *Cellulose and Wood-Chemistry and Technology*, pp. 473-492, John Wiley, N.Y.
Thelen, M. P., et al., 1986, Plant Physiology, 81:913-918.
Saxena, I. M., et al., 1990, Plant Molecular Biology, 15:673-683.
Saxena, I. M., et al., 1991, Plant Molecular Biology, 16:947-954.
Ross, P., et al., 1991, Microbiological Reviews, 55(1):35-58.
Lin, F. C., et al., 1990, The Journal of Biological Chemistry, 265(9):4782-4784.
Ullrich, A., et al., 1984, The EMBO Journal, 3(2):361-364.
Lin, et al., "Purification of Cellulose Synthase from *Acetobacter xylinum*, Symposium on the Biogenesis of Cellulose", The Tenth Cellulose Conference, May 29--Jun. 2, 1988, p. 27.
Bureau, et al., (1987), Proc. Natl. Acad. Sci. U.S.A., 84:6985-6989.
Thelen, et al., (1986), Chemical Abstracts, 105:295.
Aloni, et al., (1983), J. Biol. Chem., 258(7):4419-4423.
Fukaya, et al., (1989), Applied and Environmental Microbiology, 55(1):171-176.
Fukaya, et al., (1985), Agric. Bio. Chem., 49(7):2083-2097.

(List continued on next page.)

*Primary Examiner*—Robert A. Wax
*Assistant Examiner*—William W. Moore
*Attorney, Agent, or Firm*—Albert P. Halluin

[57] ABSTRACT

Nucleic acid sequences encoding the bacterial cellulose synthase operon derived from Acetobacter are disclosed. Methods for isolating the genes, vectors containing the genes, and transformed hosts useful for the expression of recombinant bacterial cellulose synthase or production of cellulose are also described.

53 Claims, 26 Drawing Sheets

OTHER PUBLICATIONS

Matthysse, et al., (1981), J. Bacteriol., 145:583-595.
Napoli, et al., (1985), Applied Microbiol., 30(1):123-131.
Canole-Parola, et al., (1964), Biochim. Biophys. Acta, 82:403-405.
Derwent Biotechnology Abstracts 85-04775, (1985), A Vector in Acetic Acid Bacteria, Beppu, JP 116149, published Jan. 18, 1985.
Derwent Biotechnology Abstracts 85-04756, (1985), Transformation of Acetic Acid Bacteria, Beppu, JP 116150, published Jan. 18, 1985.
Ross, et al., (1986), Carbohydrate Research, 149:101-117.
Fukaya, et al., (1985), Agric. Biol. Chem., 49(5):1349-1355.
Valla, et al., (1983), Arch. Microbiol., 134:9-11.
Okumura, et al., (1985), Agric. Biol. Chem., 49(4):1011-1017.
Valla, et al., (1985), Bacteriol., 165(1):336-339.
Inoue, et al., (1985), J. Ferment. Technol., 63(1):1-4.
Okumura, et al., Agric. Biol. Chem., 52(12):3125-3129.

```
  1  GGCTGGCCGCCCCGTGCCGACCGACAACTCCCGACCCTTGGTGGTCGGGCCACGACCGGTTGGTGCC                               90
 91  CAAGCCCAGCCTGCCGGATGCCCTGTTGCGCAAGCGTGAAGACGCGGACTCCTGAAACCGTGACCTGCTCCCGGC                      180
181  ATGTCAGAGAAAGAAGGGGAAGGTTTCCCCGCATCGCTGCGGGGCACATGACGAAGGCAGATGCGTCTGACGGTT                      270
          → Gene A
271  TTCTTTTGAATATATAACGACCTGTTTTACCAGTATTATTATCGACGAGCTATTGATGTCAGAGGTTCAGAGTTCAGTGCCAGTACCCGCGAG    360
         MetSerGluValGlnSerProValProAlaGlu
361  AGTAGGCTAGACCGCTTTCAACAAGATACTGTCACTGCTGGGGCCAACTATATAGTTGGAGCGCTTGTGCACTTATCGCC               450
         SerArgLeuAspArgPheSerAsnLysIleLeuThrAlaAsnTyrIleValGlyAlaLeuValLeuCysAlaLeuIleAla
451  GCAACCACGGTCACGCTGTCTCCATTAATGAGCAGCAGCTGATTGTGGCACTTGTGCTGTCTCGTCTTTTTATTGTCGGGCGCAAGAGC        540
         AlaThrThrValThrLeuSerIleAsnGluGlnLeuIleLeuValAlaLeuValPhePheIleValGlyArgGlyLysSer
541  CGCCGCACCCAGATCTTTCTCGAGGTGCTCCTCGGCTGTCCTCGGTTACCTGACCATGGCCCTGACCGAAACGTTGACTTCGAT              630
         ArgArgThrGlnIlePheLeuGluValLeuLeuGlyCysLeuValSerAlaLeuValSerLeuArgTyrLeuThrArgGluThrLeuAspPheAsp
631  ACATGGATTCAGGGCGCGGCTGGGCGTGACCCTGCTCATGGCCGAACTCTATGCCCTGTACATGCTGTTCTCAGCTATTCCAGACAATC        720
         ThrTrpIleGlnGlyAlaGlyValThrLeuLeuMetAlaGluLeuTyrAlaLeuTyrMetLeuPheSerTyrPheGlnThrIle
721  CAGCCACTTCATCGCCGACCTCCGCCGGACAATGTTGATGACGTGGCCAACCGTGACATCTTCATCCCGACCTATGATGAACAG           810
         GlnProLeuHisArgArgThrSerAlaProLeuProAspAsnValAspAspTrpProThrValAspIlePheIleProThrTyrAspGluGln
811  CTCAGATCGTGCCCTGACCGTGCTGGGCGCCTGACTGGCCCCGATAAAGTGAATGTCTATATCCTTGATGATGGTGTG                   900
         LeuSerIleValArgLeuThrValLeuGlyIleAlaLeuGlyIleAspTrpProProAspLysValAsnValTyrIleLeuAspAspGlyVal
901  CGCCCCGAATTTGAACAGTTGCCAAGGATTGCCACACGCCGTCGACAGTTCACACGCCAAGGCCGGGTAACCTCAAC                    990
         ArgProGluPheGluGlnPheAlaLysAspCysGlyAlaLeuTyrIleGlyArgValAspSerSerHisAlaAlaGlyAsnLeuAsn
991  CACGGCCATTAAGCGGACAAGCGGCGATTACATCCTCATCCTGATTGTGACCATATTCCGACACCGCCGTTCCTGCAGATCGCGATGGGC     1080
         HisAlaIleLysArgThrSerGlyAspTyrIleLeuIleLeuAspCysAspHisIleProThrArgAlaPheLeuGlnIleIleAlaMetGly
```

FIG. 1A

```
1081  TGGATGGTCGCAGACCGCAAGATCGCCCTGATGCAGAGCGCCGCATCACTTCTACTCCCCGATCCGTTCCAGCGTAACTTGGCCGTGGGG   1170
      TrpMetValAlaAspArgLysIleAlaLeuMetGlnThrProHisPheTyrSerProAspProPheGlnArgAsnLeuAlaValGly

1171  TATCGCACCCCGCGGAAGGCAACCTGTTCTACGGCGTCATTCAGGATGGTAACGACTTCTGGGATGCCACCTTCTCTGCGGCTCGTGC   1260
      TyrArgThrProProGluGlyGlnLeuPheTyrGlyValIleGlnAspGlyAsnAspPheTrpAspAlaThrPhePheCysGlySerCys

1261  GCCATCCTCGCCGGTGAAGCCATTGAATCGATCGGCCGTTCGCCGGTTGAAACCGTGACGAAGATGCCATACCGCCTGCATGCAG   1350
      AlaIleLeuAlaGlyGluAlaIleGluSerIleGlyArgSerProValGluThrValThrGluAspAlaHisThrAlaLeuArgMetGln

1351  CGCCGTGGCTGTCCACCGCCTACCTGGCCAGTGGACTGGCCACCGAGGACTGACAACCCATATCGGCCAGCGCATG   1440
      ArgArgGlyTrpSerThrAlaTyrLeuAlaSerGlyLeuAlaThrGluArgLeuThrThrHisIleGlyGlnArgMet

1441  CGCTGGGCACGCGGCATGATCCAGATCTTCCGCGTGGACAAACCCGTGAAGCTTGGGCAGCGGCTGTGCTATCTC   1530
      ArgTrpAlaArgGlyMetIleGlnIlePheArgValAspAsnProValLysLeuGlyLeuArgLeuCysTyrLeu

1531  TCGGCCATGACGTCGTCTCTTCTCCGCCGTCATCTCTCCTGTTTTCGGCCAGAACATCATC   1620
      SerAlaMetThrSerPhePheAlaIleProArgValIleProLeuAlaSerProLeuPheLeuPheProGlyGlnAsnIleIle

1621  GCCGCCTCGCCCTGGCCTGCTACGAACGCCATTCCGCACATGTTCCACTCCATCGCGACCCGCAAGGTGAACAAGGGCGGC   1710
      AlaAlaSerProLeuAlaValLeuAlaTyrAlaIleProHisMetPheHisSerIleAlaThrAlaAlaLysValAsnLysGlyTrpArg

1711  TATTCGTTCTGGAGTGAAGTGTACGAAACCACCATGGCGCTGTTCCTGGTGCGGTAACCCTGATGTTCCCCTCCAAGGGC   1800
      TyrSerPheTrpSerGluValTyrGluThrThrMetAlaLeuPheLeuValArgValThrIleIleThrLeuMetPheProSerLysGly

1801  AAGTTCAACGTGACGGAAAAGGTGGCCGTGCTGAGAGGAAGAGTTCGACCTTGGCGCCACCTACCCCCAACATCATTTGCCGGCATC   1890
      LysPheAsnValThrGluLysValAlaValLeuLeuGlyValLeuGluGluValPheAspLeuGlyAlaThrTyrProAsnIleIlePheAlaGlyIle

1891  ATGACGTTGGGCTGCTGTCTGATCGTGCTCGTGTTGAACTGACCTTCCACTCCAACAGTCGCCAAGGTGCATTGCCAAGCTGCTACCTGCTGAAC   1980
      MetThrLeuGlyLeuLeuIleGlyLeuPheGluLeuPheHisPheAsnGlnLeuAlaGlyIleAlaLysArgAlaTyrLeuLeuAsn

1981  TGCATCTGGGCGATGATCAGTCATCATCCTCCTTGCCGCATTGCCGTGGGCGTGAGACCAAGCAGTCCGTTACAACCATCGTC   2070
      CysIleTrpAlaMetIleSerLeuIleIleLeuLeuAlaAlaIleAlaValGlyArgGluThrLysGlnValArgTyrAsnHisArgVal
```

```
5041  CTGCTGGCCAGCAGTTGCATGACGGTGCTGTGGCGGTTCCTGTTGCCGGGCCAGCAGGCTTCACCGCCATGACCACCGCTGCCACG  5130
      LeuLeuAlaSerSerCysMetThrValLeuValAlaValProValAlaArgAlaGlnGlnAlaSerThrThrAlaMetThrThrAlaAlaThr

5131  AGGCGACTGCGGCACCACGGCCAGATCCTGTTGCAGCAGGCACGCTTCGGCTTGCAGCACCAGCAGTATGACAATGCCGCCAGGCCTTG  5220
      SerAlaThrAlaAlaProArgGlnIleLeuLeuGlnLeuGlnAlaArgPheTrpLeuGlnGlnGlnTyrAspAsnAlaArgGlnAlaLeu

5221  CAGAACGCGGAGCGCATCGCCCCCAATTCCCCTGACGTGCTGGTGAAGTGCTGGTGAATACCAGACGGCCATTGCAACCCGAAGCCGCC  5310
      GlnAsnAlaGluArgIleAlaProAsnSerProAspValLeuValLeuGluValLeuGluTyrGlnThrAlaIleGlyAsnArgGluAlaAla

5311  GCCGATACGCTGCCGCCACCTGCAGCAGGTGCCCGGGCCAGTGCCCGGTAACCTGAATGACCTGCTCAGGAGGCGAGCGGGCCATCTCC  5400
      AlaAspThrLeuArgHisLeuGlnValAlaProGlySerAlaAlaAlaGlyAsnLeuAsnAspLeuLeuSerGluArgAlaIleSer

5401  CAAAGGCGACCTGTCGCAGATCCGCTGGCCGGGTTCGGCCAGAACGCAGGAGTTCGGGCCAGAACGCCAGATCGCTGCGACAGGGCCATCTCCAGGAGCGCCATCTCC  5490
      GlnSerAspLeuSerGlnIleArgSerLeuAlaGlySerGlyGlnAsnAlaGlnAlaValAlaGlyTyrGlnLysLeuPheHisGlyGly

5491  AAGCCGCGCATTCGCTGCGGGTGGAATACTACCAGACCATGGCCGGCCTGCTGGACCAGGCCCGGCCCGGGCTTGCCGGG  5580
      LysProProHisSerLeuAlaValGluTyrTyrGlnThrMetAlaGlyValProAlaGlnTrpAspGlnAlaArgAlaGlyLeuAlaGly

5581  GTCGTTGCGTCAAACCCGCAGATTACCGCCAGCCCTGCGCCTTGCCAGGCCCTGCACCTATAATACCTGACCTATAATACCTGACCTATAATACCTGACCCCATGGAAGGCTG  5670
      ValValAlaSerAsnProGlnIleThrAlaSerProCysProLeuAlaGlnLeuAlaPheAlaAlaLeuThrTyrAsnThrSerThrArgMetGluGlyLeu

5671  ACCCGGCTCAAGGATCTCCAGTCCTTCCGCAGCCAGGCCCGGTCGAGGGCGTCAGCCCGGTCGAGGGCGTCAGCAGCCGTGCCAGCCCTGAGCTGG  5760
      ThrArgLeuLysAspLeuGlnSerPheArgSerGlnAlaProValGluAlaAlaAlaAlaGlnSerTyrArgGlnThrLeuSerTrp

5761  CTGCCGGTCAATCCTGAGACGCAGCCCTCATGGAGACCAGTGGCTTTCCGCCACCCAATGATACCGCTGCCGAGCATATGCTCCAC  5850
      LeuProValAsnProGluThrGlnProLeuMetGluGlnTrpLeuSerAlaHisProAsnAspThrAlaLeuArgGluHisMetLeuHis

5851  CCCCCCGGTGGTCCGCCGGACAAGGCCCGGCTTGCCGCCGACAAGGCCGGGCCGGTCGACAAGGCTTGCCGGCGTTAACCGGACGAGACAG  5940
      ProProGlyGlyProProAspLysAlaGlyLeuAlaArgGlnLeuAsnAlaGlyTyrGlnLeuAsnAlaAlaArgLeuAlaAlaAlaGluGln

5941  TCTTTCCAGTTGCGTTGCAGATCAATTCCATGATGCTGATTCGCTTGGTGCTGCTGATGTGCTGTGCTCGTAAGCATGGGCTCGTAAGCATGGGCTCGTAAGCATGGGTCATGGGCCAGGGCGATACCGCG  6030
      SerPheGlnSerAlaLeuGlnIleAsnSerHisAspAlaAspSerLeuValSerMetArgGlyMetGlyMetGlyLeuValSerMetArgGlnGlyAspThrAla
```

FIG. 1G

```
6031  GAGGGCGCCGCTATTTGAAGAAGCGATGGCCGCGATCGCTGGCCGCCCGCTTGCGGGCATGGCCGTCAGC                    6120
      GluAlaArgArgTyrPheGluGlyAlaMetAlaAlaAspArgProLysThrAlaAlaAspArgTrpArgProAlaLeuAlaGlyMetAlaValSer

6121  GGCGAGTATGCTTCCGTTCGCCAGTTGATTGCCGCCATCAATATACCGAGGCAGGCCAAGCAGCTTGCCACGCTGGCCCAGCCCGGC        6210
      GlyGluTyrAlaSerValArgGlnLeuIleAlaAlaHisGlnTyrThrGluAlaLysGlnLeuAlaThrLeuAlaArgGlnProGly

6211  CAGTATACTGGCGCGACCCTCATGCTGGCCGCTGCCGACCTCGCCAGCGGTCGCCGCCGAGCAGGAGATATCTGGCATCCTG            6300
      GlnTyrThrGlyAlaThrLeuMetLeuAlaAlaAspLeuAlaSerGlyArgSerThrGlyGlnIleAlaAlaAlaGluGlyGlnTyrArgGlyIleLeu

6301  TCGCGTGAGCCAATAACCAGTTGGCCTCATGGGCCTGGCCGGGTAGACATGGCCAGGGCAACACGGGAAGCAACGGCCAGCTCCTG        6390
      SerArgGluProAsnAsnGlnLeuAlaLeuMetGlyLeuAlaArgValAlaAspMetAlaGlyAsnThrAlaGlnAlaArgGlnLeuLeu

6391  TCGCGTGTCGGCCCCAATATGCAAGCCAGTGGGCGAGATCGAGTTTCGGGCCTGATGGCGCTCCCAGACATCGATTCAGCG             6480
      SerArgValGlyProGlnTyrAlaSerGlnValGlyLeuIleGluValSerGlyLeuMetAlaAlaAlaSerGlnThrSerAspSerAla

6481  CGCAAGGTTTCCATCCTGCGCGAAGCGATGGCCCAGGCCCACGTGACCCCTGGGTGGCGCATCAACCTTGCCAATGCGCTGCAGCAGCAG    6570
      ArgLysValSerIleLeuArgGluAlaMetAlaGlnAlaProArgAspProTrpValArgIleAsnLeuAlaAsnAlaLeuGlnGlnGln

6751  GAAATGGAAATCAAGCAGGATCTGGCCAGCGATCTGAGCCGTGTCCCGTGCCGTGATCCGGAGGCCCTGATCCGGAGGCCCTGATG        6840
      GluMetGluIleLysGlnAspLeuAlaSerArgLeuSerMetValSerArgAsnProValProLeuIleArgGluAlaLeuThrGlnProAsp

6841  CCGACCGGCGGCGGGGTGGCTGACCTGTTCCGCCAGCGGTGCGACATGGTGAGCCTCTTCGCCAGCGGTGGCGACATGGTGAGCCTCG      6930
      ProThrGlyAlaArgGlyValAlaValAlaAlaAspLeuPheArgGlnArgGlyAspMetValHisAlaArgMetAlaLeuArgIleAlaSer

6931  ACGCGCCACCATCGATCTCTCGCCCAGCCGCTCTGTCCTATGCCACCGAATACATGAAGATCAGCAGCAATACATGAAGATCAGCAGGC     7020
      ThrArgThrIleAspLeuSerProAspGlnArgLeuSerTyrAlaThrGluTyrMetLysIleSerAsnProValAlaAlaAlaArgLeu

7021  CTGCCCCCGTGGGGATGCCACGGCTCGGCTACAGGAAGCCGTTGTCTGCCCAGCAGGTGCAGACCGCTCCAGACTGCCATGGGC          7110
      LeuAlaProLeuGlyAspGlyThrGlySerAlaThrGlySerAlaLeuLeuProGluGlnValGlnThrLeuGlnLeuArgMetGly

7111  ATCTCGGTGCGCAGTCGTCGATCCTCAACCAGGCTGGCGACCAGGCCTATGATCATCTGGCCCCCGCTGCAGGCCGACCCG             7200
      IleSerValAlaGlnSerAspLeuLeuAsnGlnSerAspLeuLeuAsnGlnAlaArgGlyAspGlnAlaGlnAlaTyrAspHisLeuAlaProAlaLeuGlnAlaAspPro
```

FIG. 1H

```
7201  GAGGGACATCGCCCAAGCTGGCCTCGCGCGGCTGTATAATGGCCACGGCAAGCCGGGAGATCGACCTTGCGGTGCTG              7290
      GluAlaThrSerProLysLeuAlaLeuAlaArgLeuTyrAsnGlyHisGlyLysProGlyLysAlaLeuGluIleAspLeuAlaValLeu

7291  CGCCACAACCCGCAGGACCTTGATGCGCCGGACACAGCTCGCGGTCAACAGCGACCACAGCCTTGCCACCCGCCTTGCC              7380
      ArgHisAsnProGlnAspLeuAspAlaProAspThrAlaArgGlyGlnGlnAlaAlaValAlaAlaAsnSerLeuAlaThrArgLeuAla

7381  ATGGATGGCGTGCAGGAAAGCCCGATGGATGCCGCTGGCCATGGCCCGTGACCAGGGCCACGGCCAGGCACC              7470
      MetAspGlyValGlnGluSerProMetAspAlaArgAlaTrpLeuAlaMetAlaValAlaAspGlnAlaAspGlyHisGlyArgThr

7471  ATCGAGGATCTGCGCCGCCTATGACCTGCGCCTCGAGGTGCAGGGCACGCGGTCTGGCGGGTGCTGCGCAGGAAGAT              7560
      IleGluAspLeuArgArgAlaTyrAspLeuArgArgLeuGlnValGluGlyThrArgAlaAlaSerGlyAlaAlaGlyAlaAlaGlnGluAsp

7561  GCGCTTGCTCCGCCCTCGACACCCGTTCCCCCCGCTACGGCCACCAGACGAACTTGGCGCCCTGTGACCGGTGGCTCCTAC              7650
      AlaLeuAlaProProSerThrProPheArgGlyTyrGlyHisGlnThrGluLeuGlyHisGlnThrProValThrGlyGlySerTyr

7651  AGCGCCGAGGCGCATCGCCCGATACGTCGGACCAGATGTCTCCTCCATCCAGGCCAGATCGCTGAGAACCTTGCCCT              7740
      SerAlaGluAlaAlaSerProAspThrSerAspGlnMetLeuSerSerIleAlaGlyGlnIleArgThrLeuArgGluAsnLeuAlaPro

7741  TCCATCGATGGTGGCCTCGGGTTCCGCTTCGGGTGAGCATGGCGGTTCGGGTGAGGCGAATGGGCGCCTGACGGAAGCGAACATTCCATCCATCGGGCCGC              7830
      SerIleAspGlyTrpGlyLeuGlyLeuGlyPheArgSerArgSerGlyGluHisGlyMetGlyArgLeuThrGluAlaAsnIleProIleValGlyArg

7831  CTGCCGCAGGCCGGTGCTCCCGCCTTCCCGCCCTCGATCACGCCAACCATGATCTGTTCGGGCAACCTCAACACGGGTTCCGTCTAT              7920
      LeuProLeuGlnAlaGlyAlaSerAlaLeuThrPheSerIleThrProThrMetIleTrpProThrMetIleTrpSerGlyAsnLeuAsnThrGlySerValTyr

7921  GATGTGCCGGTTATGGCACGATGATGGCACGATGATGGTGGCGGTTATACCAACCGGGACCAGGAGGACCAGGACCAGCAGCGCATC              8010
      AspValProArgTyrGlyThrMetMetGlyValGlnAlaThrTyrAsnGlnAlaThrTyrAsnAlaGlyArgArgAspGlnArgIle

8011  GCCGCTGGCACGGCCGAGGCCGGTTTGCCGCCGATGTGCAGTTTGGCAATAGTGCAGTTTGGCAATGTGCAGTGGCCTTGGCCGATGTGGGTCGCCCATCGGC              8100
      AlaAlaGlyThrAlaGlyGluAlaGlyPheAlaAlaProAspValGlnPheGlyAsnSerTrpValArgAlaAspValGlyAlaSerProIleGly

8101  TTCCCCATCACCAACGTGCTGGGCGGTGTCGAGTTCCGGTCCGTCACCTTCCGTCAGTGCCAGCGCCGTGCAGGGCCGTGATC              8190
      PheProIleThrAsnValLeuGlyGlyValGluPheArgValGluPheSerProArgValGlyProValThrPheArgValSerAlaGluArgArgSerIle
```

POLYLINKER CLONING SITES OF PUC 19
(396-447)

Hind III
Xma I

METHODS AND NUCLEIC ACID SEQUENCES FOR THE EXPRESSION OF THE CELLULOSE SYNTHASE OPERON

CROSS REFERENCE TO RELATED APPLICATION

This is a continuation-in-part application of U.S. Ser. No. 496,236 filed Mar. 23, 1990, now abandoned, which is a continuation-in-part application of U.S. Ser. No. 337,194 filed Apr. 12, 1989, now abandoned. The disclosures of each application are incorporated herein by reference.

TECHNICAL FIELD OF THE INVENTION

The invention relates to the field of recombinant DNA techniques for the production of proteins. More specifically, this invention relates to the cloning of the bacterial cellulose synthase operon, the expression and regulation of this operon and methods of using this operon for production of cellulose in recombinant microorganisms.

BACKGROUND OF THE INVENTION

Cellulose is relied upon as the raw material for a number of useful products including paper products and wound dressings. Cellulose may be obtained from plants and various microorganisms in culture, for example from the cellulose producing bacteria of the genus Acetobacter. Acetobacter is characteristically a Gram-negative, rod-shaped bacterium 0.6-0.8 um by 1.0-4 um. It is strictly aerobic; metabolism is respiratory, never fermentative. It is further distinguished by the ability to produce multiple poly $\beta$(1-4)-glucan chains, chemically identical to cellulose. Multiple cellulose chains or microfibrils are synthesized at the bacterial surface at sites on the cell wall. The production of cellulose by Acetobacter has been the subject of intense study since at least the 1930's. In particular, Acetobacter xylinum has been widely studied to attempt to elucidate the mechanism of cellulose synthesis in intact cells [Schramm and Hestrin,(1954) *J. Gen. Microbiol.* 11:123-129].

The enzymatic pathway for cellulose synthesis in Acetobacter xylinum has been investigated and essentially four enzymatic steps have been characterized in cell free extracts of *A. xylinum* which appear to comprise the complete pathway from glucose to cellulose. These are the phosphorylation of glucose by glucokinase [Benziman, et al., (1972) *J. Bacteriol.*, 111:325-330], the isomerization of glucose-6-phosphate to glucose 1-phosphate by phosphoglucomutase [Gromet. et al.. (1957) *Biochem. J.*, 67:679-689; Frei-Roitman, Factors affecting the activity of phosphoglucomutase and UDP-glucose pyrophosphorylase of *Acetobacter xylinum*, M.Sc. thesis, The Hebrew University of Jerusalem, Jerusalem, Israel (1974)]; the synthesis of uridine 5'-diphosphoglucose (UDP-glc) by UDPG-pyrophosphorylase, [Frei Roitman, supra; Swissa, Biosynthesis of cellulose in *Acetobacter xylinum*, Ph.D. thesis, The Hebrew University of Jerusalem, Jerusalem, Israel (1978)], and the cellulose synthase reaction.

Attempts to purify cellulose synthase from a strain of *A. xylinum* employing conventional chromatographic techniques have not been especially successful, but recently the enzyme has been significantly purified (P. Ross and M. Benziman (1989) in Biosynthesis and Biodegradation of Cellulose and Cellulose Materials, eds. Weimar and Higler, Marcel Dekker, Inc. NY), and its properties and structure in the purified state are currently under investigation.

Similarly, attempts to purify cellulose synthase by in vitro cellulose entrapment and chromatographic techniques have resulted in a partially purified 83 kilodalton (kd) polypeptide (Lin and Brown, The Tenth Cellulose Conference, May 29-Jun. 2, 1988, Abstract BG1, page 27).

Although the physiological role of cellulose synthesis in this organism is still not clear, considering that at least 10% of the cell's energy budget is devoted to cellulose production at any one time [Weinhouse, Regulation of Carbohydrate metabolism in *Acetobacter xylinum*, Ph.D. thesis, The Hebrew University of Jerusalem, Jerusalem, Israel (1977)], it is not surprising that the biosynthetic system is governed by a complex regulatory system.

Cellulose synthase, the only enzyme unique to the pathway, performs the "committed" step in cellulose formation—a metabolic dead-end with regard to carbon utilization—and hence would logically be the prime candidate for strict regulatory control. Furthermore, as demonstrated in cell-free extracts, the level of enzyme activities leading to UDP-glc are in large excess relative to that of the cellulose synthase, strongly supporting the proposition that the latter comprises the rate limiting step in cellulose biosynthesis.

A more complete knowledge of the biochemistry of cellulose synthesis would facilitate greater productivity and yield of cellulose from cultures of cellulose producing microorganisms. The growth of bacterial cells in culture is observed to be initially exponential but slows as the cells enter a stationary growth phase. The majority of cellulose is produced later in fermentation when the number of cells is highest, however the amount of cellulose made per cell per unit time (specific productivity) declines as the fermentation proceeds. It is believed that cellulose synthase activity may be rate limiting as cells in culture reach the stationary growth phase. One improvement in cellulose production would be to remove a rate limiting step in cellulose synthesis, thereby preventing the observed decline in cellulose specific productivity in culture.

Recombinant DNA techniques are now routinely available for production of desired proteins. However, to take advantage of such recombinant DNA techniques, the gene coding for the desired protein, such as cellulose synthase, must first be isolated. This task is considerable, especially when the primary sequence of the encoded protein is unknown and known assays for determining cellulose synthase activity are difficult.

The ability to produce recombinant cellulose synthase provides an important tool useful in exploring the mechanisms of cellulose synthesis, ultimately providing enhanced cellulose production from bacterial culture.

SUMMARY OF THE INVENTION

The present invention provides an operon associated with the biosynthesis of cellulose, polynucleotides encoding one or more closely linked genes that code for proteins of bacterial cellulose synthase, expression vectors suitable for production of cellulose synthase recombinant host cells transformed with these vectors, methods for producing bacterial cellulose synthase, methods for regulating the production of cellulose and methods to increase the production of cellulose in a recombinant microorganism.

More particularly the invention provides an isolated native, cloned recombinant or synthetic polynucleotide encoding the bacterial cellulose synthase operon characterized by the polycistronic nucleotide sequence shown in FIG. 1 (SEQ ID No: 1). The cellulose synthase operon is approximately 9217 basepairs (bp) in length and comprises four genes, designated herein as "A" (SEQ ID No: 3), "B" (SEQ ID No: 4), "C" (SEQ ID No: 5), and "D" (SEQ ID No: 6).

The invention further provides a process for expressing cellulose synthase in a host cell comprising transforming the host cell with a recombinant DNA expression vector comprising one or more of the genes associated with the bacterial cellulose synthase operon, which gene(s) is operably linked to a control sequence for expression of bacterial cellulose synthase, and culturing the transformed host cell under conditions suitable for expression of cellulose synthase.

The expression vector constructions of the present invention can either replicate independently or may be designed so as to introduce a heterologous promoter into the Acetobacter chromosome, thereby replacing the native cellulose synthase operon promoter.

Yet another aspect of the invention provides a method for increasing cellulose production in a recombinant microorganism, which method comprises transforming a suitable microorganism with a vector comprising at least one gene derived from the cellulose synthase operon, and culturing the transformed microorganism under conditions suitable for production of cellulose. As discussed above, the chromosomal cellulose synthase promoter can be replaced with a heterologous promoter to overexpress the cellulose synthase operon at the chromosomal level. This heterologous promoter may be a regulated promoter.

A further aspect of the invention provides the individual proteins encoded by the cellulose synthase operon. The recombinant cellulose synthase B protein in association with the recombinant cellulose synthase A protein is capable of synthesizing $\beta(1-4)$-glucan polymers from uridine 5'-diphosphoglucose. The protein encoded by gene A is capable of complementing cellulose negative Acetobacter cells defective in both cellulose synthase and diguanylate cyclase activities. The protein encoded by either gene C or D is capable of synthesizing $\beta(1-4)$-glucan polymers from uridine 5'-diphosphoglucose and secreting the product from the cells in vivo when the respective protein is combined in appropriate proportions with the other three proteins of the cellulose synthase operon.

Also provided are novel recombinant DNA vectors for the expression of heterologous genes in Acetobacter. One such vector comprises a functional Acetobacter origin of replication-containing fragment of p824. All of these vectors contain one or more DNA segments that convey resistance to at least one antibiotic when transformed into a sensitive host cell that is susceptible to transformation, cell division and culture. These vectors may also be developed into shuttle vectors for use in cloning DNA in bacterial host cells, such as E. coli.

BRIEF DESCRIPTION OF THE DRAWINGS

Figure 1C:
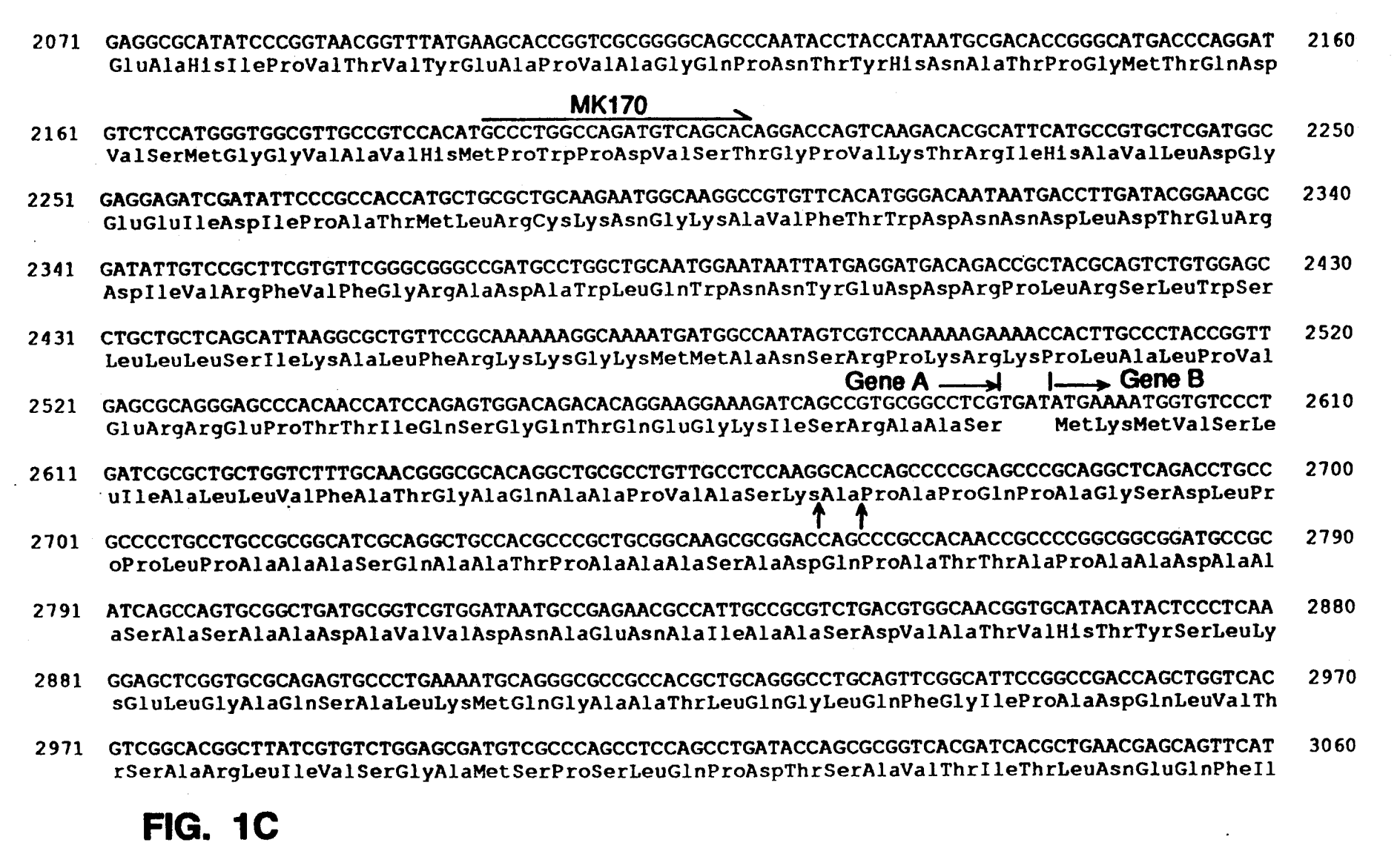
Figure 1E:
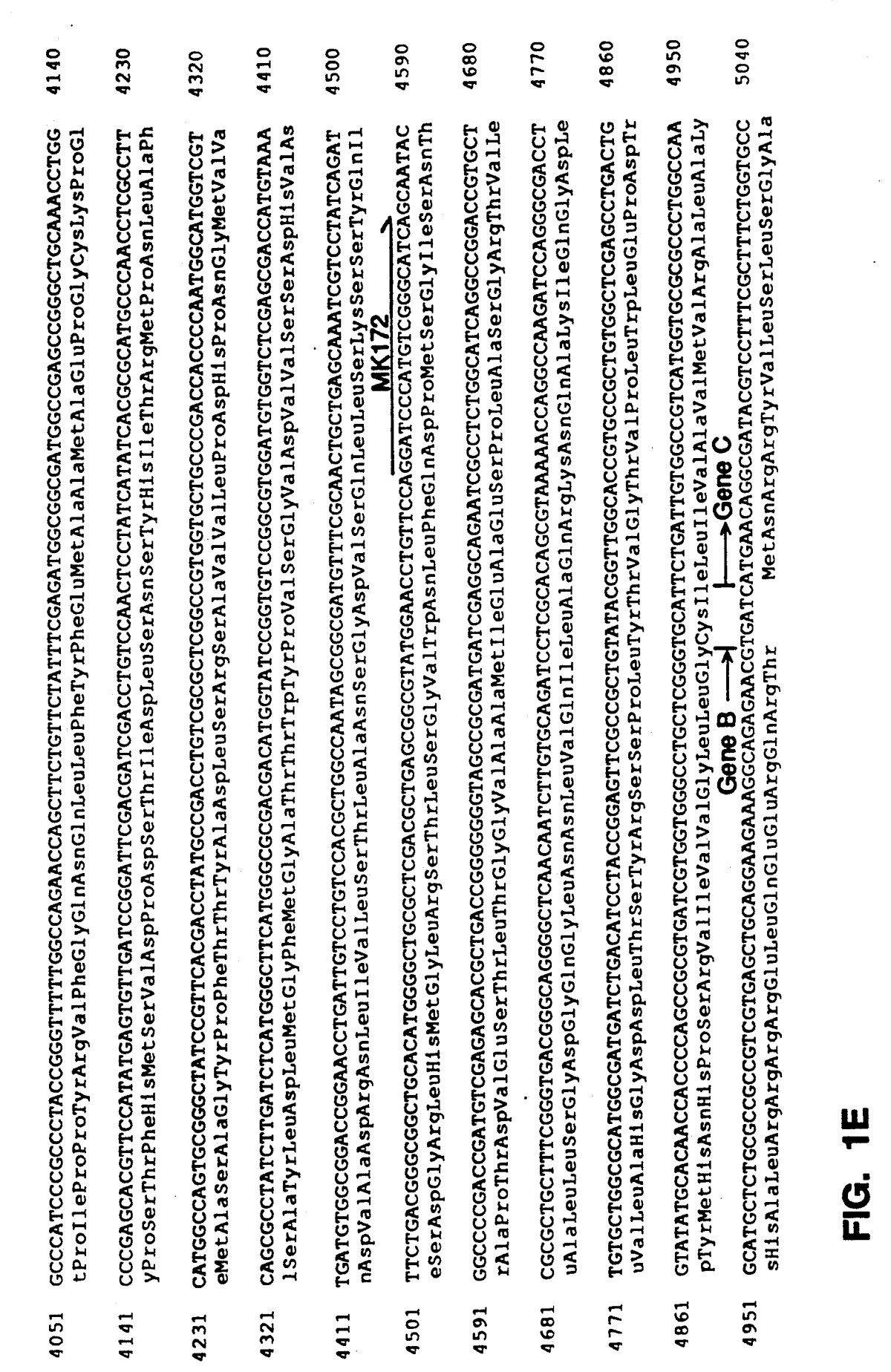

FIG. 1 is the nucleic acid sequence and deduced amino acid sequence of the cellulose synthase operon (SEQ ID No: 1). The cellulose synthase operon is approximately 9217 bp in length and consists of four genes, a 2262 nucleotide sequence designated A (nucleotides 328-2589)(SEQ ID No: 3), a 2406 nucleotide sequence designated B (nucleotides 2594-4999)(SEQ ID No: 4), a 3957 nucleotide sequence designated C (nucleotides 5005 to 8961)(SEQ ID No: 5) and a 468 nucleotide sequence designated D (nucleotides 8964 to 9431)(SEQ ID No: 6). The nucleotide sequences of each gene provided herein may include signal sequences. The mature protein encoded by its respective gene may have undergone processing and if so, the corresponding gene sequence will be shorter than that provided above. For example, the alanine codon which corresponds to the first amino acid of the purified cellulose synthase B protein is flanked by two upward arrows, ↑ ↑. The site of transcription initiation is designated by a downward arrow, ↓, positioned over the A at nucleotide 235. The underlined nucleotide sequence following gene D designates the transcription terminator region comprising an inverted repeat sequence characteristic of stem-and-loop structures. The sequence of oligonucleotide MK170 (SEQ ID No: 7) is indicated above nucleotides 2190 to 2210, and that of MK172 is indicated above nucleotides 4564 to 4583.

FIG. 10 is a depiction of two graphs. FIG. 10A illustrates the rate of cell growth of recombinant strain 1306-21 $P_L$ and control in the absence of acetate as a co-substrate while

FIG. 11 is also a depiction of two graphs. FIG. 11A illustrates the rate of cellulose produced from recombinant strain 1306-21 $P_L$ and control in the absence of acetate as a co substrate while

DETAILED DESCRIPTION OF THE INVENTION

Figure 2A:
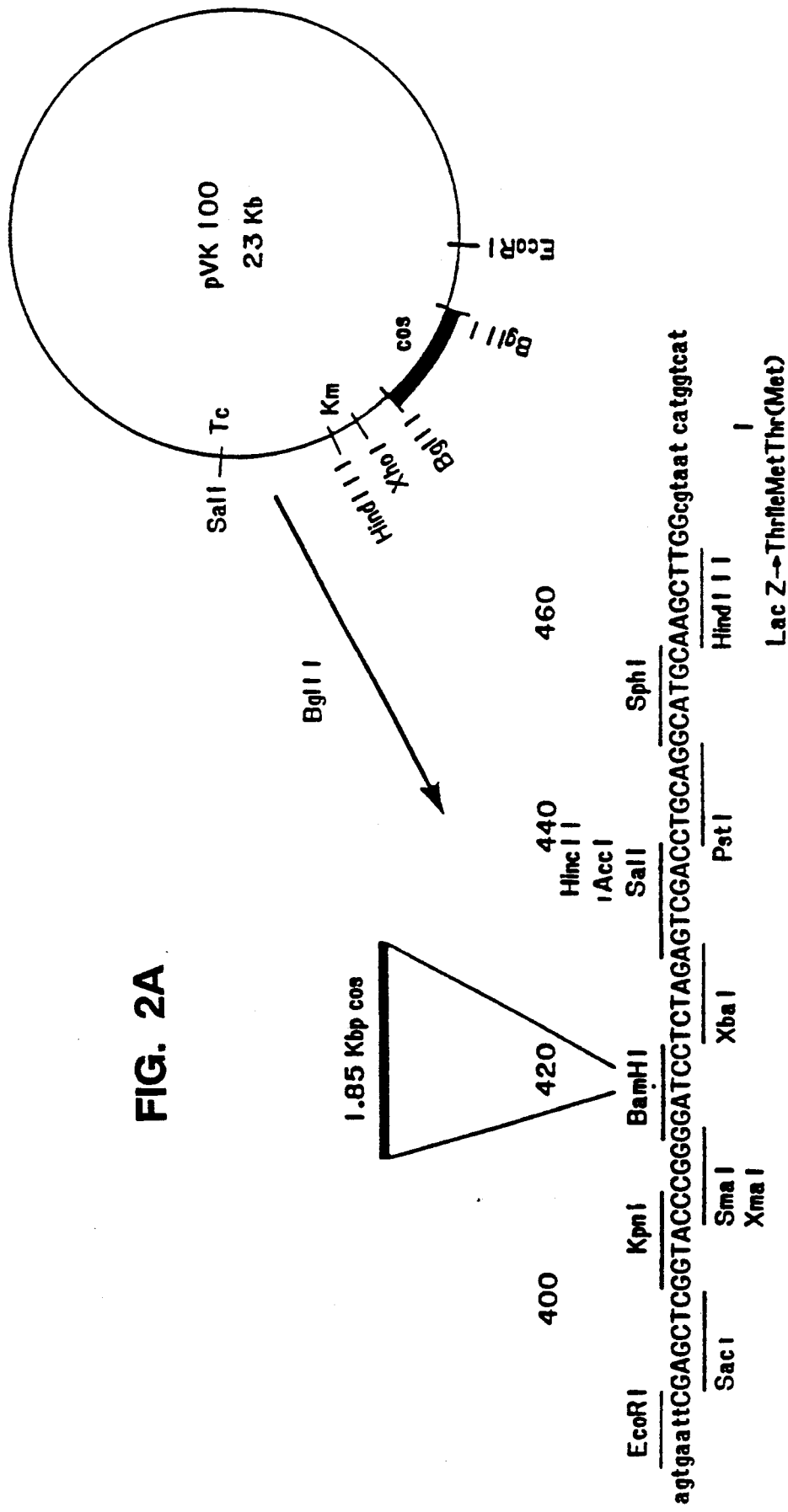
FIG. 2 depicts the construction of cosmid vector pKT230cos5.

In order that the invention herein described may be more fully understood, the following detailed description is set forth.

A. Definitions

As used herein, the term "cellulose synthase" refers to one or more polypeptides associated in the in vivo biochemical conversion of uridine 5'-diphosphoglucose to bacterial cellulose and secretion outside of the cell. A single transcriptional unit containing four genes associated with the synthesis of cellulose synthase is encoded by the nucleic acid sequence provided in FIG. 1 (SEQ ID No: 1).

The term "cellulose synthase gene" is defined as a nucleic acid sequence encoding a polypeptide product associated with the cellulose synthase operon. The term is not limited to any Acetobacter bacterial strain or species. "Cellulose synthase operon," as used herein, refers to a stretch of DNA sequence which codes for a group of protein products associated with cellulose synthesis and secretion outside of the cell. Optionally, the operon may include transcriptional elements such as a promoter region and a transcription terminator region which regulate the expression of the genes encoding the proteins.

"Cellulose synthase activity" is defined by the ability to synthesize cellulose [$\beta$(1-4)-glucan] from UDP glc. This activity is measured in vitro by incorporation of UDP-($^{14}$C) glucose to cellulose (base insoluble) and is measured as nmole (nanomole) of glucose incorporated to cellulose per min.

"Cellulose synthase specific activity" is defined as nmole glucose incorporated to cellulose/min/mg protein. Cellulose synthase specific activity in Acetobacter cells is normally ranged from 0.2 to 6.0 nmole glc/min/mg cell protein.

As used herein, the term "Acetobacter" refers to a genus of microorganisms, and in particular, to members of that genus which produce cellulose.

"Suitable microorganism" refers to a microorganism which is capable of producing cellulose when transformed with one or more of the genes associated with the cellulose synthase operon. Suitable microorganisms include those host cells which are capable of cellulose production in the absence of transformation, or those host cells which are deficient in one or more of the genes whose activity may be replaced by at least one gene of the cellulose synthase operon.

"Operably linked" refers to a juxtaposition such that the normal function of the components can be performed. Thus, a coding sequence "operably linked" to control sequences refers to a configuration wherein the coding sequences can be expressed under the control of these sequences. Such control may be direct, that is, a single gene associated with a single promoter, or indirect, as in the case where a polycistronic transcript is expressed from a single promoter.

"Control sequence" refers to a DNA sequence or sequences necessary for the expression of an operably linked coding sequence in a particular host organism. The control sequences which are suitable for procaryotes, for example, include a promoter, optionally an operator sequence, a ribosome binding site, a transcription terminator, and possibly other as yet poorly understood sequences Eucaryotic cells are known to utilize promoters, polyadenylation signals, and enhancers.

The term "regulatory gene" is defined as a nucleic acid sequence that determines the synthesis of a repressor or activator which is necessary for controlling the expression of the cellulose synthase operon in a particular host.

"Cells" or "recombinant host cells" or "host cells" are often used interchangeably, and all such designation include progeny. Thus, "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny which have the same functionality as screened for in the originally transformed cell are included. Where distinct designations are intended, it will be clear from the context.

As used herein, a polynucleotide "derived from" a designated sequence, for example, the DNA from the cellulose synthase B gene (SEQ ID No: 4), refers to a polynucleotide sequence which is comprised of a sequence of at least 6–20 nucleotides, more preferably at least 15 to 20 nucleotides corresponding, i.e., identical to or complementary to, a region of the designated nucleotide sequence. The correspondence to the nucleic acid sequence will be approximately 70% or greater, will preferably be at least 80%, and even more preferably will be at least 90%.

The correspondence or non correspondence of the derived sequence to other sequences can be determined by hybridization under the appropriate stringency conditions, using standard DNA hybridization technologies in liquid phases or on solid supports. Hybridization techniques for determining the complementarity of nucleic acid sequences are known in the art (see, for example, Sambrook et al. (1989) Molecular Cloning: A Laboratory Manual, Second Edition, Cold Spring Harbor Press, Cold Spring Harbor, N.Y.). In addition, mismatches of duplex polynucleotides formed by hybridization can be determined by known techniques, including digestion with a nuclease such as Sl, that specifically digests single-stranded sequences in duplex polynucleotides.

The derived polynucleotide is not necessarily physically derived from the nucleotide sequence shown, but may be generated in any manner, including for example, chemical synthesis, DNA replication or reverse transcription, which methods are based on the information provided by the sequence of bases in the region(s) from which the polynucleotide is derived.

Similarly, a polypeptide "derived from" a designated sequence, for example, from cellulose synthase B, refers to a polypeptide having an amino acid sequence identical to that of a polypeptide encoded in the sequence, or a protein thereof wherein the portion consists of at least 5–10 amino acids, and more preferably at least 10–15 amino acids, which is immunologically identifiable with a polypeptide encoded in the sequence, or exhibits similar biological activity as that of the reference protein in the in vitro or in vivo assays described herein.

As used herein with reference to an amino acid sequence "substantial correspondence" refers to a sequence usually differing by fewer than 10 amino acids, more usually differing by fewer than 5 amino acids. The recombinant protein, whether "A", "B", "C" or "D", displays substantially the same biological properties as the naturally occurring protein. The biological properties include immunological properties, where antibodies raised to the authentic protein cross-react with the recombinant protein.

The term "recombinant polypeptide" as used herein to characterize a polypeptide useful for the production of cellulose synthase intends a polypeptide encoded by genomic, cDNA, semisynthetic, or synthetic nucleic acid sequences which, by virtue of their origin or manipulation: (1) are not associated with all or a portion of the polynucleotide with which they are associated in nature or in the form of a library; and/or (2) are linked to a polynucleotide other than that to which it is linked in nature.

"Expression system" refers to DNA sequences containing a desired coding sequence and control sequences in operable linkage, so that hosts transformed with these sequences are capable of producing the encoded proteins. In order to effect transformation, the expression system may be included on a vector; however, the relevant DNA may also be integrated into the host chromosome.

"Sensitive host cell" refers to a host cell that cannot grow in the presence of a given antibiotic without a DNA segment containing a gene that confers resistance thereto.

As used herein, the term "vector" refers to a polynucleotide suitable for transferring nucleic acid sequences into a host cell. The term may include plasmids, minichromosomes, phage, naked DNA and the like.

B. General Description

The methods illustrated below to obtain one or more DNA sequences encoding genes of the bacterial cellulose synthase operon are merely for purposes of illustration and are typical of those that might be used. However, once the genes have been identified, other procedures may also be employed, as is understood in the art.

Obtaining The Coding Sequences For The Bacterial Cellulose Synthase Operon

The polynucleotide encoding the bacterial cellulose synthase operon was obtained from an Acetobacter DNA library, as set forth in the examples, and genetic complementation was used to identify the genes.

The procedures for obtaining the nucleotide sequence encoding the bacterial cellulose synthase operon employ a number of individual steps that required adaptation for Acetobacter DNA, and include (1) preparation and characterization of cellulose negative (Cel—) mutant Acetobacter strains; (2) construction of appropriate vectors for cloning; (3) construction of an Acetobacter DNA library; (4) identification and isolation of DNA insert sequences capable of restoring cellulose synthase activity in the Cel— Acetobacter mutants; (5) mapping and subcloning of the nucleotide sequences encoding the bacterial cellulose synthase operon for both sequence analysis and localization of the cellulose synthase coding sequences; and (6) cloning and expression of the DNA encoding the products of the cellulose synthase operon.

Confirmation of the cloned sequence may be performed by comparing the N-terminal amino acid sequence of the recombinantly produced bacterial cellulose synthase with that purified from a native Acetobacter source. In addition, the amino acid sequence deduced from the cloned nucleotide sequence may be compared with the primary sequence of a protein obtained from a native Acetobacter source and purified.

Attempts to clone the gene encoding cellulose synthase were initially directed at the identification of the B gene (SEQ ID No: 4). While the cellulose synthase B gene has been cloned and sequenced, the interpretation of the 5' end of this gene was complicated for a variety of reasons. For example, the transcriptional and translational signals in Acetobacter are not characterized and control signals similar or analogous to those known for E. coli control signals were not present in the upstream region of the codon for alanine (the N-terminal residue of the purified native protein). However, the proximity of an open reading frame upstream of this gene suggested that this gene was part of a polycistronic message. Therefore, additional studies to sequence the open reading frames both upstream and downstream of this gene were performed as described herein. These studies revealed the identity of four closely linked genes bounded at the 5' end by a single promoter and at the 3' end by a transcription terminator region.

While the precise function of each of these gene products has not been confirmed, complementation studies indicate that strains that are defective in cellulose synthase activity can be complemented by gene B, and that cellulose negative mutants that were defective in both cellulose synthase and diguanylate cyclase activities are complemented by gene A (SEQ ID No: 3). Cellulose negative class III mutants are complemented by a DNA fragment that codes for genes C (SEQ ID No: 5) and D (SEQ ID No: 6). The mutants in this group make cellulose in vitro and have all the enzymatic activities necessary for cellulose production. Gene D encodes a protein that is associated with cellulose synthesis. Disruption of this gene significantly reduces cellulose synthesis.

Genes C and D may code for regulatory, structural, membrane bound or processing proteins required in cellulose synthesis in vivo. The availability of coding sequences for their respective gene product permits the synthesis of large amounts of each protein for studies to further elucidate the mechanism of cellulose synthesis.

Expression of Bacterial Cellulose Synthase

According to one method of the invention, the polynucleotide encoding the cellulose synthase operon may be cloned into an appropriate vector, transformed into a suitable microorganism host and cultured under conditions which permit the expression of cellulose synthase. Alternatively, given the sequence identity of each gene in this operon, each gene may be independently cloned and expressed to produce the desired gene product.

Transcription of the polynucleotide sequences encoding the cellulose synthase operon gene products may be performed using the endogenous Acetobacter promoters or, alternatively, may be driven by heterologous bacterial promoters, including those derived from E. coli or B. subtilis. Many of the heterologous promoters described herein, such as the lac, trp, $P_L$ and tac are regulated promoters and are therefore useful in the method of the invention to control the expression of the bacterial cellulose synthase operon or individual polypeptides therein.

Regulation of the heterologous promoters may utilize either positive or negative control elements. For example, a regulatory gene encoding a repressor which recognizes an operator associated with a heterologous promoter (e.g., the lacI repressor) may be introduced into the host system. Another method of regulation may utilize the tac promoter under the control of the lac repressor since the tac promoter contains the binding site for the lac repressor protein. Alternatively, the level of tryptophan present in growth media can provide for regulation of the trp promoter.

Further, constitutive promoters such as the $P_L$ promoter of the E. coli phage lambda, which may be regulated by temperature sensitive repressors, are useful in the present invention. The $P_L$ promoter is regulated by a temperature-sensitive repressor, cI, which represses $P_L$ transcription at low temperatures but not at elevated temperatures. Thus, to regulate the $P_L$ promoter in Acetobacter strains at temperatures below 37° C., an additional temperature-sensitive repressor gene may be present within the transformed host. Alternatively, the $P_L$ promoter may be used to constitutively express cellulose synthase polypeptides in the absence of a temperature-sensitive repressor gene in Acetobacter strains capable of growth at temperatures above 37° C.

Yet another means to control expression of the cellulose synthase operon may employ a heterologous transcription terminator to stabilize the mRNA transcript. For example, the transcriptional terminator isolated from the crystal protein of B. thuringienesis has been shown to increase the expression level of many proteins in E. coli and in B. subtilis by stabilizing their mRNAs. Similarly, it is believed that this terminator, or other such terminators, may be used to increase the mRNA level from the cellulose synthase operon in Acetobacter. It is expected that the increased mRNA levels will enhance cellulose synthesis in the recombinant Acetobacter strains.

The resulting constructions may be inserted into a suitable, cellulose-producing microorganism and either replicated independently using an appropriate expression vector or, if plasmid instability is thought to be a problem, the promoter-gene construct may be integrated directly into the chromosome of the host microorganism. The cellulose-producing host microorganism may be either a cellulose synthase negative strain or a cellulose synthase positive strain. In the former example, one or more of the genes of the cellulose synthase operon will restore the cellulose producing ability of the host microorganism. It is expected in the latter example that the introduction of the recombinant cellulose synthase operon will increase both the cellulose synthase activity and cellulose production of the recombinant strain.

Replacement of the chromosomal cellulose synthase operon promoter with heterologous bacterial promoters has several advantages over a plasmid system designed to overexpress cellulose synthase. Chromosomal promoter replacement avoids any potential problems which may be due to plasmid instability. It also removes the need for an antibiotic to maintain plasmid selection. Lastly, chromosomal promoter replacement removes the control of the operon from Acetobacter, allowing for a stronger, constitutive promoter or providing for control using a regulated promoter.

The nucleotide sequence encoding the genes of the bacterial cellulose synthase operon of the invention may be expressed in a variety of procaryotic systems, including E. coli, Streptomyces, Acetobacter, Agrobacteria, Rhizobium, Pseudomonas, Alcaligenes, Zymomonas, Zoogloea, blue-green algae, and Sarcina ventricculi, with E. coli and Acetobacter being preferred.

Since cellulose synthase is of bacterial origin, vectors suitable for the expression of cellulose synthase are known in the art and may include hybrid shuttle vectors for the development of host vector systems for acetic acid bacteria, such as Acetobacter. Fukaya, et al., (1985) Agric. Biol. Chem. 49:2083-2090, describe several shuttle vectors of relatively small size, with selectable antibiotic gene markers, and capable of replicating in E. coli and Acetobacter. Fukaya, et al., (1989) App. Env. Microbiol, 55:171-176, describe a shuttle vector for E. coli and Acetobacter species, pmv24, which allows translation of a cloned sequence as a fusion protein with β-galactosidase.

The present invention also provides an endogenous Acetobacter vector for use in the cloning and expression of the cellulose synthase genes. This vector, called p824, is small, and lacks the large mobilization region present on the pKT230cos5 conjugation vector described herein. The small size of p824 makes it easier to manipulate as a cloning vector. Analysis of the insert DNA in this vector should also be greatly facilitated due to its small size. The p824 vector can be used to directly clone genes from one Acetobacter host to another, thereby eliminating the host restriction barrier and associated rearrangements/deletions that occur during conjugation of pKT230cos5 cosmids from E. coli to Acetobacter.

The endogenous plasmid may be used for direct Acetobacter-Acetobacter transfer and may also be used to develop shuttle vectors. Thus, the present invention also provides both cloning and expression vectors (for E. coli and Acetobacter species), using appropriate control sequences which allow direct transcription and translation of a desired sequence using, for example, the E. coli lac promoter and its translational initiation signal. Transformation of Acetobacter with these vectors results in transformation efficiencies useful for various types of cloning and expression experiments.

Cellulose Production

Increased cellulose production by Acetobacter grown in agitated cultures may be obtained by culturing the cells in polyacrylamide-containing polymers as shown in related application, U.S. Pat. No. 5,114,849 filed Oct. 26, 1990 which is incorporated herein by reference. The polyacrylamide-containing polymers effective in stimulating the greatest increase in cellulose yield in the agitated cultures are high molecular weight polymers having a weight average molecular weight range of about $10^6$ to about $10^7$ daltons, e.g., Floxan EA1340 (Henkel Corporation).

Protein Recovery

Purification of the recombinant cellulose synthase is accomplished using procedures similar to those used to recover the native material. Generally the cultured cells are disrupted using mechanical or enzymatic means, for example using a French Press, sonication or treatment with lysozyme and EDTA, and then collected by centrifugation to recover the pellet containing the cellulose synthase activity.

The pellet is resuspended and centrifuged to remove soluble protein and the collected pellet is solubilized with detergent, for example, with digitonin or Triton X-100 with 20% glycerol. Optionally, one may concentrate the desired activity using ultrafiltration or centrifugation.

The enzyme is entrapped using cellulose, its own insoluble product, to separate the enzyme from other detergent-solubilized proteins. The entrapped enzyme may than be recovered from the cellulose by digestion of the cellulose with pure cellulase.

Standard Methods

Most of the techniques which are used to transform cells, construct vectors, achieve complementation and the like are widely practiced in the art, and most practitioners are familiar with the standard resource materials which describe specific conditions and procedures (see for example, Sambrook, et al., (1989).

In addition, Miller, J. M. (1972) Experiments in Molecular Genetics, Cold Spring Harbor, N.Y., provides general procedures useful for conjugation experiments with bacteria. However, for convenience, the following paragraphs may serve as a quideline.

Control Sequences And Corresponding Hosts

Procaryotes most frequently are represented by various strains of E. coli. However, other microbial strains may also be used, such as bacilli, for example, Bacillus subtilis, various species of Acetobacter, Pseudomonas and Streptomyces. In such procaryotic systems, vectors which contain replication sites and control sequences derived from a species compatible with the host are used. For example, E. coli may be transformed using derivatives of a vector such as pKT230, available from the American Type Culture Collection (ATCC), Rockville, Md. (ATCC. No. 37294), and described by Bagdasarian, et al., (1981) Gene 16:237–247 or by using derivatives of pBR322, a plasmid derived from an E. coli species and described by Bolivar, et al., (1977) Gene 2:95.

Plasmid pKT230 has a broad host range origin of replication, an E. coli origin of replication, tra genes necessary for conjugation, and a streptomycin resistance marker. Plasmid pBR322 contains genes for ampicillin and tetracycline resistance, and thus provides additional markers which can be either retained or destroyed in constructing the desired vector. Commonly used procaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang. et al., (1977) Nature 198:1056), the tryptophan (trp) promoter system (Goeddel, et al., (1980) Nucleic Acids. Res. 8:4057), the hybrid tac promoter (De Boer, et al., (1983) Proc. Natl. Acad. Sci. U.S.A. 80:21–25), and the lambda derived $P_L$ promoter (Shimatake, et al., (1981) Nature 292:128) and N gene ribosome binding site, which has been made useful as a portable control cassette. U.S. Pat. No. 4,711,845, issued Dec. 8, 1987 describes this portable control sequence which comprises the first DNA sequence that is the $P_L$ promoter operably linked to a second DNA sequence corresponding to the $N_{RBS}$ upstream of a third DNA sequence having at least one restriction site that permits cleavage within six base pairs 3' to the $N_{RBS}$ sequence. U.S. Pat. No. 4,666,848, issued May 19, 1987, discloses additional vectors with enhanced expression capabilities useful to express bacterial cellulose synthase. Also useful is the alkaline phosphatase (phoA) system described by Chang, et al., in European Patent Publication No. 196,864, published Oct. 8, 1986 and incorporated herein by reference. While each of these publications provides useful expression systems, any available promoter system compatible with procaryotes can be used.

INTRODUCTION OF DNA INTO ACETOBACTER

A. Conjugations

Conjugation is a technique useful for transferring foreign DNA into a targeted host cell. The cosmid vectors constructed in the present invention are not easily transferred from E. coli for replication in a different bacterial host such as Acetobacter. In such cases, a helper plasmid, such as pRK2013 (Figurski and Helinski, (1979) Proc. Natl. Acad. Sci. U.S.A. 76:1648–1652) may be used to assist in transferring the cosmid vector containing the desired DNA insert from the donor cells into the recipient cells. For conjugation, donor, mobilizing and recipient cells are mixed and mated on plates. Cells which acquire the donor are selected for by growth on plates containing antibiotic to which the transformed recipient cells are resistant. Miller, supra, also discloses a conjugation procedure where nutritional markers are used to select recipient cells. Another conjugation procedure suitable for mass screening is the "multiple spot conjugation method" set forth in detail in Example V, infra.

B. Transformations

Depending on the host cell used, transformation is done using standard chemical techniques appropriate to such cells or may employ electroporation. The calcium treatment employing calcium chloride, as described by, for example, Cohen, S. N., (1972) Proc. Natl. Acad. Sci. U.S.A. 69:2110, is used for procaryotes or other cells which contain substantial cell wall barriers.

The disadvantage of the chemical approach with an uncharacterized species is that the chance of success with any one protocol is small; hence, some experimentation to optimize conditions to obtain meaningful levels of transformants may be required. Recently exposure of bacteria to a strong electrical field has been shown to successfully transform a broad range of bacteria, including Pseudomonas and E. coli. Electroporation as applied to bacteria has been available since 1983 (Shivarova, et al., (1983) Z. Allg. Microbial. 23:595). Dower, et al., ((1988) Nuc. Acid. Res. 16:6127) has demonstrated that the efficiency of electroporation in E. coli can be 10- to 100-fold better than the best levels obtained by chemical means.

Two basic parameters affect the efficiency of electroporation. One is the field force and the other is the time period (pulse duration) over which the field force decays. Operationally, cells experience the field force (E) in a spectrophotometer-type cuvette, with a constant electrode distance (d). Thus, the amount of voltage (V) applied to the cuvette determines the field force (E=V/d). Accurate delivery of voltage to the sample occurs if the charge is first stored in a capacitor. The pulse duration, dispersion of the force field, is typically delivered in a logarithmic form and the duration of the decay is determined by a combination of series capacitors and parallel resistors.

As demonstrated herein, the optimal field force for the Acetobacter strains used in the present invention varies between 9 and 9.5 Kilovolts/cm (KV/cm). A study of pulse duration (RC values) using from 25-100 uF (series) versus 200–1200 ohms demonstrated that 25 uF/750 ohms (=18.75 msec) is optimal for Acetobacter strain 1306-24. The level of transformation obtained (approximately $10^7$ transformants/ug) is about $10^2$-fold higher than that obtained by chemical treatment (Fukaya, et al., (1985) *Agri. Biol. Chem.* 49:2091-2097).

It was also determined that the transformation frequency of DNA prepared from Acetobacter is $10^3$-fold higher than when the DNA is prepared from *E. coli*. Without wishing to be bound by theory, this species barrier is probably due to endonuclease host restriction activity upon unmodified, possibly unmethylated, *E. coli* DNA. Methods which reduce this restriction barrier have not been explored herein; however, the restriction barrier can be avoided by developing an Acetobacter-Acetobacter vector as described herein.

Construction of Acetobacter DNA Library

A DNA library is prepared from Acetobacter by isolating nucleic acid from Acetobacter cells and degrading the RNA in the sample. The recovered DNA is partially digested with an appropriate restriction enzyme such as Sau3A and the DNA is subsequently size fractionated, for example, using a sucrose gradient. A fraction containing a selected size range of molecules is ligated into a cosmid vector, and then conventionally packaged into lambda phage particles. The phage particles are then used to infect a suitable host, such as *E. coli*. A random number of isolates may be selected to isolate the cosmid DNA to determine the sizes of the inserted DNA and thereafter, a number of clones sufficient to be representative of the genome are picked, grown and screened.

Vector Construction

Construction of suitable vectors containing the desired coding and control sequences employ standard ligation and restriction enzyme techniques which are well understood in the art. Isolated plasmids, DNA sequences, or synthesized oligonucleotides are cleaved, tailored, and religated in the form desired.

Site-specific DNA cleavage is performed by treating the DNA with the suitable restriction endonuclease(s) under conditions which are generally understood in the art, and the particulars of which are specified by the manufacturer of these commercially available restriction enzymes. See, e.g., New England Biolabs, Product Catalog (New England Biolabs, Beverly, Mass.). In general, about 1 ug of DNA is cleaved by one unit of enzyme in about 20 ul of buffer solution. An excess of restriction enzyme is typically used to insure complete digestion of the DNA substrate; however, it may be desirable to carry out partial digestions in which some but not all of the sites of a given restriction enzyme in the DNA are cleaved. Such partial digestions are accomplished by varying the concentration of restriction enzyme or length of time the restriction digestion is carried out. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499 560; Lawn, et al., (1981) *Nuc. Acids Res.* 9:6113 6114 and Goeddel, et al., (1980) *Nuc. Acids Res.* 8:405).

Restriction cleaved fragments may be blunt ended by treating with the large fragment of *E. coli* DNA polymerase I (Klenow) in the presence of the four deoxyribonucleoside triphosphates (dNTPs) using incubation times of about 15 to 25 min at 20° to 25° C. in 50 mM Tris pH 7.6, 50 mM NaCl, 6 mM MgCl, 6 mM dTT, about 1 U/ul Klenow and 100 uM dNTPs. The Klenow fragment "fills in" opposite 5' sticky ends but the 3'>5' exonuclease activity of the enzyme chews back protruding 3' single strands in the absence of a template region. If desired, selective repair can be performed by supplying only one, or selected, dNTPs within the limitations dictated by the nature of the sticky ends. After treatment with Klenow, the mixture is extracted with phenol/chloroform and ethanol precipitated. Treatment under appropriate conditions with Sl nuclease or Bal31 results in hydrolysis of any single-stranded portion.

Several methods for synthesizing oligonucleotides have been described in the literature. One known method is the triester method of Matteucci, et al., (1981) *J. Am. Chem. Soc.* 103:3185-3191, also described in Narang, et al., (1979) *Meth Enzymol.* 68:90 and U.S. Pat. No. 4,356,270. Another known method is the diester method of Brown, et al., (1979) *Meth. Enzymol.* 68:109. Automated synthesis methods may also be used. Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, and 1-2 mM ATP. If kinasing is for labeling of probe, the ATP will contain high specific activity gamma-$^{32}$P.

Ligations are performed in 15-30 ul volumes under the following standard conditions and temperatures: 20 mM Tris-HCl, pH 7.5, 10 mM MgCl, 10 mM DTT, 33 ug/ml BSA, 10 mM-50 mM NaCl, and either 40 uM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 ug/ml total DNA concentrations (5 100 nM total end concentration). Intermolecular blunt end ligations (usually employing a 10-30 fold molar excess of inserts) are performed at 1 uM total ends concentration.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of $Na^+$ and $Mg^{+2}$ using about 1 unit of BAP per ug of vector at 60° C. for about one hour. In order to recover the nucleic acid fragments, the preparation is extracted with phenol/chloroform and ethanol precipitated. Alternatively, religation can be prevented in vectors which have been double digested by additional restriction enzyme digestion of the unwanted fragments.

Modification of DNA Sequences

For portions of vectors derived from cDNA or genomic DNA which require sequence modifications, site-specific primer directed mutagenesis is used. This technique is now standard in the art, and is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage DNA, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The plaques are transferred to nitrocellulose filters and the "lifts" hybridized with kinased synthetic primer at a temperature which permits hybridization of an exact match, but at which the mismatches with the original strand are sufficient to prevent hybridization. Plaques which hybridize with the probe are then picked and cultured, and the DNA is recovered. Details of site specific mutation procedures are described below in specific examples.

Verification of Construction

In the constructions set forth below, correct ligations for plasmid construction are confirmed by first transforming $E.\ coli$ strain MM294, or other suitable hosts with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, et al., (1969) *Proc. Natl. Acad. Sci. U.S.A.* 62:1159, optionally following chloramphenicol (Cm) amplification (Clewell, (1972) *J. Bacteriol.* 110:667). The isolated DNA is analyzed by restriction and/or sequenced by the dideoxy method of Sanger, et al., (1977) *Proc. Natl. Acad. Sci. U.S.A.* 74:5463 as further described by Messing, et al., (1981) *Nuc. Acids Res.* 9:309, or by the method of Maxam, et al., (1980) *Methods in Enzymology* 65:499.

In order that the invention described herein may be more fully understood, the following examples are set forth. It should be understood that the examples are for illustrative purposes only and are not to be construed as limiting the scope of this invention in any manner.

EXAMPLE I

Preparation of Cellulose Negative Acetobacter Strains

In the following examples a number of culture media were used. Unless otherwise indicated the media were formulated as follows:

R20-2 medium has the following composition:

| Compound | Final Concentration |
|---|---|
| Bacto-peptone | 5 g/l |
| Yeast Extract | 5 g/l |
| Na₂HPO₄ | 5 g/l |
| Citric Acid | 1.15 g/l |
| Carbon Source | As specified (if not specified, 2% glucose) Final pH 5.0 ± 0.2 |

Minimal medium R70 (also referred to as Acetobacter Minimal Medium or "AMM"), has the following composition:

| Compound | Final Concentration (mM) |
|---|---|
| (NH₄)₂SO₄ | 25 |
| KH₂PO₄ | 7.3 |
| MgSO₄ | 1.0 |
| FeSO₄ | 0.013 |
| CaCl₂ | 0.10 |
| Na₂MoO₄ | 0.001 |
| ZnSO₄ | 0.006 |
| MnSO₄ | 0.006 |
| CuSO₄ | 0.0002 |
| | pH - 5.0 |
| Glucose | 2% or 4% (w/v) unless otherwise specified |

For all studies using R-70 medium and modifications thereof, the following vitamin mixture was added to the minimal medium at a 100-fold dilution:

| Compound | Vitamin Mixture mg/L |
|---|---|
| Inositol | 200 |
| Niacin | 40 |
| Pyridoxine HCl | 40 |
| Thiamine HCl | 40 |
| Ca Pantothenate | 40 |
| Riboflavin | 20 |
| Para-aminobenzoic acid | 20 |
| Folic Acid | 0.2 |
| Biotin | 0.2 |

R70-2 medium was a modified form of R70. R70-2 had the following composition:

| Ingredient | Final Concentration (mM) |
|---|---|
| (NH₄)₂SO₄ | 25 |
| KH₂PO₄ | 7.3 |
| Na Citrate | 4.0 |
| MgSO₄ | 1.0 |
| FeCl₃ | 0.01 |
| CaCl₂ | 0.10 |
| Na₂MoO₄ | 0.001 |
| ZnSO₄ | 0.005 |
| MnSO₄ | 0.005 |
| CuSO₄ | 0.001 |
| CoCl₂ | 0.001 |
| NiCl₂ | 0.001 |
| vitamin mixture | 10 ml/liter |
| Glucose | as specified (usually 2 or 4%, w/v) | final pH = 5.0 ± 0.2

Production of Mutant Acetobacter Strains

Three tissue culture flasks containing 100 ml R70+2% glucose, 2% corn steep liquor E804E (CSL, Corn Products, NJ) medium were inoculated with Acetobacter strain 1306-21 (ATCC No. 53524) (one frozen 2 ml vial to each flask). The flasks were incubated statically for 23 hr at 30° C.

The pellicles formed by the Acetobacter cells in culture were aseptically removed with forceps, blended for approximately 15 seconds and filtered through 4 layers of sterile cheesecloth. The cells were washed two times with 0.9% NaCl by centrifugation for 10 min at 7500 rpm, at 4° C. The cells were resuspended in 20 ml 0.9% NaCl and filtered once more through 4 layers of cheesecloth to remove any remaining clumps.

Mutagenic conditions were selected to give a cell kill of 95% to 99.9%. The cultures were incubated at 30° C. The mutagen was ethyl methansulfonate (EMS, Sigma, St. Louis, Mo.). The EMS concentrations ranged from 1% to 2% (v/v) and the incubation times ranged from 60 min to 210 min. Similar conditions were used with Acetobacter strains 1306-3 and 1306-11 (ATCC Nos. 53264 and 53263, respectively).

Two procedures were used to isolate the Cel− Acetobacter strains, 1) mutagenesis without expression, and 2) mutagenesis with expression.

Mutant Acetobacter Strains From EMS Mutagenesis Without Expression

Acetobacter strain 1306-21 was treated with EMS and then directly plated on R20-2 medium to determine percent survival. The plates from the EMS mutagenesis of 1306-21 were examined for potential Cel− colonies as follows. The mutagenized culture was plated and after seven (7) days presumptive Cel− colonies were picked. Cel− mutants may be identified on plates as flat and shiny colonies whereas wild type colonies have a rough, dry appearance. In agitated culture Cel+ strains form pellets while Cel− cultures produce a suspension of single cells. The frequency of Cel− colonies was determined to be in the range of from 0.05% to 2.0%. A similar technique was used to isolate Cel− strains from Acetobacter strains 1306-3 and 1306-11 and similar mutation frequencies were observed.

Mutant Acetobacter Strains From EMS Mutagenesis with Expression

Samples (approximately 0.05 ml) of EMS-treated Acetobacter cells (strain 1306-21) were inoculated into tubes (2 ml, R20-2 broth) and allowed to grow as standing cultures, to permit expression of mutated genes. Culture samples were serially diluted and plated on R20-2 plates. After incubation, the colonies were screened for potential Cel− types using the above-described protocol and similar mutation frequencies were obtained. A similar technique was used to isolate Cel− strains from Acetobacter strain 1306-3 and 1306-11.

EXAMPLE II

Characterization of Cellulose Negative Acetobacter Strains

Cellulose Synthase Activity Assay

The cellulose synthase assay used to detect in vitro cellulose synthase activity of Cel− Acetobacter mutant strains was a modification of the procedure described by Aloni, et al., (1982) *Proc. Natl. Acad. Sci. U.S.A.* 79:6448–6452, which measures production of alkali insoluble polymers (cellulose) from uridine 5′-diphospho-($^{14}$C)-glucose (UDPG). This assay was adapted for the screening of Acetobacter Cel− mutants. After incubation (10 min. at 30° C.), unreacted UDPG in each reaction mixture was separated from the cellulose by heating with NaOH (95° C. for 1 hr) and filtering. The radioactively-labeled ($^{14}$C) cellulose retained on the filter was then quantitated by scintillation counting.

The amount of total protein used in the assay depends upon the state of purification of the cellulose synthase. Two or three different sample dilutions were assayed to obtain at least one result in the linear range of the assay (<20% of total UDPG consumed).

The 0.2 ml assay mixture contained, as final concentrations, 0.2 mM ($^{14}$C) UDPG (7.5 cpm/pmole), 50 mM Tris, pH 7.5, 10 mM $MgCl_2$, 1 mM EDTA, 2 mM $CaCl_2$, and the sample to be assayed. Cyclic diguanosine monophosphate (c-di-GMP) was added to 5 uM to some of the assay tubes (c-di-GMP activates the cellulose synthase). Controls included a tube containing no added sample, and a tube containing the sample, denatured prior to the incubation by adding 4 ml of 0.5M NaOH.

The timed reactions were commenced by adding enzyme, vortexing the mixture, and placing the tubes into a 30° C. water bath. Succeeding tubes were started at timed intervals. After 10 min, each reaction was terminated by removing the tube from the water-bath, adding 4 ml of 0.5M NaOH, and vortexing. When all the reactions were stopped, about 20 mg cellulose was added to each tube to act as carrier for the ($^{14}$C) cellulose. The tubes were then heated in a water bath 95° C. for one hour to digest the cells.

Using a vacuum manifold, the contents of each assay tube were filtered through a Whatman GF/A filter to isolate the cellulose product (removing any unreacted $^{14}$C UDPG), by passing the reaction mixture through the filter; rinsing the assay tube 3X with deionized water, passing the rinse water; washing the filter 2X with 20 ml deionized water; then with 20 ml 0.5M HCl; followed by 20 ml deionized water and 20 ml methanol.

Cellulose production was quantified by scintillation counting. Each filter was placed in a scintillation vial with 10 ml scintillation fluid (NEN Atomlight, Boston, Mass.) and quantitative cellulose production determined by ($^{14}$C) UDPG incorporation into base insoluble material by scintillation counting. To obtain the specific activity of the ($^{14}$C) UDPG, an aliquot of the 2 mM ($^{14}$C) UDPG stock solution was counted.

The total possible cpm of the assay was determined from the stock-solution aliquot, and the fraction of total UDPG consumed from each assay tube was calculated as follows:

Fraction of total *UDPG* consumed =

$$\frac{((\text{cpm filter}) - (\text{cpm of blank}))}{(\text{total counts}) - (\text{cpm of blank})}$$

The nmole of *UDPG* consumed per minute was calculated as:

nmole *UDPG*/min = (fraction of total *UDPG* consumed) ×

(40,000 pmole) × (1/10 min)

Activity was expressed on the basis of nmole per minute per ml sample, or nmole per minute per mg protein.

Assay for Diguanylate Cyclase Activity

The diguanylate cyclase assay was used to identify Acetobacter hosts lacking two or more specific activities, such as a deficiency in cellulose synthase activity and diguanylate cyclase activity. The enzyme diguanylate cyclase catalyzes the production of c-di-GMP, a cellulose synthase activator, from quanosine triphosphate (GTP).

The cells were grown, washed, and sonicated as described below for the screening assay. Diguanylate cyclase activity was measured using an assay similar to that reported in Ross, et al., (1987) *Nature* 325:279. Sonicated cells (1 mg/assay tube) were incubated for 10 min at 30° C. in a 0.1 ml reaction mixture containing 0.2 mM [alpha$^{32}$P]GTP, 50 mM Tris HCl, pH 7.5, 10 mM MgCl$_2$, 1 mM EDTA, 5 ml CaCl$_2$, 2 mM phosphocreatine, and 24 units/ml creatine phosphokinase. The reaction was terminated with 10 ml (w/v) 100% trichloroacetic acid. After centrifugation to remove the precipitate, 10 ml of each reaction mixture was spotted on a thin layer chromatography (TLC) plate (Polygram Cel 300 PEI, Macherey-Nagel, Duren, W. Germany, U.S. distributor Sybron/Brinkman, Westbury, N.Y.). The TLC plate was developed in 1.5M KH$_2$PO$_4$, pH 3.65, for about 2 hr, autoradiographed, and the areas on the TLC plate corresponding to GTP and cyclic di-GMP were excised and counted in a scintillation counter.

Screening Assay

To observe restoration of cellulose synthase activity, one needs to isolate a strain which is cellulose synthase negative and diguanylate cyclase positive. The following screening assay is a modification of the cellulose synthase activity assay described above and may be used to determine mutations involving two different enzymes by comparing cellulose synthase activity in the presence or absence of GTP or c-di-GMP. The assay measures cellulose production by suspended, sonicated cells.

Mutant Acetobacter strains were classified by assaying sonicated cells under several different conditions. Three classes of Acetobacter mutations were identified. Class I (cellulose synthase negative) strains produced no cellulose under any assay conditions. Class II (diguanylate cyclase negative) strains produced cellulose in the presence of c-di GMP, but not in the presence of GTP. Class III mutants produced cellulose following activation by either GTP or c-di-GMP. Mutants in Classes II and III contain cellulose synthase, and show activity in vitro, but produce little or no cellulose in vivo. The deficiency in the Class III mutants has not been defined biochemically.

The screening assay was conducted under the following conditions: 1) no nucleotide added; 2) 0.4 mM GTP added; and 3) 5 uM c-di-GMP added.

Except for the source of enzyme and the buffer used, the assay procedure and controls were as described above for the cellulose synthase activity assay.

Six mutant Acetobacter strains were assayed in a single screening. Each time an Acetobacter strain having both cellulose synthase activity and diguanylate cyclase activity was included to monitor consistency between assays.

The selected Acetobacter strains were grown for approximately 24 hours at 30° C. The growth medium contained R70-2, 1% Ambrex 1003 (TYE, Universal Foods, Milwaukee, Wis.), 4% fructose, 0.01% v/v Dow Corning Antifoam B, and 50 mM 3,3-di methylglutaric acid (DMG), pH 5.0., 25 ml of medium was inoculated in a 125 ml baffled shake flask with the cells from a frozen seed vial. Before collecting the cells, R70-2+0.5% TYE and 1% glucose agar plates were streaked to monitor for contamination. The plates were incubated at 30° C. for about 3 days.

Prior to collecting the cells, 5 ml of 0.6M EDTA was added to the medium to prevent clumping. The cells were centrifuged (5000 rpm, 10 min, JA21 rotor) and the supernatant discarded. The pellet was suspended in 20 ml 50 mM potassium phosphate buffer, pH 6.0, and 5 ml 5M NaCl was added to reduce clumping.

Cell density was measured with a Klett meter (10 Klett units ("KU")=approximately 40 mg cells/ml).

The cells were again centrifuged (5 K rpm, 10 min, JA21 rotor) and the supernatant discarded. The pellets were suspended to 20 mg cells/ml in 50 mM N-(2-hydroxyethyl)piperazine, N'-3-propanesulfonic acid (EPPS, Sigma) buffer, pH 7.5.

To sonicate the cells. 0.5 ml of each cell suspension was transferred into a 1.5 ml Eppendorf centrifuge tube. Each tube was sonicated in a cup sonicator (Branson Sonic Power Co., Model 350, Plainview, N.Y.) for 1 min., 80% duty cycle, setting of 7. The assay was performed as described above using 50 ul of sonicated cell suspension for each assay tube, substituting 50 mM EPPS, pH 9.0 for the 50 mM Tris, dropping the 1 mM EDTA, and adding 20 mM MgCl$_2$ in place of 10 mM MgCl$_2$. Each assay condition was duplicated and the duplicates were averaged in the calculations.

Several Cel strains were biochemically characterized. Strain 1306-24 (derived from 1306-3) was found to have normal diguanylate cyclase activity but was defective in cellulose synthase activity. Strains 1306-42 (derived from 1306-21) and C90-1 (derived from 1306-21) were defective in both diguanylate cyclase and cellulose synthase activities. These strains were picked for subsequent studies.

EXAMPLE III

Construction of Cosmid Vector and Conjugation Procedure

Figure 2B:
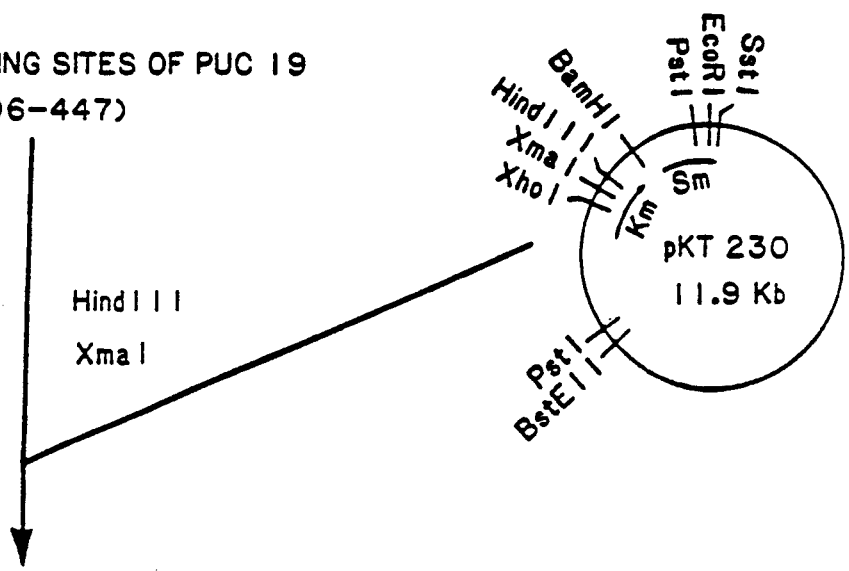
Figure 2B:
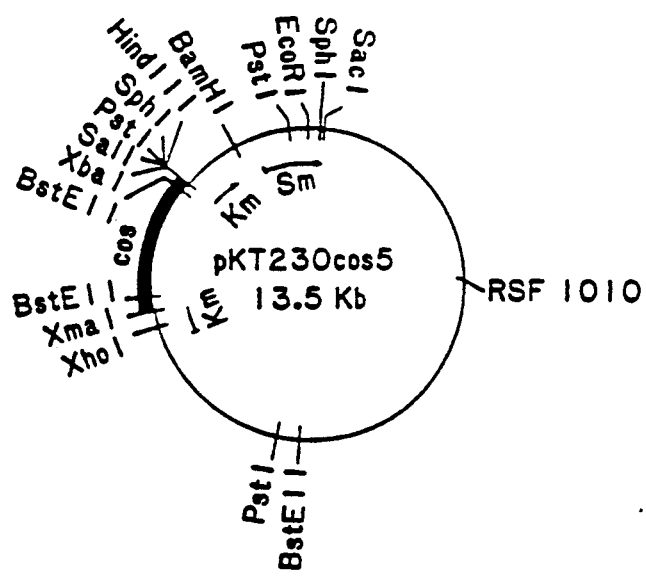

A new cosmid vector, pKT230cos5, was constructed as summarized in FIG. 2 for the cloning of a cellulose synthase gene. This vector contains a streptomycin resistance gene (Sm). the cos fragment of phage lambda and cloning sites for insertion of foreign DNA.

A 1.85 kb DNA fragment containing the lambda cos site was excised from plasmid pVK100 (Knauf and Nester, (1982) Plasmid 8:45 55) by digestion with the restriction enzyme BglII and was cloned in the BamHI site in plasmid pUC19 (New England Biolabs Catalog). The new plasmid, pUC19cos2, was digested with the restriction enzymes HindIII and XmaI and the HindIII-XmaI fragment containing the 1.85 kb cos-containing fragment was cloned into XmaI- and HindIII-digested plasmid pKT230, thereby inactivating the kanamycin-resistance gene. The resulting vector, cosmid pKT230cos5, is not self-transmissible from E. coli to Acetobacter. Therefore, a helper plasmid, pRK2013, is necessary to mobilize the transfer of pKT230cos5 from the donor cells into the recipients cells of Acetobacter strain 1306-24. E. coli strain MM294 transformed with pKT230cos5 was grown at 37° C. in R2 medium (20.0 g Tryptone, 10.0 g yeast extract, 10.0 g NaCl, 1.0 L distilled H$_2$O, pH 6.9 plus 2 g/l glucose (R2-4) and optionally, 15 g/L Bacto agar) containing 100 ug/ml Sm to a Klett reading of 150 KU. E. coli strain HB101 containing the mobilizing plasmid pRK2013 was grown at 37° C. in R2-4 medium containing 50 ug/ml Km to a Klett reading of 150 KU. The Acetobacter recipient cells 1306-24 were grown at 30° C. in R20-2 medium to a Klett reading of 200 KU. 1 ml of each donor, mobilizing and 2 ml recipient cells were mixed and filtered through a 0.2 micron Gelman disposable filter (Gelman, Ann Arbor, Mich.), washed twice with 10 ml of R2 medium without antibiotics. The filter was placed on agar plates containing R2 4 medium. The plates were incubated at 30° C. for 3 hr to allow mating to take place. After mating between the three strains, the conjugation mixture was resuspended in 2 ml of 0.9% sodium chloride.

0.1 ml of this solution was plated on R20-2 medium agar plates containing 50 ug/ml Sm and 20 ug/ml Cm. The plates were incubated at 30° C. for 5 days. Acetobacter strain.1306-24 is naturally resistant to 20 ug/ml Cm, while *E. coli* strains are sensitive to it. Therefore only Acetobacter colonies which had acquired the donor plasmid grew on these selection plates. Subsequent restriction analysis showed that the cosmid pKT230cos5 did not undergo any rearrangements in Acetobacter strain 1306-24.

EXAMPLE IV

Construction of an Acetobacter DNA Library

Lambda phage will package DNA from 38 to 52 kb in length if cos sites are present at both ends. Since the vector pKT230cos5 was relatively small (13.5 kb), a large amount of Acetobacter DNA (28 to 37 kb) could be inserted and packaged in lambda phage particles. Presuming the genome size of Acetobacter is equivalent to *E. coli*, only 700 to 1000 clones are presumed necessary to have a complete gene bank. DNA banks were constructed from Acetobacter strain 1306 3 as follows.

About 26 mg of nucleic acid were isolated from lawns of Acetobacter 1306-3 on R20-2 agar plates. This nucleic acid was treated with RNase A and RNase Tl to degrade the RNA in the sample. A total of 560 ug of DNA was recovered. This DNA was partially digested with the restriction enzyme Sau3A at four different enzyme concentrations. The DNA was fractionated by size on a 10-40% sucrose gradient. The fraction containing the largest number of DNA molecules between 27-38 kb was selected (approximately 2 ug of DNA).

Approximately 1 ug of this DNA was ligated into BamHI-cleaved and dephosphorylated pKT230cos5 DNA, and the ligation mixture was packaged into lambda phage particles. The phage particles were then used to infect *E. coli* strain K802 recA−. Cosmid DNA, isolated from six random *E. coli* isolates, was used to determine the sizes of the inserted DNA fragments. The six clones had DNA inserts ranging from 8 to 40 kb with an average size of 28 kb. Approximately 2000 clones were picked, individually grown in microtiter dishes, and stored for later screening. The bank was designated pKT230cos5:1306-3A2.

EXAMPLE V

Identification And Isolation of Cloned DNA That Restored Cellulose Synthase Activity in Cellulose Negative Acetobacter Strains A genetic complementation assay for restoration of cellulose synthase activity was used to isolate cosmid DNA capable of restoring cellulose synthase activity in the Cel− Acetobacter mutants.

Screening of Acetobacter Gene Bank Through Conjugations

Cosmids from the gene bank pKT230cos5:1306-3A2 (obtained as described in Example IV) were transferred to recipient mutant Acetobacter strain 1306-24 for screening using the mobilizing plasmid pRK2013 in a multiple spot conjugation method described below.

Acetobacter strain 1306-24 was grown in R20-2 medium at 30° C. with shaking for approximately 28 hr to a Klett reading of 100 150 KU. *E. coli* HB101/pRK2013 was grown in R2-4 medium and 50 ug/ml kanamycin (Km) at 37° C. with shaking to a Klett reading of 100 to 150 KU. *E. coli* K802 recA− (pKT230cos5:1306-3A2) cultures were inoculated from frozen microtiter trays with a flamed frog into microtiter dishes containing 100 ul R2-4 medium plus 50 ug/ml Sm and incubated at 37° C. without shaking for approximately 18 hr. The *E. coli* HB101/pRK2013 culture was centrifuged down, washed with an equal volume of 0.9% saline to remove the Km, centrifuged down again and concentrated by resuspending in one tenth the original volume of saline. A 10 ul volume of this concentrated *E. coli* HB101/pRK2013 was added to each microtiter well containing 100 ul of 18 hr *E. coli* K802 recA− pKT230cos5:1306-3-A2 culture. 10 ul volumes of the mixed HB101/pRK2013 and K802 recA− pKT230cos5:1306-3-A2 cultures were spotted onto dry 150 mm R2-4 plates using an 8-channel pipette and in an array corresponding to the pattern of microtiter wells so that the donor of each transconjugant could be traced back to its location in the *E. coli* cosmid bank. Once the spots were dry, an additional 10 ul of each mixed culture was layered over the original spot and allowed to dry. This was repeated until 50 ul of each mixed culture was laid down. The Acetobacter 1306-24 culture was spun down and resuspended in one tenth the original volume of 0.9% saline. A 10 ul amount of this concentrated culture was layered over each HB101/pRK2013 and *E. coli* K802 recA pKT230cos5:1306-3A2 spot on the R2-4 plates with the 8-channel pipette. The spots were allowed to dry, then the conjugation mixtures were incubated at 30° C. on the R2-4 plate for 3 hr.

To determine which transconjugants produced cellulose, each of the mating mixtures was scraped from the mating plates with a sterile toothpick and inoculated directly into 2 ml R70-2 containing 0.5% TYE, 3% glucose, 25 mM DMG, 20 ug/ml Cm and 50 ug/ml Sm in 13×100 mm tubes ("test tube selection screen"). The antibiotic Cm inhibits the growth of the *E. coli* donor and helper parents. The antibiotic Sm inhibits the growth of the Acetobacter strain 1306-24 which had not received a cosmid. The tubes were incubated at 30° C. and checked for formation of pellicles at day 7 and day 14. This procedure allowed visualization of any cellulose that the transconjugants produced.

Using the multiple spot conjugation method described above for cosmid transfer and the test tube selection screen for cellulose production, 487 cosmids from the bank pKT230cos5:1306-3A2 were used in matings with the Acetobacter cellulose synthase mutant 1306-24. Of these conjugations 386 showed successful cosmid transfer. Three of these matings mixtures formed a pellicle in the standing test tube screen after 14 days incubation at 30° C. These three cosmid donor cultures were designated T19G9, T20A1, and T20B6.

None of the transconjugant colonies arising when these conjugation mixtures were directly plated, showed a Cel+ phenotype. It is only when conjugation mixtures were inoculated into standing test tubes that cellulose production could be detected. In later studies it was observed that restoration of Cel+ activity was due to recombination and not to true complementation. This might explain the need for a screen using the test tube selection, rather than relying solely on a plating protocol.

Confirmation of Restoration of Cellulose Synthase Activity in Filter Matings Cosmids T19G9, T20A1 and T20B6 whose 1306-24 transconjugants produced a pellicle in the test tube selection screen described above were further tested in transfers done by the filter conjugation method with Acetobacter 1306-24 (receipient), E. coli HB101pRK2013 (helper plasmid strain), and E. coli pKT230cos5:1306-3A2 T19G9, -T20A1, and -T2B6 (donor strains) according to the procedure in Example III.

100 ul of the mating mixtures were inoculated for a test tube selection screen. Conjugation frequency for these conjugations was determined by plating serial dilutions of the mating mixtures directly after conjugation on R20-2 plates containing 20 ug/ml Cm and 40 ug/ml Sm. As a negative control the vector pKT230cos5 was transferred to 21306-24 in parallel with these conjugations, plated and inoculated into test tubes. These 1306 24 pKT230cos5 transconjugants formed no pellicles in the standing test tube screen and served as a control to distinguish between Cel− growth and pellicle formation in standing test tubes. Of the three cosmids previously identified, only cosmid pKT230cos5 1306-3A2 T19G9 gave positive results, i.e., converted strain 1306-24 from Cel− to Cel+ in standing test tube screen. The frequency of conjugation of the cosmid T19G9 was $7.0 \times 10^{-8}$ per recipient cells.

EXAMPLE VI

Construction of Cosmids Carrying Truncated And Full-length Cellulose Synthase Gene B Conjugation between the E. coli carrying pKT230cos5T19G9 and Acetobacter 1306-24 was performed on a filter. 100 ul of the conjugation mixture was inoculated for a test tube selection screen as described above. After seven days a pellicle formed in the test tube and was blended in a blender with 25 ml of 0.9% NaCl. The resulting suspension was streaked for single colonies on an R20-2 plate containing 20 ug/ml Cm and 40 ug/ml Sm. A Cel+ colony was picked and designated 1306-24 T19G9#106. The cosmid isolated from 1306 24 T19G9#106 was 16.6 kb in length. When E. coli strains K802 recA− carrying T19G9#106 were used as the cosmid donors in a conjugation with 1306-24 as the recipient, Acetobacter transconjugants showed a Cel+ phenotype in 100% of the test tubes in the test selection screen. Therefore, the 16.6 kb cosmids were able to restore cellulose synthase activity in the Cel− mutant of 1306-24. Restriction analysis indicated that the T19G9#106 was a deletion product of T19G9. Nucleotide sequence analysis after the intact gene was cloned confirmed that cosmid T19G9#106 was carrying a truncated cellulose synthase B gene (SEQ ID No: 4) wherein the deletion site was located 142 bp 3′ from the unique BamHI site in the coding region of the gene.

In a Southern hybridization, a 1.8 kb BamHI-SmaI fragment from cosmid T19G9 strongly hybridized with the oligo probe MK172 (its sequence spans from nucleotide 4564 to 4582 in FIG. 1). If the molecular weight of the cellulose synthase B protein was not greater than 120 kd, the 1.8 kb BamHI SmaI fragment should contain the 3′-end of the B gene. To confirm this hypothesis, a plasmid carrying a full-length cellulose synthase gene was constructed in a three piece ligation as follows.

Figure 3:
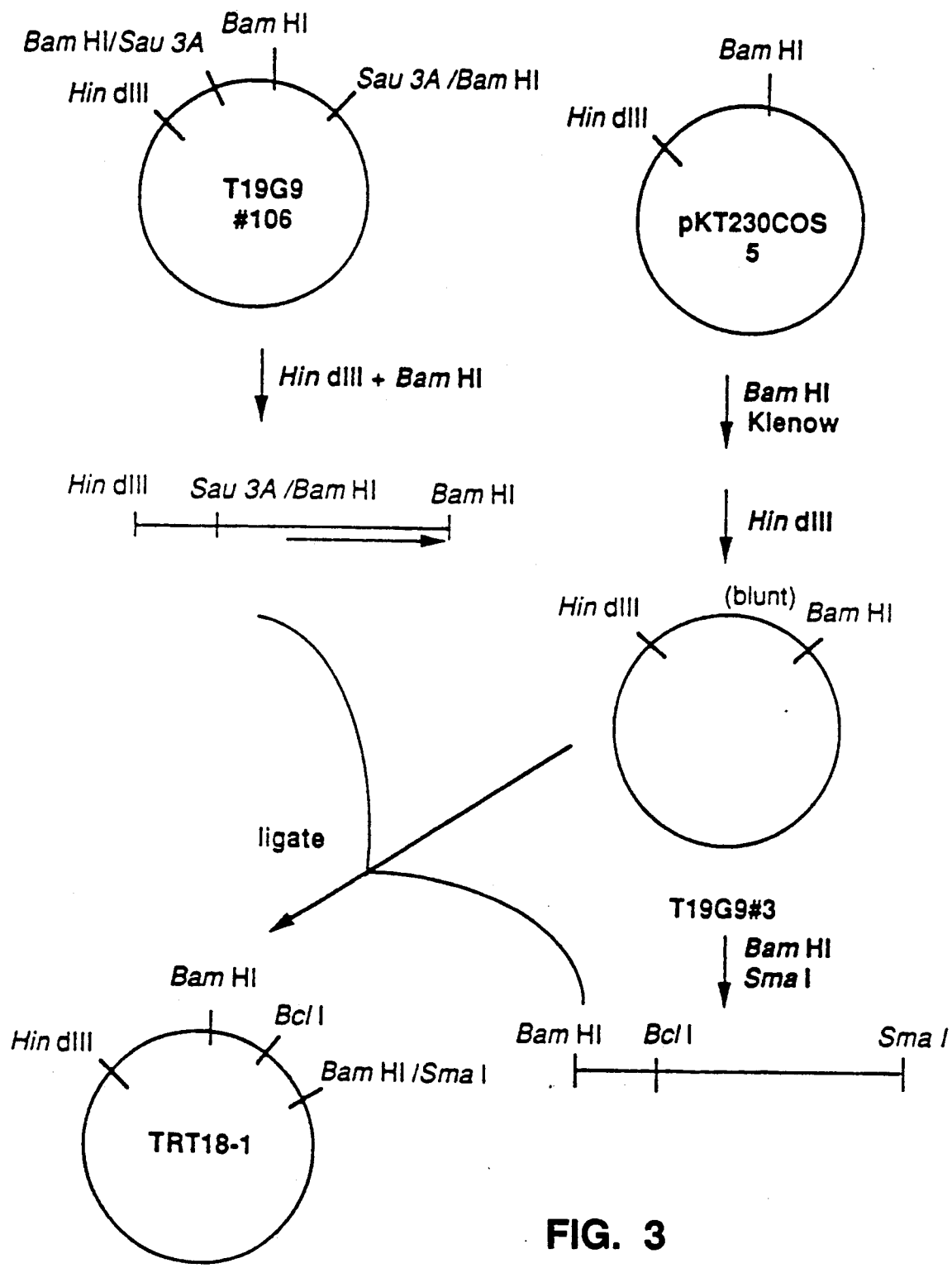
FIG. 3 is an illustration of the construction of TRT18-1 which contains the full-length cellulose synthase B gene (SEQ ID No: 4).

The cosmid vector pKT230cos5 was first digested with BamHI and the ends were repaired with the Klenow enzyme in the presence of all four deoxyribonucleotide triphosphates. The DNA was further digested with HindIII. A 3.5 kb BamHI-SmaI fragment from T19G9 containing the 3′-end of the cellulose synthase gene and the HindIII BamHI fragment from T19G9#106 carrying the 5′-end of the cellulose synthase gene were ligated into the HindIII BamHI repaired vector pKT230cos5 to construct TRT18-1. The construction for TRT18-1 is shown in FIG. 3.

EXAMPLE VII

In Vitro Cellulose Synthase Activity in Cellulose Positive Transconjugants

A 3 kb region of Acetobacter genomic DNA (cosmid T19G9#106) could restore a Cel+ phenotype to Acetobacter strain 1306-24 (Example VI). The present example describes the recovery of cellulose synthase activity in the transconjugant Acetobacter strain 1306-24. The assay used was described as the screening assay in Example II.

Controls consisted of Acetobacter strain 1306-3 (Cel+), and strain 1036-24 (Cel−) each carrying the vector pKT230cos5. The Cel+ strain 1306-24 T19G9#106 ("the transconjugant") carried a 3 kb fragment of Acetobacter genomic DNA in the vector pKT230cos5. The cells were grown as described in Example II, with addition of 50 mg/l Sm, and 20 mg/l Cm. The cells were collected, separated from cellulose, washed, brought to concentration and sonicated as previously described. In vitro cellulose synthase activity was measured and a BCA (bicinchoninic acid) protein assay developed by Pierce (Chemical Company, Rockford, Ill.) was used to measure the protein concentration of the sonicated cell preparations. Strains were assayed at a concentration of 2 mg cells/ml. Strains 1306-24 pKT230cos5 and 1306 24 T19G9#106 were also measured at 5 mg cells/ml to check for a possible concentration effect.

As shown in Table 1, the cellulose synthase activities of strains 1306-24 pKT230cos5 and the transconjugant 1306-24 were not affected by the cell concentration of the assay. The activity of 1306-3 pKT230cos5 was similar to the activity of strain 1306-21 (not shown). Thus the vector pKT230cos5 does not appear to affect the cellulose synthase activity. Strain 1306-24 demonstrated a low level of cellulose synthase activity upon activation by c-di-GMP. This was true for most Class I (cellulose synthase negative) Acetobacter mutants. Although the mutation in cellulose synthase activity appears somewhat leaky in vitro, the cells appear to make very little cellulose in vivo (in shake flasks). The 3 kb insert increased the cellulose synthase activity of strain 1306-24 roughly ten fold (0.4 to 4.1 nmole/min mg) at 5 mg cells/ml in the assay tube. This correlated with the appearance of the cellulose positive phenotype. The transconjugant strain 1306-24 had the same c-di-GMP-stimulated activity as did the cellulose positive strain 1306-3.

Results for TRT18-1, determined in a separate experiment using appropriate controls, confirmed that this plasmid was able to convert a Cel− phenotype to Cel+, and secondly, that, in the in vitro assay, the activity of the enzyme was comparable to that observed for the pKT230cos5 vectors carrying the 3 kb T19G9#106 Acetobacter DNA insert shown in Table 1.

TABLE 1

Conversion of Strain 1306-24 from Cel− to Cel+: Recovery of In vitro Cellulose Synthase Activity

| Activity Strain | Cell Concentration in assay (by Klett units mg/ml) | Cellulose Synthase (nmole UDPG consumed) (min-mg) No c-di-GMP | + c-di-GMP |
|---|---|---|---|
| 1306-3pKT230cos5 | 2 | 0 | 4.1 |
| 1306-24pKT230cos5 | 2 | 0.2 | 0.6 |
| 1306-24+insert[1] | 2 | 0.2 | 3.9 |
| 1306-24pKT230cos5 | 5 | 0.1 | 0.4 |
| 1306-24+insert[1] | 5 | 0.1 | 4.1 |

[1] pKT230cos5 with the 3 kb Ti19G9#106 Acetobacter DNA insert.

EXAMPLE VIII

The Nucleotide Sequence of The Cellulose Synthase B Gene

In this example, the restriction map of the cloned cellulose synthase B gene (SEQ ID No: 4) of the invention was used to guide the subcloning strategy for the determination of the nucleotide sequence of the cellulose synthase gene carried on cosmid T19G9#106.

The cloned insert DNA carrying the cellulose synthase gene in cosmid T19G9#106 was physically mapped using restriction enzymes. This map information was then used for subcloning the Acetobacter DNA insert into M13 RF DNA for sequencing analysis as described by Messing in *Methods in Enzymol.* 101:20-78 (1983). The nucleotide sequence of the restriction fragments was determined by the chain termination methods described in Innis, et al., (1988) *Proc. Natl. Acad. Sci. U.S.A.* 85:9436-9440, using Taq DNA polymerase (Cetus Corp., Emeryville, Calif.).

EXAMPLE IX

Cellulose Synthase Gene Disruptions And Restoration of Cellulose Synthase Activity in The Mutant Acetobacter Strain 1306-24

To determine whether cellulose synthase was expressed from the plasmid TRT18-1, three different frameshift mutations were introduced in the coding region of the cellulose synthase gene. The mutated genes were introduced into plasmid TRT18-1 which was then individually transferred into Acetobacter strain 1306-24.

Three mutations were introduced in the coding region of cellulose synthase as follows: a BglII linker sequence was introduced at the EcoRV site at nucleotide position 3113 and at the StuI site at nucleotide position 3954. The EcoRV insertion should create a termination codon TGA, as well as a frameshift mutation. The BglII linker that was introduced at a StuI site at position 4564 should create a frameshift mutation. The third mutation was introduced at the BamHI site at nucleotide position 1899 and was created by filling-in the BamHI site with Klenow.

The DNA of these plasmids was analyzed by restriction digest and verified by DNA sequencing. Each mutated gene was conjugated into the Class I mutant strain 1306-24. Single colonies from plates were picked into standing test tubes and the results of these conjugations are presented in Table 2. The ability to form a pellicle was scored in tubes directly inoculated with the conjugation mixture or with colonies from selection plates. All mutated genes were able to convert the Cel− mutation present in 1306-24 which suggests that conversion of the mutation occurred via recombination between the plasmid and the chromosome The results suggest that the chromosomal and the plasmid synthase genes recombined to form a functional copy of the gene. Presumably, transcriptional and translational signals are provided by the chromosomal copy. Qualitatively speaking, the size of the pellicles formed in all tubes were similar, suggesting that level of expression in all transconjugates was the same.

TABLE 2

Conjugation of Mutated Cellulose Synthase DNA Host 1306-24 (Class I Mutant)

| Conjugation# | Plasmid | Mutation Site | Conjugation Frequency | Standing Tube 1 (conj. mix) | Standing Tube 2 (colonies) |
|---|---|---|---|---|---|
| CRT18 | TRT 18-1 | None | $2 \times 10^{-7}$ | Cel+ (6/6) | Cel+ (10/10) |
| CRT19 | TRT 28-1 | BamHI | $4 \times 10^{-7}$ | Cel+ (6/6) | Cel+ (10/10) |
| CRT20 | TRT 29-1 | StuI | $3.5 \times 10^{-7}$ | Cel+ (6/6) | Cel+ (10/10) |
| CRT21 | TRT 30-1 | EcoRV | $2 \times 10^{-7}$ | Cel+ (6/6) | Cel+ (10/10) |

EXAMPLE X

Cloning of a 3.5 kb Endogenous Plasmid From Acetobacter Strain

Acetobacter CMCC824, a proprietary strain of Cetus Corporation, a cellulose producing strain isolated from a vinegar culture (CMCC824) contains a 3.5 kb plasmid. To isolate this plasmid, a single colony from an R20-2 plate was inoculated into 50 ml of R20-2 and grown without shaking at 30° C. for 48 hours. The pellicle was washed twice in 100 ml of 50 mM Tris, 10 mM EDTA, pH 8.0, homogenized in a Beckman blender and filtered through cheesecloth. The cells were pelleted and plasmid DNA was prepared following a modified SDS lysis procedure by Guerry, et al., (1973) *J. Bacteriol.* 116:1064.

To the cell pellet was added 1.5 ml 25% sucrose, 0.05M Tris HCl, pH 8 and the cells were gently resuspended using a Pasteur pipette and then transferred to a 12 ml polypropylene tube. After 0.15 ml lysozyme (10 mg/ml in 250 mM Tris-HCl, pH 8) were added, 0.6 ml 0.25M Na$_2$-EDTA, pH 8 was added and the tube inverted before placing on ice for 20 min.

Next, 0.6 ml of 10% SDS were added to the tube, which was inverted slowly at room temperature until clearing was observed. About 0.9 ml of 5M NaCl were added and the tube inverted until the formation of a white precipitate was observed. The tube was placed on ice at 4° C. for 2–20 hr and then the precipitate was spun down at 20,000×g for 45 min at 0°–4° C.

The supernatant was decanted and an equal volume of distilled water was added. An equal volume of twice-distilled, Tris equilibrated phenol (pH 8.0) was added and the tube gently inverted for 3–4 min before centrifugation at 20° C., 5000×g for 15 min. The aqueous layer was carefully removed using a Pasteur pipette and placed in a polypropylene tube capable of holding 2-3X of the present volume. Next, 1/10 volume of 3M NaOAC and 2-3X volumes of absolute EtOH were added and mixed well before the tubes were placed at −20° C. overnight. The supernatant was collected by centrifugation (20,000×g for 30 min at 0° C.) and the pellet washed with 5-10 ml cold 70% EtOH, and then recentrifuged at 20,000×g for 10 min to recover the pellet. The pellet was dissolved in 50-100 ul TE (100 mM Tris, 1 mM EDTA). The plasmid DNA was purified by ethidium bromide CsCl density centrifugation.

To physically map this plasmid, the CsCl prepared DNA was digested with the following restriction enzymes: HindIII, EcoRI, PstI, BamHI, SacI, PvuII. Of the enzymes tested, only SacI was able to linearize this plasmid.

Figure 4:
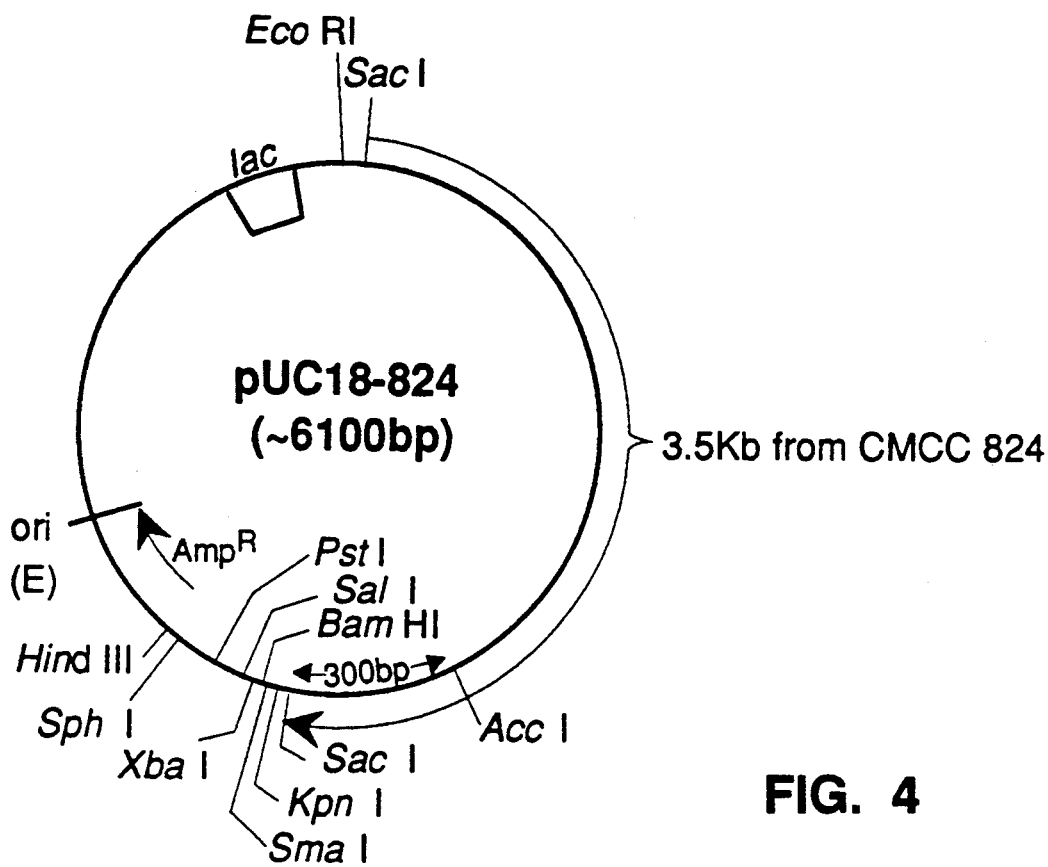
FIG. 4 is a restriction map of plasmid pUC18-824.
Figure 7:
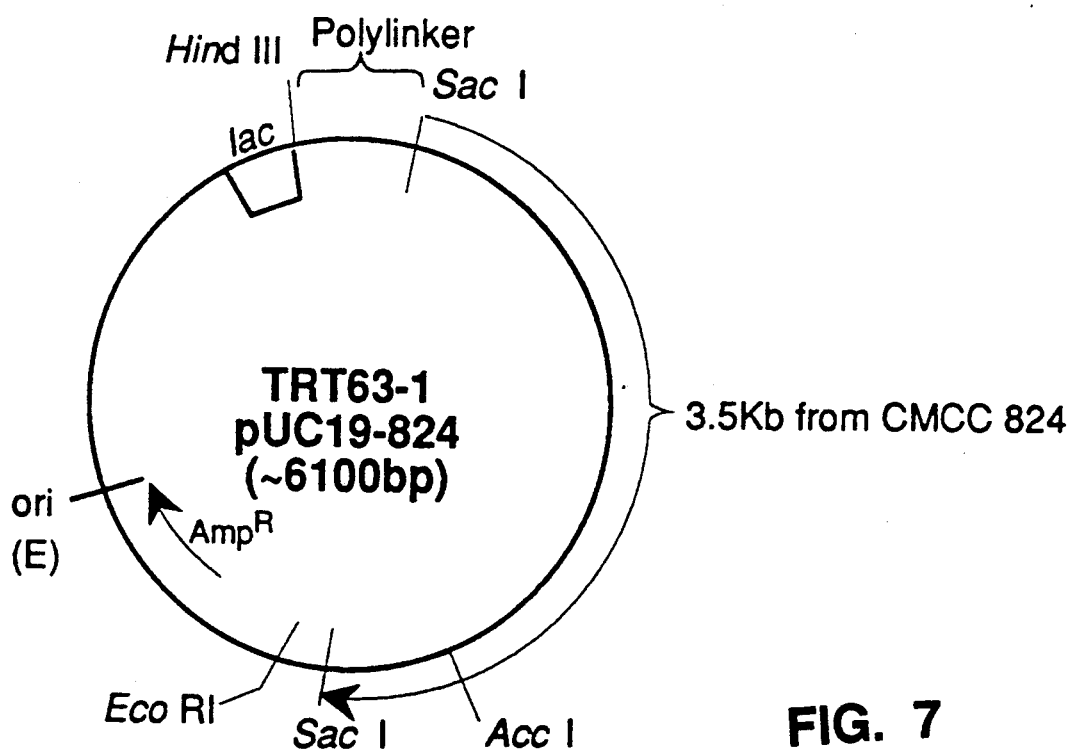
FIG. 7 is a restriction and functional map of plasmid pUC19-824.

SacI-digested plasmid was ligated to SacI-digested plasmid pUC18 (New England Biolabs) for cloning in E. coli. This shuttle vector was designated pUC18-824. In order to physically map pUC18-824, the plasmid was digested with a variety of restriction endonucleases. A restriction map of pUC18-824 is shown in FIG. 4.

EXAMPLE XI

Electrotransformation

To demonstrate that the shuttle vector pUC18-824 can be transferred to Acetobacter strains, pUC18-824 plasmid DNA was prepared from an E. coli host strain DG98, carrying pUC18-824 according to Clewell, et al., (1972) J. Bacteriol. 110:667. Acetobacter strains 1306-21 and 1306-24 were washed as described in Dower, et al., (1988) supra. An electroporation device designed for bacterial culture transformation was used for Acetobacter electroporation. While the device used in this example was a modification of a mammalian-designed electroporation device, a commercial device, such as the Bio-Rad Gene Pulser Apparatus (120v, 50/60 Hz) may be substituted to obtain equivalent transformation frequencies. The electroporation parameters were optimized with plasmid pKT230cos5T19G9#106 as follows: A field force of 9.0 KV/cm and 9.5 KV/cm was desirable for strains 1306-21 and 1306-24, respectively. A pulse duration (RC value) of 25 microfarads/750 ohms (=18.75 msec) was determined to be optimal. Upon incubation at 30° C. for an additional 5 days, greater than $10^4$ transformants per microgram of DNA were obtained on R20-2 plates containing 100 microgram/ml ampicillin.

pUC18-824 plasmid DNA was isolated from four Acetobacter candidates and transformed into E. coli and Acetobacter. The shuttle vector is stable after growth in Acetobacter since restriction analysis (of four total clones) showed the presence of all the polylinker sites and the absence of discernible deletions.

EXAMPLE XII

Construction of pUC18-824 Containing The Cellulose Synthase B Gene

The cellulose synthase B gene (SEQ ID No: 4) can be isolated from plasmid TRT18-1, the construction of which is taught at Example VI, or alternatively, since the nucleotide sequence of this gene is provided herein, the full-length gene may be directly synthesized by chemical means or may be obtained from the constructed gene bank using a primer. For example, the primer oligonucleotide MK170 (TGCCCTGGCCAGATGTCAGCA) (SEQ ID No: 7) was used to probe the 1760 individual cultures from the constructed gene bank, and six clones were isolated for further characterization. Three cosmids isolated from three of these clones were designated as T5A1, TIC2 and T5D2.

Figure 5:
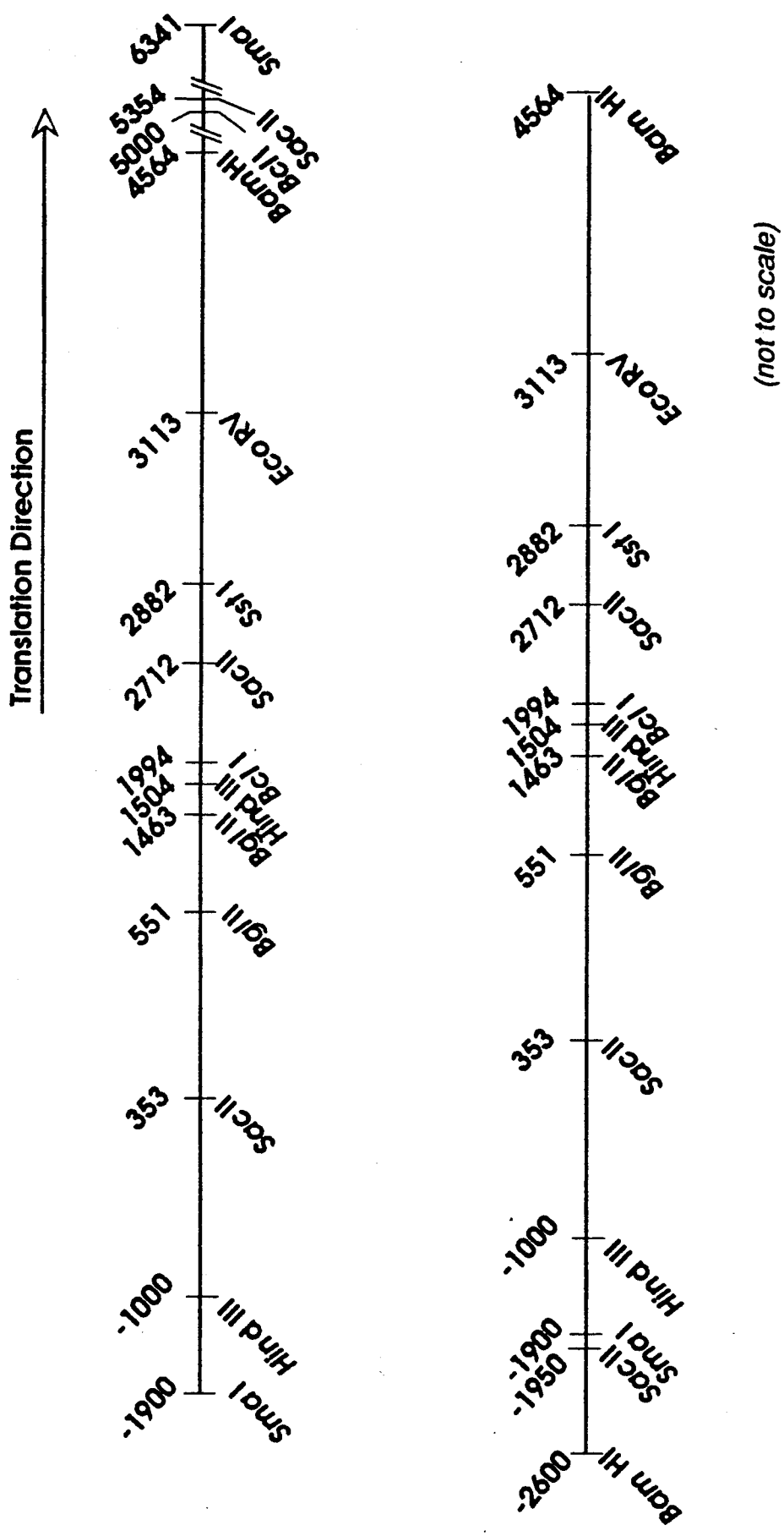
FIG. 5 is a restriction map of the 8.3 kb SmaI fragment and the 7.2 kb BamHI fragment from cosmid T5A1.

Restriction and Southern analysis of the above isolated cosmids indicated that they all carried more than 8 kb of DNA sequence 5 of the cellulose synthase B gene, as well as the entire coding sequence for the cellulose synthase B protein product. Southern analysis of the cosmid DNAs, with the primer KM170 as the probe, suggested that a 7.2 kb BamHI fragment from T5A1 carries most of the cellulose synthase B gene, as well as additional sequence immediately 5' of the gene. Therefore, the 7.2 kb BamHI fragment was subcloned in plasmids pUC18 and pBR322 for nucleotide sequence analysis. A restriction map of the 7.2 kb BamHI fragment is shown in FIG. 5. An approximately 8.3 kb SmaI fragment shown in this figure contains the intact, full-length cellulose synthase B gene. This gene was isolated from plasmid T5A1 for use in the construction with the cloning vector pUC18-824 as described below. Southern analysis also indicated that the organization of the cellulose synthase B gene locus in the chromosome is identical to that of the cosmid T5A1; therefore, the Acetobacter sequence in the cosmids has not been extensively rearranged.

Figure 6:
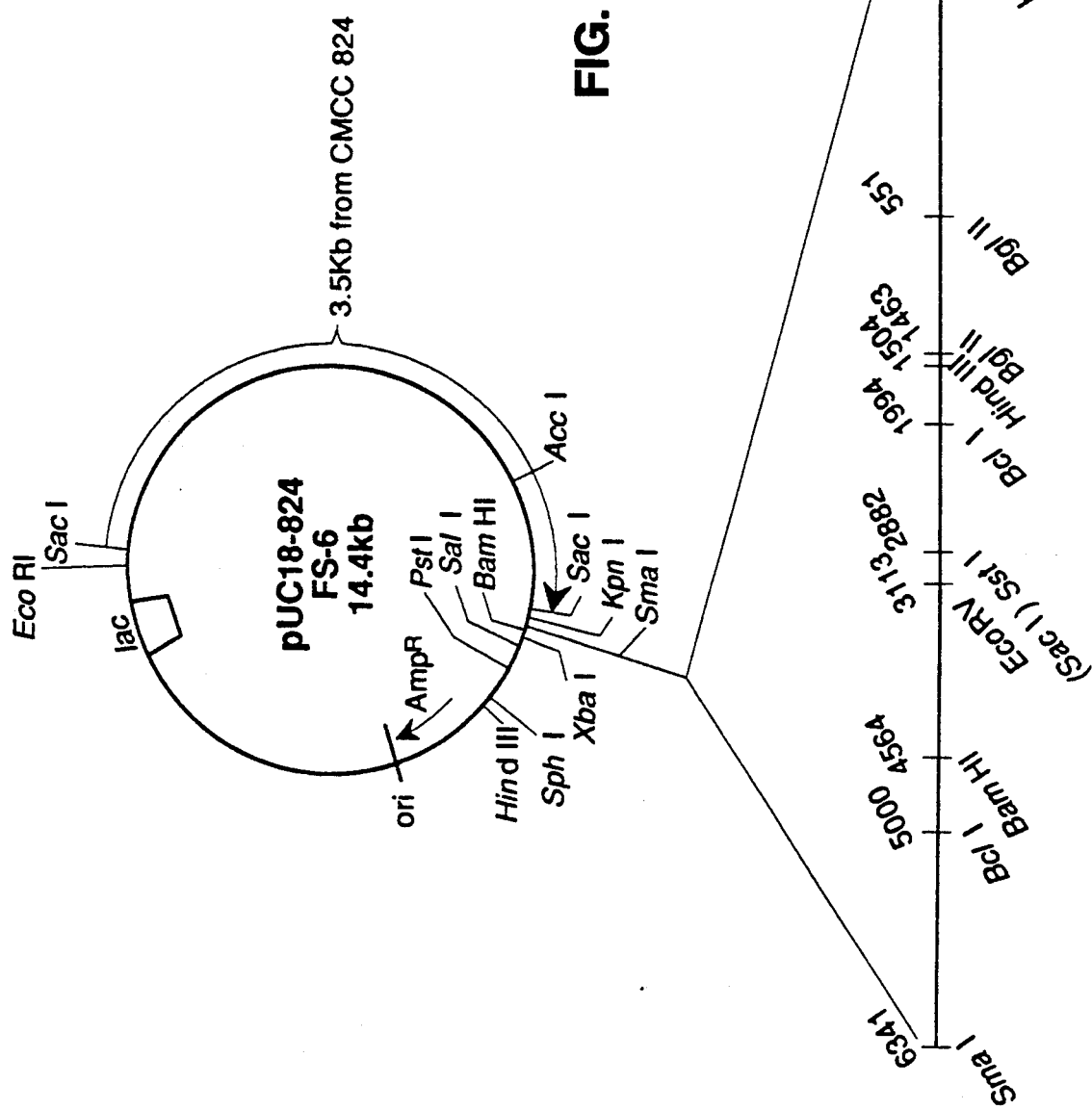
FIG. 6 is a restriction and functional map of plasmid pUC18-824 FS6; pUC18 824 FS1 is homologous to pUC18-824 FS6 except the orientation of the SmaI restriction fragment carrying the cellulose synthase gene is reversed.

The 8.3 kb SmaI fragment carrying the cellulose synthase B gene and about 3 kb upstream sequence (see the restriction map in FIG. 5) was cloned into the SmaI site of pUC18-824. The resultant plasmids carrying the opposite orientations of the 8.3 kb SmaI restriction fragment, were designated as pUC18-824 FS-1 and pUC18-824 FS-6, respectively. A restriction map of FS-6 is provided in FIG. 6. When such plasmids were transformed into 1306-24 (a cellulose synthase deficient strain), 1306-42 and C90-1 (both deficient in diguanylate cyclase and cellulose synthase activities), the transformants showed the Cel+ colony phenotype on plates. Therefore, in contrast to the "recombination events" observed in the earlier experiments, it was concluded that the protein encoded by the 8.3 kb Acetobacter DNA insert is directly capable of complementing the cellulose synthase mutations carried in the mutants.

In vitro assays confirm the ability of the plasmids pUC18-824 FS-1 and pUC18-824 FS-6 to restore cellulose synthase activity to the cellulose synthase negative mutant strain 1306-24. The in vitro cellulose synthase assay of the transformants and control strains was carried out as described in Example VII. As shown in Table 3, the transformants, 1306-24 pUC18 825 FS-1 and 1306-24 pUC18-824 FS-6 showed cellulose synthase specific activities higher than that of the original Cel parent strain, 1306-3 (1.3X and 1.8X, respectively).

TABLE 3

Conversion of Strain 1306-24 from Cel− to Cel+: Recovery of In vitro Cellulose Synthase Activity

| Strain | Cellulose Synthase Activity nmole UDPG incorporated/ (min-mq protein) | |
|---|---|---|
| | no c-di-GMP | + c-di-GMP |
| 1306-3 | 0.04 | 2.05 |
| 1306-24 | 0.06 | 0.07 |
| 1306-24 pUC18-824 | 0.06 | 0.10 |
| 1306-24 pUC18-824 FS-1 | 0.10 | 2.59 |

TABLE 3-continued

Conversion of Strain 1306-24 from Cel− to Cel+:
Recovery of In vitro Cellulose Synthase Activity

| | Cellulose Synthase Activity nmole UDPG incorporated/ (min-mg protein) | |
|---|---|---|
| Strain | no c-di-GMP | + c-di-GMP |
| 1306-24 pUC18-824 FS-6 | 0.10 | 3.71 |

EXAMPLE XIII

Construction of an Expression Vector in Acetobacter

Plasmid pUC19 (New England Biolabs) was digested with the restriction enzyme SacI. The linearized plasmid was ligated with SacI-restricted Acetobacter plasmid 824. The resultant plasmid was designated pUC19-824. The cellulose synthase gene from the 8.3 kb SmaI fragment was cloned as a HindIII-SmaI fragment (i.e., 4.9 kb) into the HindIII-SmaI sites in the linker region of the pUC19 plasmid so that its transcriptional direction was identical to the lac promoter. This construction placed the gene under the control of the lac promoter in Acetobacter. Since the lac promoter is a constitutive promoter, expression of cellulose synthase in the absence of the lacI gene product would be unregulated in Acetobacter. The plasmid was designated pAL1.

Plasmid pAL1 was used to transform Acetobacter strain 1306-24 and was shown to complement the cellulose synthase-deficient phenotype, resulting in a Cel+ phenotype on plates.

EXAMPLE XIV

Identification of The Cellulose Synthase Operon

A. Identification of Gene B in the Operon

The 7.2 kb BamHI restriction fragment, shown in FIG. 5, from the Acetobacter chromosome was identified as carrying an additional 4.6 kb nucleotide seguence upstream of the cellulose synthase B gene (SEQ ID No: 4). To investigate whether this region contains a gene involved in the biosynthesis of cellulose, the nucleotide seguence upstream of the cellulose synthase B gene was determined as follows.

The 7.2 kb BamHI restriction fragment was cloned into the BamHI site of pBR322. A 2.3 kb SacII fragment, a 0.9 kb BglII fragment and a 3.2 kb BamHI BglII fragment of the 7.2 kb BamHI fragment from the pBR322 recombinant plasmid were subcloned into the SacII or BamHI sites of the Bluescript (Stratagene) KS vector, respectively. These three subclones and the pBR322 recombinant plasmid, carrying the entire BamHI fragment, were then purified by CsCl density gradient and used as templates in the dideoxy chain termination method for nucleotide seguence analysis. The dideoxy chain termination methods were performed as previously described except that Sequenase was used to substitute for the Klenow fragment in the extension reaction.

The nucleotide seguence of the cellulose synthase operon is shown in FIG. 1. Assuming that the ATG codon at nucleotide 2594 is the initiation codon for the cellulose synthase B gene, the nucleotide seguence of the coding region of the cellulose synthase B gene spans from nucleotide 2594 to 4999. Since the mature protein starts with the alanine codon at nucleotide 2666 (see Example the cellulose synthase appears to have a 24 amino acid leader seguence. The deduced amino acid sequence of this leader peptide is functionally similar to leader peptides carried by secreted and membrane proteins from a variety of bacteria. Therefore, the cellulose synthase protein encoded by the cellulose synthase B gene may be a membrane protein.

B. Localization of the Transcriptional Initiation Site

1. RNA isolation: Acetobacter 1306-21 was grown in R70-2 medium containing 20 ug/ml Cm and 0.1% (v/v) cellulase (Genencor) at 30° C. with shaking to late log phase (O.D.600 nm=0.7). The cells were then harvested by centrifugation at 6000 rpm for 10 min at 4° C. and resuspended into 2.5 ml of NaOAc, pH 6.0 buffer containing 1 mM EDTA and 1% SDS. An equal volume of phenol/chloroform solution were added to the cell suspension and the mixture was sonicated for 15 sec. After 10 min incubation at 60° C., the mixture was centrifuged and the aqueous layer was then extracted twice more with phenol/chloroform. After the extractions, the RNA was precipitated with isopropanol and NaOAc at −70° C. overnight. The RNA was harvested by centrifugation, washed with 100% ethanol and dried before it was resuspended into 120 ul of DEPC-treated distilled water. To degrade the DNA in the RNA solution, DNaseI (Sigma) was added to 10 ug/ml and the mixture was incubated at room temperature for 20 min. The digested mixture was extracted twice with an equal volume phenol/chloroform. Then the NaOAc concentration of the aqueous layer was adjusted to 0.3M and the RNA was precipitated with an equal volume of isopropanol. The purified RNA was washed with 80% ethanol, dried and resuspended into 40 ul of DEPC treated distilled water.

2. Primer extension: The oligodeoxyribonucleotide GE13 (5'-TGCGGCGATAAGTGCACA-3') (SEQ ID No: 8) was labeled with gamma-32P ATP and T4 polynucleotide kinase. The unincorporated nucleotide was removed by ethanol precipitation. The labeled oligodeoxyribonucleotide was resuspended into 100 ul of 0.3M NaOAc solution. The specific activity of the primer was approximately $4 \times 10^6$ cpm/pmole. Labeled primer (0.02 and 0.2 pmoles) was used for primer extension analysis.

The labeled primer was mixed with 50 ug RNA. The mixed nucleic acids were coprecipitated with ethanol and then resuspended in 30 ul of hybrization buffer containing 50 mM HEPES, pH 7.5, 1 mM EDTA and 300 mM NaCl.

The hybridization reaction was carried out at 30° C. for 10 min. After hybridization, the mixture was treated with AMV reverse transcriptase. The reaction was carried out at 42° C. for 90 min, then terminated by adding 1 ul of 0.5M EDTA and 1 ul of RNase (1 mg/ml). After 30 min incubation at 37° C., the mixture was extracted with phenol/chloroform. The cDNA was precipitated, dried and resuspended in 3 ul 10 mM Tris-HCl, pH 8.0, containing 1 mM EDTA. 4 ul of formamide was added to the cDNA suspension and the mixture was boiled for 3 min before it was loaded on a DNA sequencing gel.

The primer extension analysis indicated that the transcriptional initiation site was located within the region 5' of the first gene in the cellulose synthase operon. The transcriptional initiation site of the operon is marked by a downward arrow positioned over nucleotide 235 in FIG. 1.

C. Cloning of Genes C and D

Figure 8:
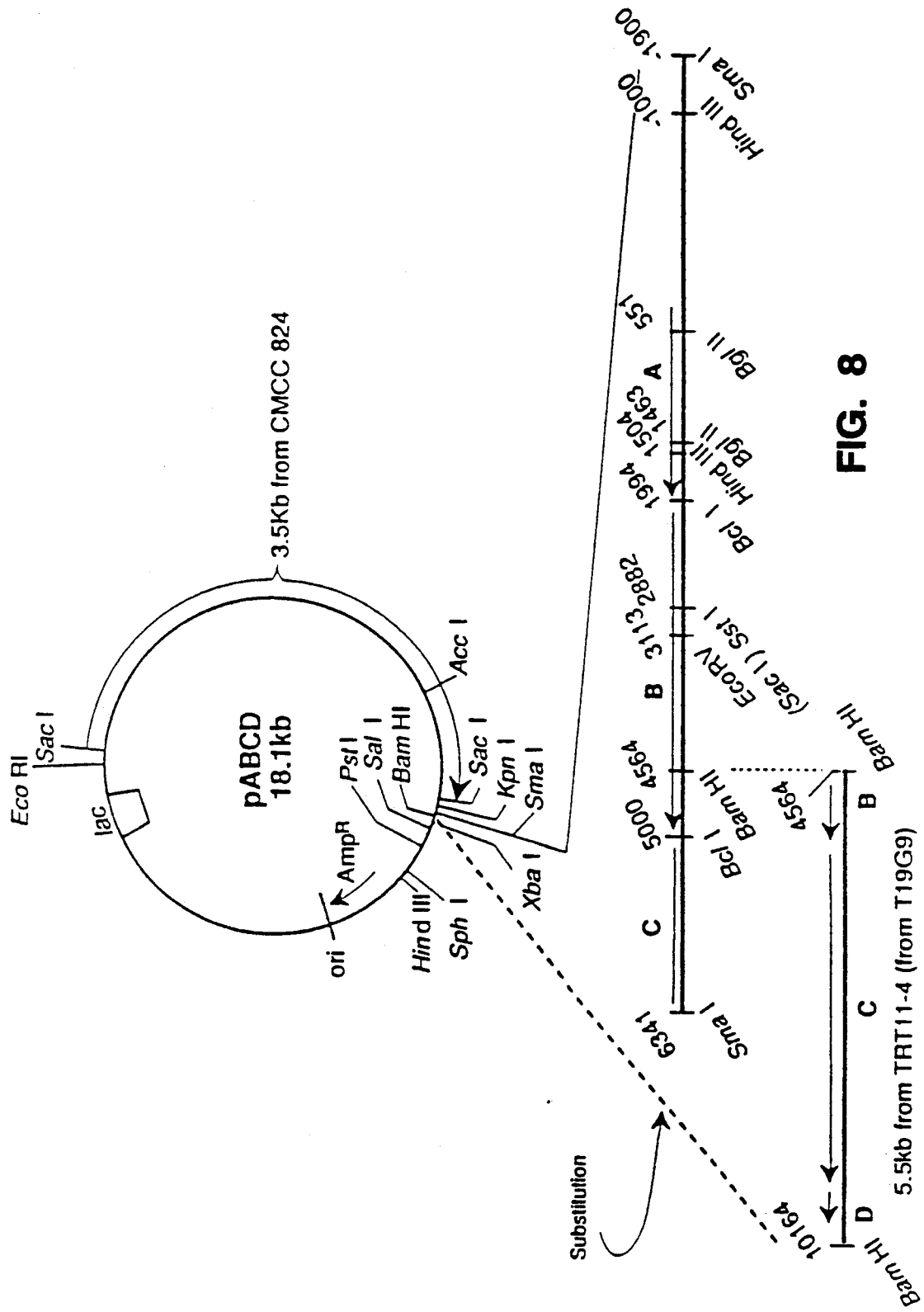
FIG. 8 schematically illustrates the construction of plasmid pABCD.

The construction of pABCD is outlined in FIG. 8. In the construction of this plasmid, a 1.8 kb BamHI fragment of pFS-6 was replaced with a 5.5 kb BamHI fragment from TRT11-4. The 1.8 kb BamHI fragment of pFS-6 carried the 3' 426 bp of the cellulose synthase B gene (SEQ ID No: 4) and approximately 1.4 kb of the C gene. The substituted 5.5 kb fragment contained the entire C gene (SEQ ID No: 5) and an additional 3' seguence. The 5.5 kb fragment carried on TRT11-4 was originally isolated from T19G9 and cloned as a 5.5 kb BamHI fragment into the BamHI site of pUC18 to construct TRT11-4.

Fifteen micrograms of TRT11-4 DNA was digested to completion with the restriction endonuclease BamHI at 37° C. for one hr. The digested DNA was run on a 0.8% GTG agarose gel. The 5.5 kb BamHI fragment was cut from the gel, electroeluted and precipitated with ethanol and resuspended in a small volume of $H_2O$.

Eleven micrograms of pFS-6 were digested to completion with BamHI at 37° C. for 1 hr, releasing 1.8 kb of DNA from the 12.6 kb vector fragment containing the 5' portion of the cellulose synthase operon. The digest was run on a 0.8% agarose gel and the 12.6 kb fragment containing the pUC18:824 vector seguence, the cellulose synthase promoter, the A gene (SEQ ID No: 3), and the 5' portion of the B gene was cut from the gel and electroeluted. The purified DNA was treated with calf intestine alkaline phosphatase and then ligated to the 5.5 kb BamHI fragment isolated from TRT11-4.

The ligation was carried out under standard conditions with a 10:1 molar ratio of 5.5 kb insert to 12.6 kb vector DNA. The ligation mixture was used to transform E. coli DG101 competent cells. The transformation mixture was plated on R2-4 plates with 50 ug/ml ampicillin and incubated at 37° C. overnight. Thirty-six ampicillin resistant transformants were picked from these plates and cultured in R2 media containing 50 ug/ml ampicillin at 37° C. with shaking for approximately 6 hr. Alkaline lysis miniscreen DNA was isolated from 36 of these transformants. The DNA was analyzed by restriction digestion with the endonucleases BamHI and SmaI. Six of the isolates showed insertion of the 5.5 kb fragment, only two of the six showed the 5.5 kb fragment in the correct orientation to restore the B gene open-reading frame. These isolates, designated pABCD #1 and #32, showed a restriction pattern corresponding to the plasmid map in FIG. 8.

Cultures containing the plasmids were used to prepare and isolate purified plasmid DNA. Ten ug of pABCD #1 DNA was used to transform 40 ul of 1306-3 cells under standard electroporation conditions. One ml of R20-2 media was added to the transformation mixture and the cells were plated on R20-2 plates containing 100 ug/ml of ampicillin. After 7 days incubation at 30° C., 547 ampicillin-resistant colonies were visible on the plates. Three hundred seventy-six colonies (approximately 69%) showed a very pointed Cel+ colony phenotype, 171 (31%) colonies showed a flatter, more warty, but still Cel+ phenotype. Four colonies of each type were streaked on R20-2 with ampicillin at 100 ug/ml and incubated at 30° C. for 4 days. After 4 days the colony types on all 8 plates were indistinguishable. One colony from the streak of a small pointed colony was picked into 25 ml R70-2 with 0.5% TYE, 3% glucose, 25 mM DMG, 0.1% and 50 ug/ml ampicillin and incubated at 30° C. with shaking for 24 hr. After 24 hr, glycerol was added to the culture to 15% of total volume and 1.5 ml aliquots were frozen for storage at −70° C. This stock was designated 1306-3 pABCD.

D. Seguence and Structure of the Cellulose Synthase Operon

The chain termination method was used to sequence the cellulose synthase operon. Double stranded DNA carrying the operon was used as the DNA template. The nucleotide seguence of the region from pABCD is shown in FIG. 1. The cellulose synthase operon is 9217 bp in length and consists of four genes. Genes A (SEQ ID No: 3), B (SEQ ID No: 4), C (SEQ ID No: 5) and D (SEQ ID No: 6) are 2,262 bp, 2,406 bp, 3,957 bp and 468 bp in length, respectively. The molecular weights determined by and suggested roles of the gene products A, B, C and D are as follows:

| Gene Product | Amino Acid Residues | Molecular Weight | Associated Function |
| --- | --- | --- | --- |
| A | 754 | 84 kd | Cellulose synthesis in vivo; diguanylate cyclase and cellulose synthase in vitro activities |
| B | 802 | 85 kd | Cellulose synthesis in vivo; cellulose synthase in vitro activity |
| C | 1319 | 141 kd | Cellulose synthesis in vivo |
| D | 156 | 17 kd | Cellulose synthesis in vivo |

Computer analysis of the DNA sequences downstream of the 3' end of the D gene revealed a region with the potential of forming a stable stem and loop structure. As shown in FIG. 1 by the underlined section, this region is positioned 26 bp 3' of the termination codon of the D gene and corresponds to a transcription terminator region of the

EXAMPLE XV

Cell Growth, Cellulose Production and Cellulose Synthase Activity in Recombinant Strains

A. Studies With 1306-21 pUC18-824 pABCD

In this study, overexpression of cellulose synthase activity in 1306-21 pABCD was tested in shake flask experiments. The construction of 1306-21 pABCD was similar to the construction of 1306-3 pABCD (See Example XIV). Culture medium for all stages of the experiment was R70-2 with 10 uM $FeCl_3$, 1% TYE, 25 mM DMG, and 4% glucose (1306-21) or 4% fructose (1306-3). The seed medium contained 0.1% cellulase. Ampicillin was added at 50 ug/ml to medium used for growing plasmid containing cultures. Medium was dispensed into 125 ml baffled flasks, with 25 ml per flask. Strains 1306-21, 1306-21 pUC18-824 (the host strain plus the shuttle vector), 1306-21 pUC18-824 pABCD (normal—the phenotype like parent), and 1306-21 pUC18-824 pABCD (spired—its growth on plates was raised and more tapered than the parent) were individually tested. Each culture was adjusted to 0.72 g/L (turbidity 1.8 OD680) using sterile saline. Test flasks were inoculated with 0.2 ml of seed culture (2% v/v inoculum). Six flasks of each strain were inoculated and incubated at 30° C., 125 rpm, 2 inch throw. Flasks were harvested after one, two, and five days. Duplicate flasks were harvested at each time point for cell mass and cellulose measurements. In addition, cultures from the five day flasks were checked for plasmid retention, by observing antibiotic resistance on plates (patch test). Thirty colonies were tested for each strain.

To measure cellulose production and cell concentration, the flask contents of each sample were transferred to a 100 ml beaker. The suspension was then macerated for one minute with a large Tekmar probe at 50% full power. After that the suspension was centrifuged at 5,000 rpm for 10 minutes. The supernatant was discarded and the pellet was resuspended in 15 ml saline solution and incubated for 15 minutes with occasional stirring. The sample was again centrifuged and the above wash step repeated.

The pellet from the second wash step was resuspended in 15 ml of 0.1N of NaOH and incubated at 60° C. with mild agitation for 60 minutes. The suspension was centrifuged and the NaOH supernatant was used to analyze cell concentration while the pellet was used to analyze cellulose concentration.

The pellet was resuspended in 15 ml deionized water and left at room temperature for 15 minutes with occasional stirring. Then the sample was centrifuged and the above wash procedure was repeated for a total of three times. After the last centrifugation step, the cellulose precipitate was dried at 60° C. overnight in a vacuum oven and then weighed.

The supernatant was neutralized with HCl (approximately 0.05 ml HCl to 0.5 ml sample) and the protein concentration was assayed by the Lowry method. Cell concentration = protein concentration × 1.54.

Cell growth and cellulose production are summarized in Table 4.

TABLE 4

Cell Growth and Cellulose Production

|  | Cellulose g/L | | Cells g/L | | Cellulose/ Cells |
|---|---|---|---|---|---|
| 1306-21 | — | | — | | — |
|  | x | s | x | s | x |
| day 1 | 1.78 | ±0.006 | 0.51 | ±0.03 | 3.52 |
| day 2 | 4.58 | ±0.32 | 1.16 | ±0.02 | 3.95 |
| day 5 | 6.99 | ±0.16 | 2.92 | ±0.15 | 2.40 |
| 1306-21 pUC18-824 | | | | | |
| day 1 | 0.91 | ±0.01 | 0.14 | ±0.06 | 6.54 |
| day 2 | 3.59 | ±0.21 | 0.92 | ±0.08 | 3.91 |
| day 5 | 6.89 | ±0.01 | 3.07 | ±0.06 | 2.24 |
| 1306-21 pABCD (spired) | | | | | |
| day 1 | 1.16 | ±0.12 | 0.14 | ±0.04 | 8.42 |
| day 2 | 4.78 | ±0.05 | 0.72 | ±0.04 | 6.65 |
| day 5 | 7.59 | ±0.07 | 2.59 | ±0.04 | 2.93 |
| 1306-21 pABCD (normal) | | | | | |
| day 1 | 1.06 | ±0.06 | 0.14 | ±0.01 | 7.41 |
| day 2 | 4.40 | ±0.28 | 0.76 | ±0.05 | 5.82 |
| day 5 | 7.28 | ±0.10 | 2.81 | ±0.01 | 2.59 |
| 1306-3 | | | | | |
| day 1 | 1.87 | ±.17 | 1.38 | ±.11 | 1.36 ± .01 |
| day 2 | 2.67 | ±.21 | 2.11 | ±.11 | 1.27 ± .04 |
| day 5 | 3.02 | ±.01 | 2.82 | ±.19 | 0.96 ± .09 |
| 1306-3 pUC18-824 | | | | | |
| day 1 | 1.56 | ±.01 | 1.26 | ±.11 | 1.24 ± .10 |
| day 2 | 2.39 | ±.04 | 2.25 | ±.42 | 1.08 ± .18 |
| day 5 | 3.88 | ±.01 | 3.70 | ±.17 | 1.05 ± .05 |
| 1306-3 pABCD | | | | | |
| day 1 | 2.92 | ±.11 | 1.20 | ±.04 | 2.44 ± .18 |
| day 2 | 3.90 | ±.01 | 2.45 | ±.03 | 1.59 ± .01 |
| day 5 | 3.66 | ±.13 | 2.97 | ±.07 | 1.24 ± .08 |

Cellulose to cell ratio is an indicator for cellulose specific productivity. In the first two days of growth the cellulose to cell ratio in 1306-21 pABCD strains is significantly higher than those of the control 1306-21 strains. The pABCD (spired strain) seems to produce more cellulose than the pABCD (normal) strains. Both recombinant strains produce more cellulose than the control strains at the end of growth.

Hundred percent retention of ampicillin resistance was retained in the recombinant strains of 1306 21 and 1306-3 after 5 days of incubation as revealed by colony patch test.

Cellulose production with 1306-3 pUC18-824 pABCD was higher than the 1306-3 and 1306-3 pUC19-824 control strains. This was correlated with an increase in the in vitro activity of cellulose synthase (see below). Cell growth with the two strains was similar. Consequently the cellulose to cell ratio with 1306-3 pUC18-824 pABCD was also significantly higher than that of 1306-3 alone.

TABLE 5

| Strain | Cellulose Synthase Activity nmoles/(min*mg protein) | | |
|---|---|---|---|
|  | Day 1 | Day 2 | Day 5 |
| 1306-3 | 2.3 | 0.7 | 0.3 |
| 1306-3 pUC18-824 | 1.2 | 0.6 | 0.3 |
| 1306-3 pUC18-824 pABCD | 3.5 | 2.3 | 0.3 |

Two parallel runs with 1306-21 pABCD were conducted in 14L SG-14 Chemap fermentors with and without addition of acetate as a co-substrate. These runs were compared to two similar runs of 1306-21 with and without acetate as a co-substrate. The results showed that strain 1306-21 pABCD has higher cellulose yield and higher cellulose to cell ration than 1306-21, and that addition of acetate as a co-substrate diminished this difference.

The seed was grown up from frozen vials on R70-3 media (R70-2 media except the final concentration of $FeCl_3$ is 0.05 mM), 25 mM DMG pH 5.0, 0.5% TYE, 30 g/L glucose, 1 g/L Na Acetate, and 0.1% cellulase. Wide mouth Fernbach flasks were used with 500 ml medium. The incubation was for 24 hr at 250 rpm.

Two identical SG-14 fermentors, each equipped with two Lightnin A315 impellers, were used. The medium was R70-3 with 1 g/L Floxan EA1340, sterilized together with CSL (type E801A). The agitation was started at 400 rpm, and ramped up manually to maintain good bulk mixing. In the control fermentor, the pH was maintained in the normal way, with sulfuric acid and ammonium hydroxide. In the co-substrate fermentor, the pH was controlled on the acid side with a mixture of acetic acid and glucose (500 ml glacial acetic + 1000 ml 50% glucose). The pH in the acetic acid run was actually controlled at 5.1, due to deadband in the pH controller, which was set at 0.1 units, while the pH in the control run was 5.1 while sulfuric acid was being added, and 5.0 while ammonium hydroxide was being added. Glucose, acetate, and ammonia levels were monitored during the run, and supplemental ammonium acetate or ammonium sulfate was added to maintain the residual levels within the desired ranges. Approximately 1 g/L ammonium acetate was added at 29.4 and 46.5 hr, and 5 mM ammonium sulfate was added at 31.4 hr. Both fermentors were run at 32° C.

The pH was uncontrolled for the first 15.5 hr of the acetate run due to operator error; no acetate was fed during this time, and the pH had risen to 5.65 by the time the problem was corrected. A comparison of the 15.5 hr data indicates this had very little effect on the run. There were no other technical problems in these runs.

Manual additions of ammonium acetate were made at 29 hr (0.8 g/L), 41.2 hr (0.5 g/L) and 47.7 hr (1 g/L), and additional ammonium sulfate (5 mM) was added at 29 hr, all to the acetate run, in order to maintain the residual levels of acetate, glucose, and ammonia within reasonable bounds. This was largely achieved, up to about 46 hr, after which it became difficult to maintain residual acetate above 0.1 g/L by these methods.

Figure 10A:
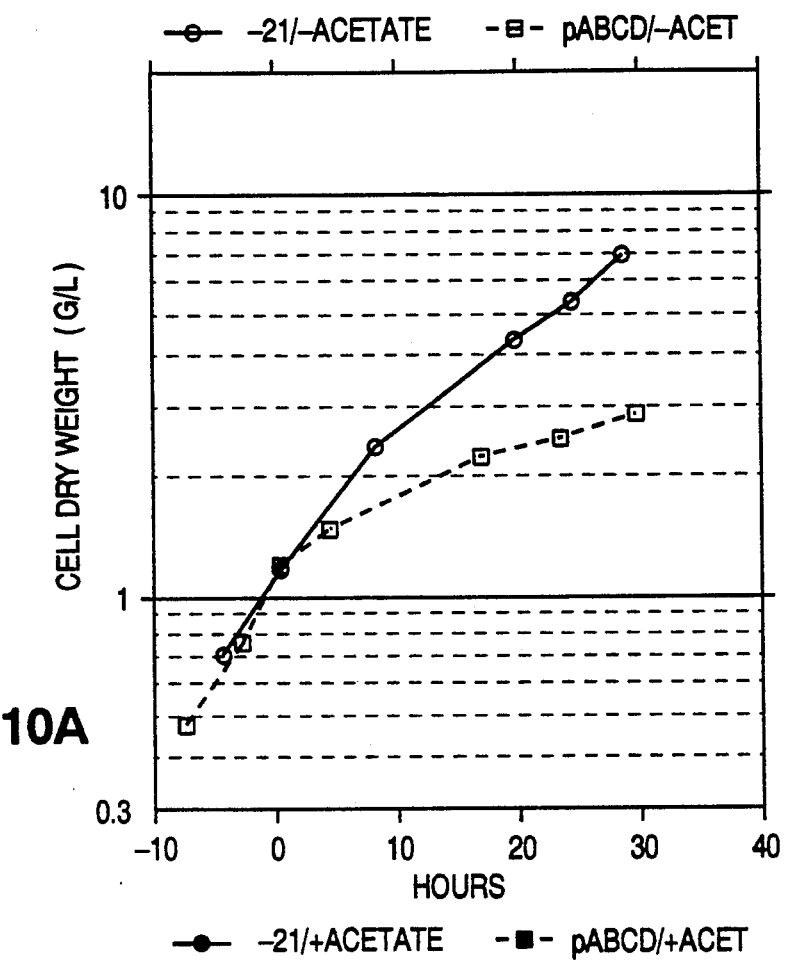
Figure 10B:
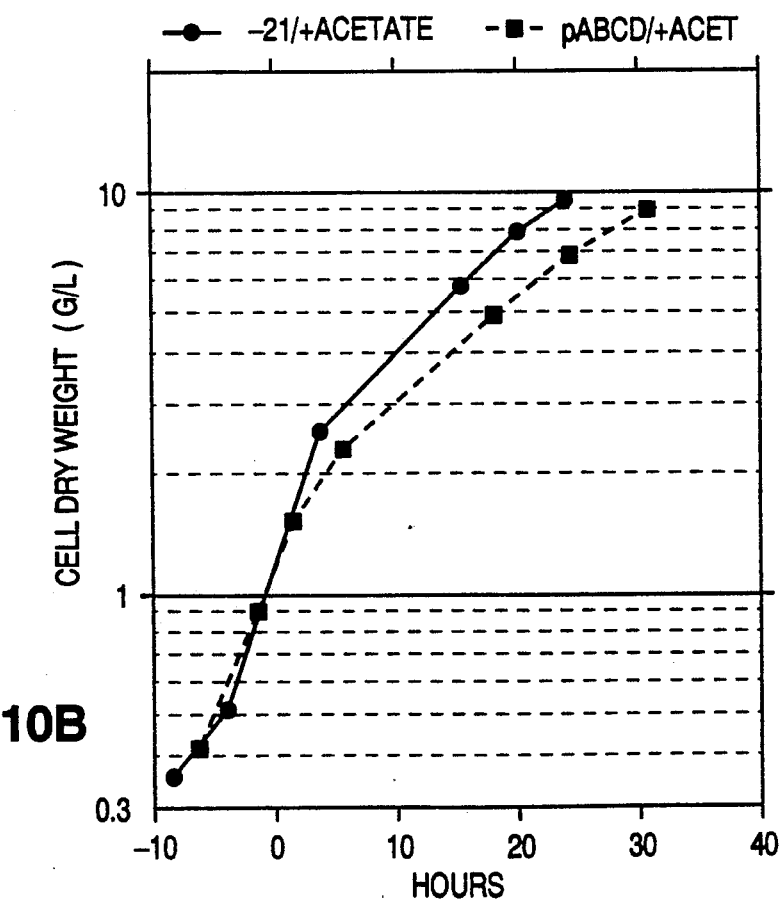
FIG. 10B illustrates the rate of cell growth of the same recombinant strain and control in the presence of acetate.
Figure 11A:
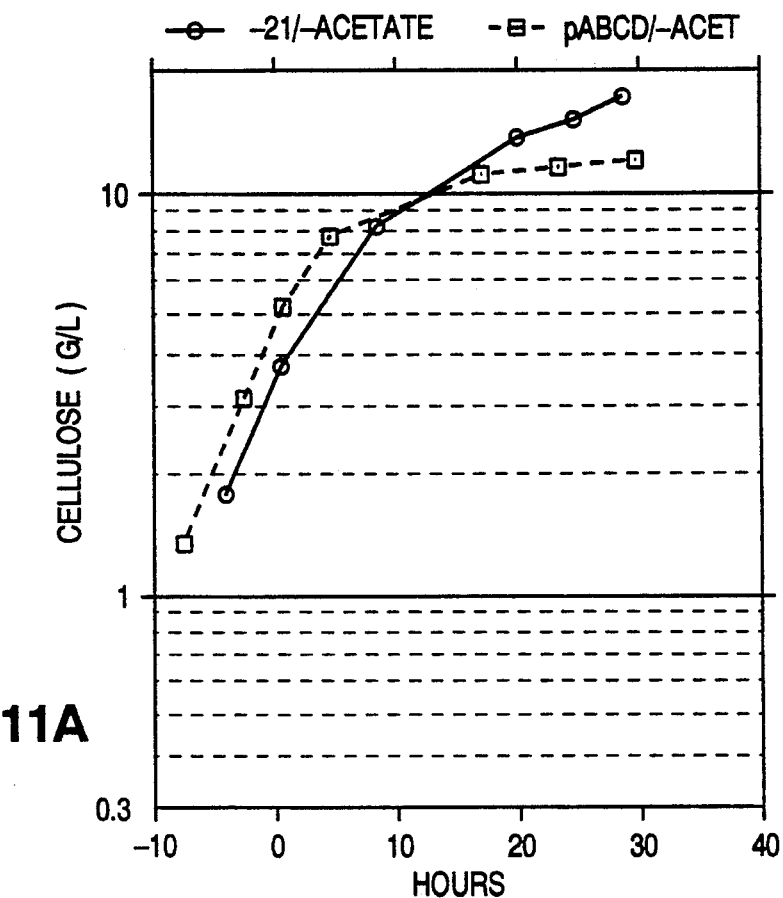
Figure 11B:
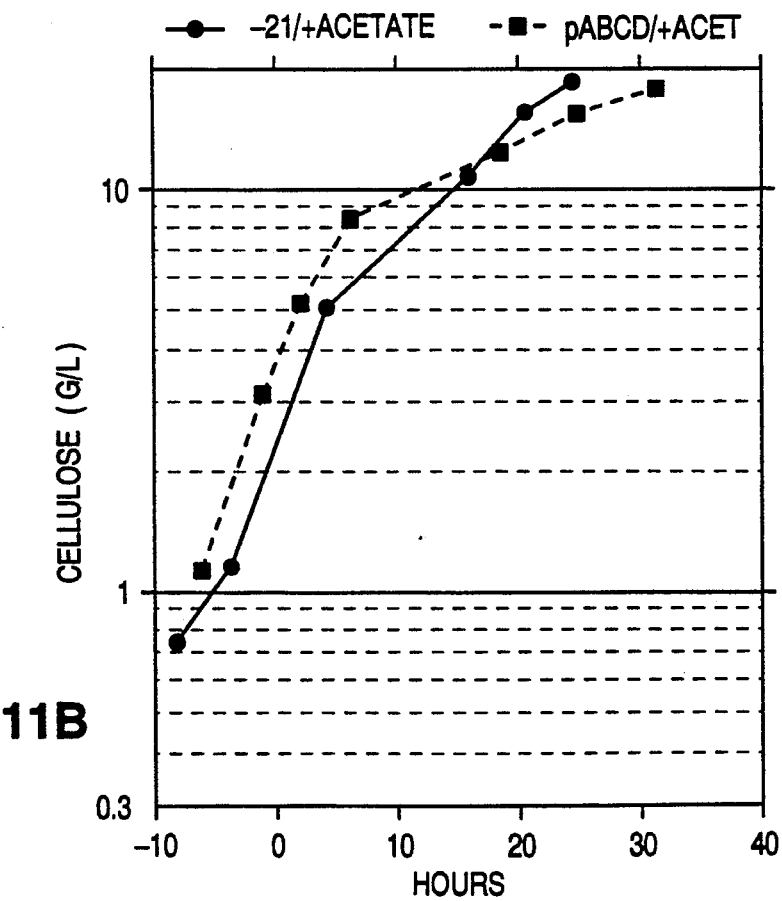
FIG. 11B illustrates the rate of cellulose produced from the same recombinant strain and control grown in the presence of acetate.

Tables 6 and 7 summarize the fermentation results for 1306-21 pABCD with and without acetate, respectively. Tables 8 and 9 summarize a similar study for 1306-21 FIGS. 10A and 10B compare cell growth for strains 1306-21 pABCD and 1306-21 without acetate addition. FIGS. 11A and 11B do a similar comparison with acetate addition. The time axes of the cell and cellulose curves have been shifted so that cell curves overlap at 1.13 g/L.

TABLE 6

SUMMARY OF FERMENTATION WITH 1306-21 pABCD SG14 Fermentor + Floxan, Lightnin Impellers AT 32° C.

| Time (hr) | Cellulose (g/l) | Cells (g/l) | Glc Used (g/l) | Yield[1] (g/g) | Corr. Yield[2] (g/g) | Cel/Cell (g/g) |
|---|---|---|---|---|---|---|
| 0.0 | 0.00 | 0.026 | 0.0 | | | |
| 15.5 | 1.36 | 0.48 | 1.7 | 0.80 | 0.84 | 2.83 |
| 20.5 | 3.12 | 0.76 | 4.6 | 0.68 | 0.71 | 4.11 |
| 23.6 | 5.20 | 1.20 | 7.4 | 0.70 | 0.73 | 4.33 |
| 27.6 | 7.81 | 1.48 | 12.8 | 0.61 | 0.63 | 5.28 |
| 40.0 | 11.15 | 2.24 | 24.8 | 0.45 | 0.45 | 4.98 |
| 46.4 | 11.60 | 2.49 | 29.1 | 0.40 | 0.41 | 4.66 |
| 52.7 | 12.00 | 2.89 | 33.5 | 0.36 | 0.37 | 4.15 |

RPM INCREASES:
400 TO 500 AT 21.5 HR; 500 TO 600 AT 22.8 HR
600 TO 700 AT 28.6 HR; 700 TO 800 AT 29.0 HR

[1] All yield values are based on glucose plus lactic acid consumed. Yield is defined as the change in cellulose concentration (g/L) divided by the substrate utilized (g/L). The amount of substrate utilized can be measured between any two substrates.
[2] The corrected yield is the cellulose yield which has been corrected for substrated and/or product which were added or removed during fermentation. A volume correction is also added into the calculation of corrected yield.

TABLE 7

SUMMARY OF FERMENTATION WITH 1306-21 pABCD Glucose + Acetate + Floxan 1 g/l SG-14 + Lightnin Impellers AT 32° C.

| Time (hr) | Res. NH3 (mM) | Acetate (g/l) | Cellulose (g/l) | Cells (g/l) | Glc Used (g/l) | Acet. Used (g/l) | Yield[1] (g/g) | Yield[2] (g/g) | Cel/Cell (g/g) |
|---|---|---|---|---|---|---|---|---|---|
| 0.0 | 30.7 | 0.00 | | 0.03 | 0.0 | 0.0 | | | |
| 15.5 | 30.2 | 0.56 | 1.12 | 0.42 | 1.3 | 0.1 | 0.78 | 0.81 | 2.67 |
| 20.5 | 27.0 | 1.69 | 3.13 | 0.92 | 5.1 | 1.4 | 0.48 | 0.49 | 3.40 |
| 23.6 | 24.7 | 2.50 | 5.22 | 1.54 | 7.9 | 3.0 | 0.48 | 0.48 | 3.39 |
| 27.6 | 20.6 | 2.22 | 8.45 | 2.30 | 14.2 | 7.1 | 0.40 | 0.39 | 3.67 |
| 40.0 | 24.9 | 1.07 | 12.20 | 4.92 | 33.3 | 18.5 | 0.24 | 0.24 | 2.48 |
| 46.4 | 15.7 | 0.07 | 15.20 | 6.90 | 45.6 | 24.0 | 0.22 | 0.23 | 2.20 |
| 52.8 | 13.1 | 0.05 | 17.75 | 9.01 | 46.5 | 51.5 | 0.18 | 0.21 | 1.97 |

SPECIAL NOTES:
NO ACETATE FED FOR FIRST 15.5 HR; pH UP TO 5.65 YIELD AND CORRECTED YIELD BASED ON GLUCOSE + ACETATE
RPM INCREASES:
400 TO 600 AT 21.5 HR; 600 to 700 AT 23.2 HR
700 TO 800 AT 27.6 HR
[1] and [2] See Legend to Table 6.

TABLE 8

SUMMARY OF FERMENTATION WITH 1306-21 SG14 Fermentor + Floxan, Lightnin Impellers AT 32° C.

| Time (hr) | Cellulose (g/l) | Cells (g/l) | Glc Used (g/l) | Yield[1] (g/g) | Corr. Yield[2] (g/g) | Cel/Cell (g/g) |
|---|---|---|---|---|---|---|
| 0.0 | 0.00 | 0.018 | 0.0 | | | |
| 17.0 | 1.79 | 0.71 | 2.9 | 0.62 | 0.63 | 2.52 |
| 21.5 | 3.74 | 1.15 | 6.6 | 0.57 | 0.58 | 3.25 |
| 29.4 | 8.30 | 2.36 | 19.7 | 0.42 | 0.45 | 3.52 |
| 41.0 | 13.70 | 4.35 | 39.5 | 0.35 | 0.37 | 3.15 |
| 45.7 | 15.00 | 5.43 | 48.1 | 0.31 | 0.34 | 2.76 |
| 49.7 | 17.15 | 6.93 | 59.8 | 0.29 | 0.31 | 2.47 |

RPM INCREASES:
400 TO 500 AT 21.5 HR; 500 TO 600 AT 23.0 HR
600 TO 700 AT 29.4 HR; 700 TO 800 AT 31.5 HR
[1] and [2] See Legend to Table 6.

TABLE 9

SUMMARY OF FERMENTATION WITH 1306-21 Glucose + Acetate + Floxan 1 g/l SG-014 + LIGHTNIN IMPELLERS AT 32+ C.

| Time (hr) | Acetate (g/l) | Cellulose (g/l) | Cells (g/l) | Glc Used (g/l) | Acet. Used (g/l) | Yield[1] (g/g) | Yield[2] (g/g) | Cel/Cell (g/g) |
|---|---|---|---|---|---|---|---|---|
| 0.0 | 0.11 | | 0.02 | 0.0 | 0.0 | | | |
| 17.0 | 0.40 | 0.75 | 0.36 | 1.7 | 0.3 | | | 2.08 |
| 21.5 | 1.06 | 1.15 | 0.52 | 3.6 | 1.4 | 0.23 | 0.25 | 2.21 |
| 29.4 | 2.25 | 5.08 | 2.55 | 9.7 | 6.7 | 0.31 | 0.36 | 1.99 |
| 41.0 | 1.07 | 10.70 | 5.85 | 29.4 | 20.4 | 0.21 | 0.24 | 1.83 |
| 45.7 | 0.11 | 15.45 | 7.93 | 42.7 | 24.1 | 0.23 | 0.25 | 1.95 |

TABLE 9-continued
SUMMARY OF FERMENTATION WITH 1306-21
Glucose + Acetate + Floxan 1 g/l
SG-014 + LIGHTNIN IMPELLERS AT 32+ C.

| Time (hr) | Acetate (g/l) | Cellulose (g/l) | Cells (g/l) | Glc Used (g/l) | Acet. Used (g/l) | Yield[1] (g/g) | Yield[2] (g/g) | Cel/Cell (g/g) |
|---|---|---|---|---|---|---|---|---|
| 49.7 | 0.65 | 18.55 | 9.60 | 59.2 | 26.7 | 0.22 | 0.24 | 1.93 |

SPECIAL NOTES:
0% DISSOLVED OXYGEN FROM 11 TO 17 RH YIELD AND CORRECTED YIELD BASED ON GLUCOSE + ACETATE
RPM INCREASES:
400 TO 500 AT 25.4 Hr; 500 TO 700 AT 29.4 HR
700 TO 800 AT 31.5 HR
[1] and [2] See Legend to Table 6.

Growth of the recombinant strain was slowed down considerably above 1 g/L cells and actually ceased at approximately 3 g/L. Addition of acetate as a co substrate stimulated cell growth and allowed growth up to 9 g/L. However in both cases and especially without acetate, the growth of the parent strain was faster than the recombinant strain at cell concentrations above approximately 1 g/L. Production of cellulose was enhanced by the addition of acetate and reached higher concentrations (18 versus 12 g/L, respectively). Cellulose yield and cellulose to cell ratio were significantly higher in the recombinant strain in comparison to the non-recombinant strain on medium without acetate throughout the entire fermentation. Addition of acetate as a co-substrate decrease cellulose yield and cellulose to cell ratio in both strains and reduced the differences that was observed between 1306-21 pABCD and 1306-21.

B. Studies with pUC18-824 FS6 (AB)

Fifteen isolates of 1306-3 (Cel+) carrying pUC18-824 FS6 (which carries the cellulose synthase promoter and genes A and B) were used to screen for overexpression of cellulose synthase activity. The cells were collected, washed, suspended and broken, and the standard in vitro cellulose synthase assay was carried out as described in Example II.

All of the fifteen isolates demonstrated in vitro cellulose synthase activity significantly in excess of that of the control strain (1306-3 pUC18:824). The activities range from 1.5 to 2.4x higher than the control strain. Two of the fifteen strains screened (#302 and #303) were examined at exponential and stationary phases. The conditions were similar to that described in Example XV except that glucose was replaced with fructose. As shown in Table 10, at day 2 the activities of the control strains 1306-3 and 1306-3 pUC18-824 retained 30% and 40% of the day 1 activity, with declining activity over time. At day 2 isolates #302 and #303 showed a decline to 45% and 50% of the day 1 activity, also with declining activity over time. However, these latter strains both showed about 2x higher activity than did 1306-3 at day 1, while the activities were about 3x higher at day 2.

TABLE 10

| Strain | Cellulose Synthase Activity nmoles/(min*mg protein) | | |
|---|---|---|---|
| | Day 1 | Day 2 | Day 5 |
| 1306-3 | 5.5 | 1.7 | 0.5 |
| 1306-3 pUC18-824 | 5.9 | 2.4 | 0.3 |
| 1306-3 pUC18-824 FS6 302 | 12.5 | 5.6 | 0.9 |
| 1306-3 pUC18-824 FS6 303 | 11.0 | 5.4 | 1.3 |

Cellulose production in these recombinant strains was similar to that observed for the parent strains It was also observed that cellulose synthase activity was suppressed in strains carrying a disrupted cellulose synthase B gene (SEQ ID No: 4). This gene was disrupted through the insertion of a 1.1 kb BamHI fragment encoding the streptomycin resistance gene at the internal BamHI site of the cellulose synthase B gene. The insertion of the streptomycin resistance gene interrupted the cellulose synthase B gene near its 5' end.

EXAMPLE XVI

Chromosomal Promoter Replacement

Acetobacter appears to have a very efficient recombination system which may cause instability problems with any plasmid carrying a large segment of autonomous DNA. To overcome this potential problem, the operon can be overexpressed at the chromosomal level using heterologous control elements to drive transcription of the chromosomal cellulose synthase operon. The construction of plasmids pTac25-1, pLac21-7 containing heterologous promoters and the intermediate vectors used for their construction is described as follows and presented schematically in FIG. 14.

A. Construction of MP11:Pcs:LF01

Fifteen micrograms of pFS-1 DNA were digested with HindIII, releasing a 2.5 kb fragment carrying the cellulose synthase operon promoter. The digest was run on a 0.8% GTG agarose gel, the 2.5 kb fragment carrying the promoter was cut from the gel, electroeluted and ligated to double stranded M13 MP phage DNA, which had previously been digested with HindIII. The ligation mixture was used to transform E. coli strain DG98. The transformed cells were plated on R17-3 plates with lawns of E. coli JM103 and incubated at 37° C. overnight. Eleven of the resulting phage plagues were picked and inoculated in 3 ml of log phase JM103 diluted 1:100 with R2-6 medium (5.0 g Tryptone, 5.0 g yeast extract, 5.0 g NaCl and 1.0 L distilled $H_2O$, pH 6.9). These cultures were incubated at 37° C. for six hr and spun down in Eppendorf tubes. The supernatant containing free phage was stored at 4° C. while mini-screen DNA was prepared from the cell pellets by the alkaline lysis method. The mini-screen DNA was analyzed by restriction digestion with the enzymes HindIII and BglII. One clone was chosen and was designated MP11:Pcs. The supernatant from this clone was used to infect JM103. A 15 ml culture of the JM103 MP11:Pcs was grown for six hr, spun down, and single stranded phage DNA was isolated from the supernatant.

The phage DNA MP11:Pcs was mutagenized with oligonucleotide LF01 (5'-GAATATATAACG-GAGCTCCCGGGATCC ACCTGTTTTACC-3')

(SEQ ID No: 9), which contains the restriction site sequences for the enzymes SstI, SmaI, and BamHI flanked by 12 bp of cellulose synthase operon promoter seguence on each side. One picomole of the single-stranded phage DNA MP11:Pcs was incubated with 10 pmoles of LF01 at 68° C. for 5 min and then allowed to anneal with the promoter sequences for 30 min at 37° C. The annealed molecules were then extended to form complete double-stranded DNAs by adding dNTPs to 0.5 mM and the Klenow fragment of DNA polymerase 1 to 0.25 units/ul. The extension proceeded at 4° C. for 30 min, and then at 37° C. for one hr; it was then heated to 68° C. for 10 min and the mixture used to transform JM103 competent cells.

Figure 9A:
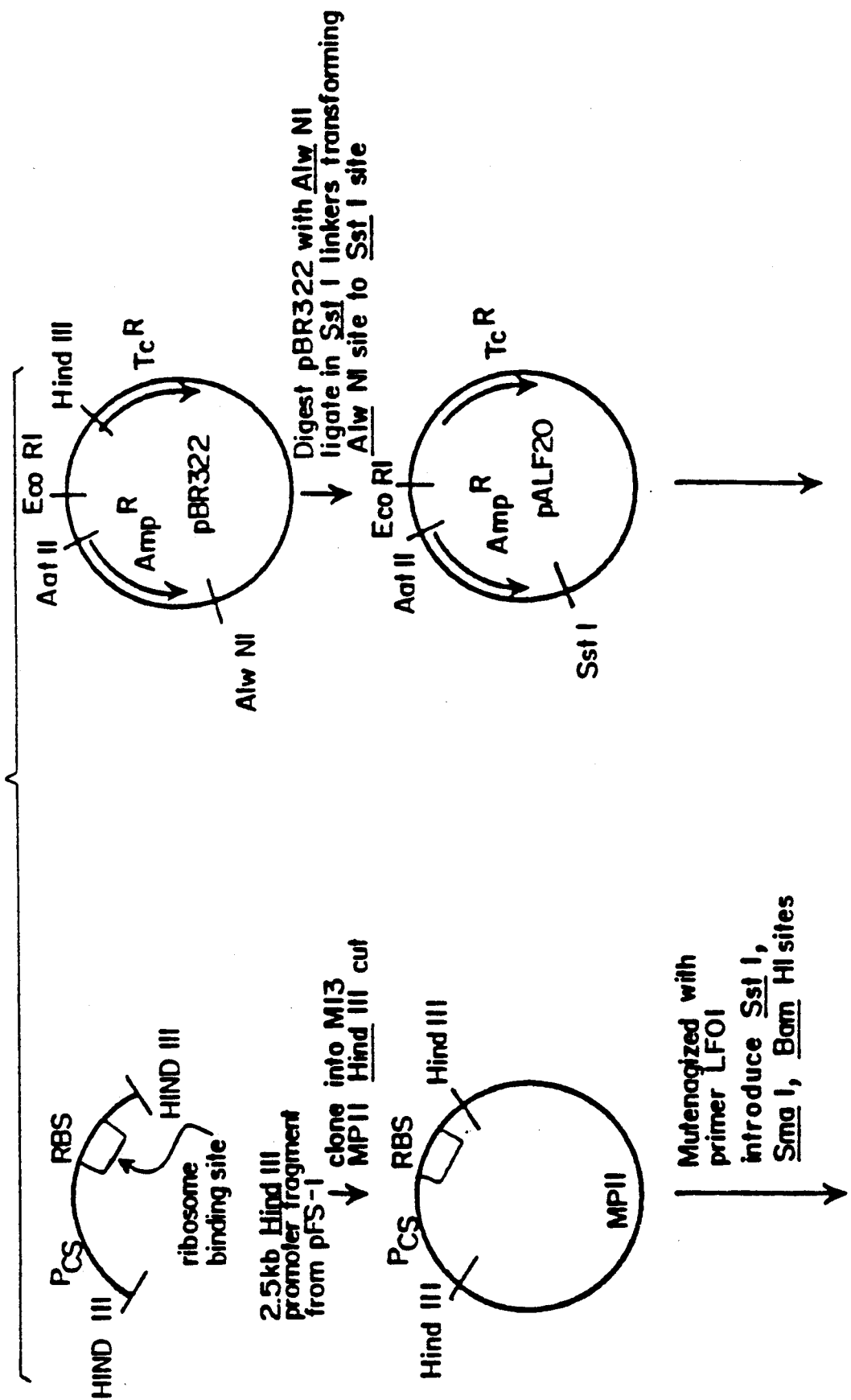
FIG. 9 is a flow chart describing the construction of expression vectors containing heterologous promoters to transcribe the genes of the cellulose synthase operon.
Figure 9B:
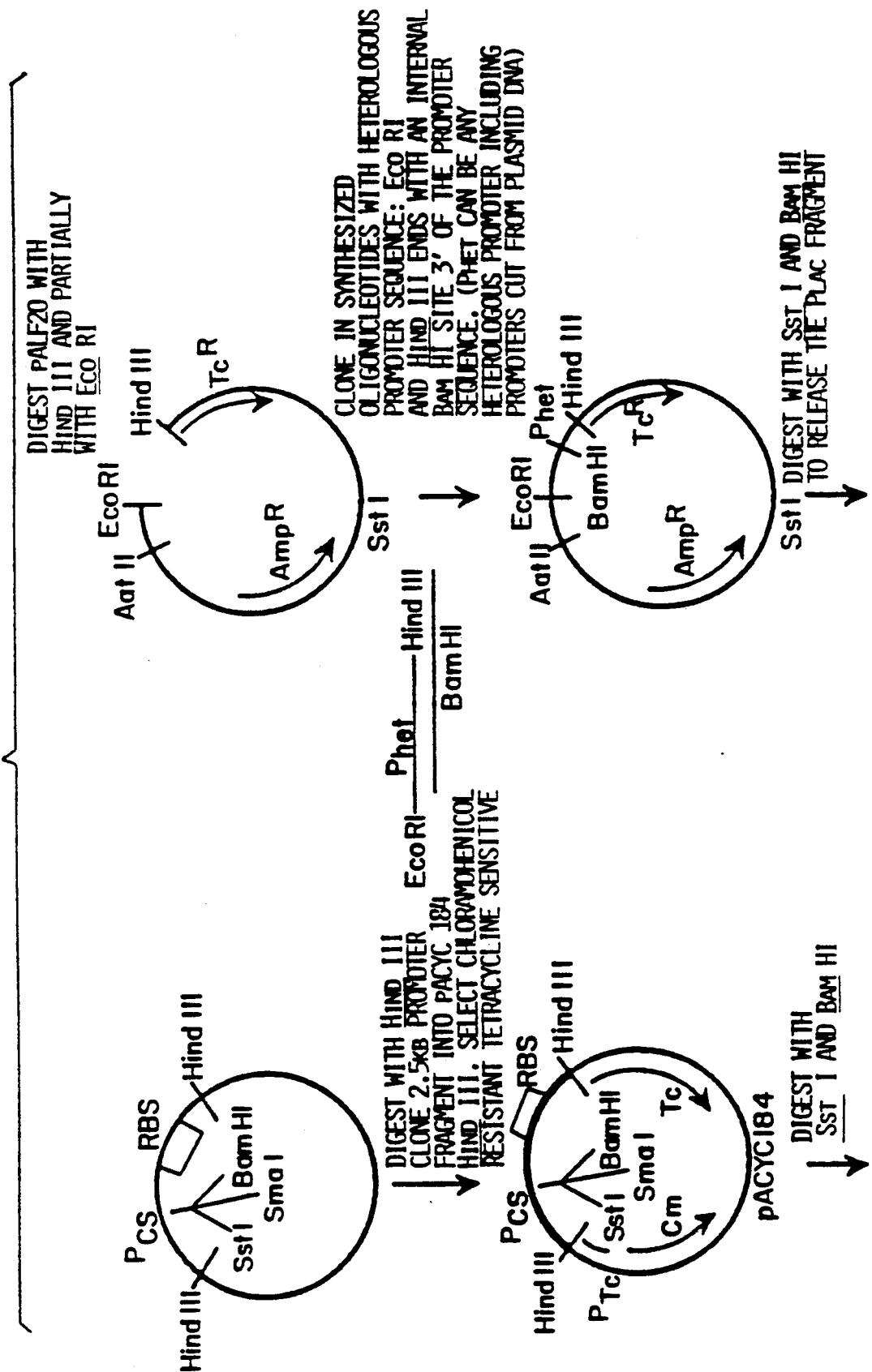
Figure 9C:
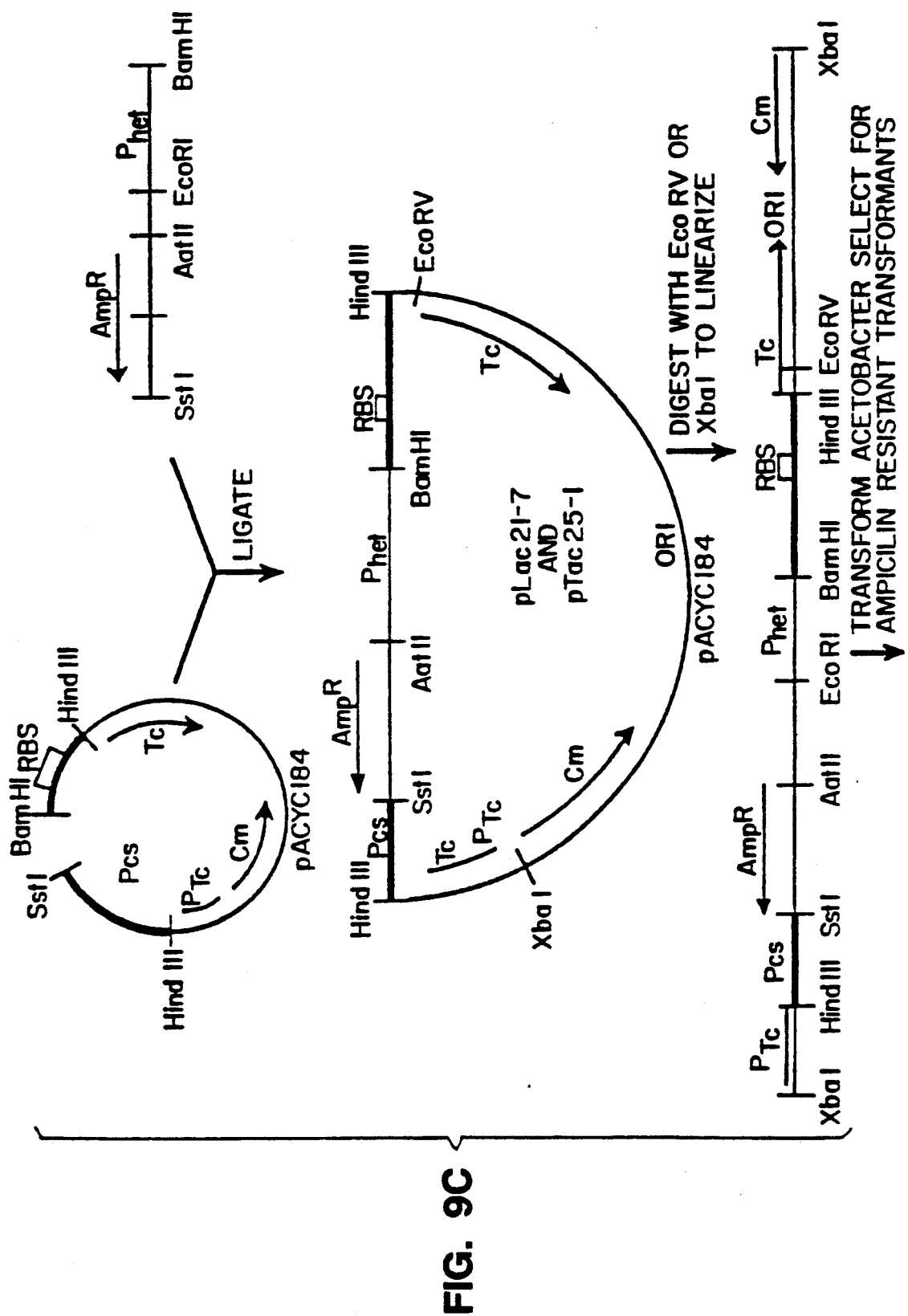

The transformation mixture was plated with JM103 lawn cells on R2-4 plates with 3 ml R-17 (10.0 g N-Z amine, type A, 5.0 g NaCl, 0.04 g X-gal in 2.0 ml DMF), 10 mM $MgCl_2$, 0.7% top agarose. Phage plaques were lifted from these plates onto nitrocellulose filters and the plates stored at 4° C. The filters were baked at 80° C. for two hr and hybridized with the 32P-labeled oligonucleotide probe LF02. LF02 contains a subset of the seguence of the oligonucleotide LF01 used for mutagenesis, the three restriction site sequences with only 2 bp of cellulose synthase promoter seguence on either side. The seguence of LF02 is 5' CGGAGCTCCCG-GGATCCAC-3' (SEQ ID No: 10). Hybridization was carried out at 58° C. The filters were washed at 58° C. with sequential 5 min washes of 5x SSC, 2x SSC, and 2x SSC containing 0.1% SDS. Kodak X-OMAT AR film was exposed to the filters for 60 hr. After 60 hr, dark spots appeared on the developed film which corresponded to the lifted plagues still present on the plates. Sixteen plagues which corresponded to dark spots on the film were isolated and the RF DNAs were analyzed by restriction digestion with the enzymes HindIII, BamHI, and SstI. MP11:Pcs:LF01 corresponded to the map provided in FIG. 9. The introduced restriction sites in MP11:Pcs:LF01 are for substitution of heterologous promoters. The flanking regions serve as the sites for homologous recombination between the plasmid and the Acetobacter chromosome in gene replacement.

The phage supernatant from culture MP11:Pcs:LF01 was plague purified, checked again for the appropriate restriction pattern, then used for infection and preparation of double stranded cesium chloride gradient purified DNA.

B. Construction of pACYC184:Pcs

Twenty micrograms of MP11:Pcs:LF01 DNA were digested with 200 units of HindIII, and the 2.5 kb fragment containing the cellulose synthase promoter region was gel purified, electroeluted into 0.1x TEA in a dialysis bag at 100 volts for 2 hr. The DNA and buffer were removed from the bag, extracted with phenol/chloroform, precipitated with sodium acetate in ethanol and resuspended in Tris-EDTA buffer. This fragment was ligated to HindIII-digested pACY184 (New England Biolabs) with an insert-to vector ratio of 10:1 at an ATP concentration of 2 mM at 16° C. overnight. The ligation mixture was transformed into MM294 competent cells and plated on R2-4 plates containing Cm at 20 ug/ml. The plates were incubated at 37° C. overnight and over 15,000 $Cm^R$ colonies appeared. To test for inactivation of the tetracycline resistance gene of pACYC184 by the insertion of the Pcs fragment, 66 of these colonies were patched onto R2-4 plates with chloramphenicol at 20 ug/ml and R2-4 plates with tetracycline at 15 ug/ml and incubated at 37° C. overnight. Six of the sixty-six $Cm^R$ colonies showed sensitivity to tetracycline on the patch test. Mini-prep DNA was isolated from these six clones, digested with HindIII, and analyzed on 0.8% agarose gel. Three of the plasmids showed one 2.5 kb HindIII insert while the other three showed two or more. The plasmid designated pACYC184:Pcs showed a single 2.5 kb HindIII insert. Cesium chloride ethidium bromide gradient purified DNA was isolated from cultures containing this plasmid.

Forty ug of pACYC184:Pcs DNA was partially digested with 4 units of BamHI and gel purified. The approximately 6.7 kb fragment, containing linearized plasmid molecules cut at one of the two BamHI sites, was isolated and then digested to completion with SstI. The fragments were gel purified and the 6.7 kb BamHI-SstI fragment, was cut from the gel, electroeluted into 0.1x TEA, extracted with phenol/chloroform, precipitated with sodium acetate in ethanol, and resuspended in Tris-EDTA buffer.

C. Introduction of a Unique SstI Site into pBR322.

Ten micrograms of pBR322 DNA was digested to completion with the restriction endonuclease AlwNI, and the ends were made blunt. SstI (SacI) linker oligonucleotides from New England Biolabs were ligated with T4 ligase to the blunt-ended pBR322 cut fragment under standard conditions. The ligation mixture was digested directly with 5 units of SstI, gel purified and then ligated to itself with T4 DNA ligase under standard conditions. This ligation mixture was used to transform MM294 competent cells with selection for ampicillin resistance. One culture, MM294 pALF20, gave DNA which was linearized with SstI and was approximately 4.4 kb in length. This plasmid was then used to accommodate the lac and tac promoters.

D. Annealing of Oligonucleotides

Oligonucleotides were synthesized to form the tac and lac UV5 promoters. Each oligonucleotide contains the seguence for one strand of the promoter, with one strand of an EcoRI half site at one end and one strand of a HindIII half site at the other. The synthesized oligonucleotides were suspended in $H_2O$ to a concentration of 100 pmoles/ul. Two hundred pmoles of each oligonucleotide were treated with 9 units of polynucleotide kinase in a 20 ul reaction containing 1 mM ATP at 37° C. for 30 min. Once kinased, the oligonucleotides were mixed together in pairs then heated for 15 min to 68° C. to unpair any secondary structure. The oligonucleotides were then allowed to anneal together by cooling to 37° C. and incubating for 30 min. After 30 min the annealed oligonucleotides were included in ligation reactions with the pALF20 EcoRI/HindIII fragment isolated as described below.

E. Preparation of Vector

Twenty ug of the plasmid pALF20 were digested with 100 units of EcoRI and 100 units of HindIII at 37° C. for 1.5 hr. The reaction was run on a 0.8% GTG agarose gel and the approximately 4.4 kb fragment, corresponding to linearized DNA, was cut from the gel. The fragment was electroeluted into 0.1x TEA buffer in a dialysis bag at 100 volts for 1.5 hr. The DNA and buffer were removed from the bag, extracted with phenol and chloroform, then precipitated with sodium acetate in ethanol. The DNA was dried in a speed vac and resuspended in H₂O.

F. Ligations

Each pair of annealed oligonucleotides was ligated to the HindIII/EcoRI digested pALF20 DNA in a reaction containing 0.1 mM ATP with an insert to vector ratio of 3:1 at 16° C. for 3.5 hr. As a control, the vector EcoRI/HindIII digested pALF20 was ligated to itself under the same conditions. An aliquot of each ligation mixture was taken before adding the ligase and after ligation for 3.5 hr. These aliguots were run on a 0.8% agarose gel and showed significant increase in molecular weight after 3.5 hr at 16° C., indicating successful ligation.

G. Transformations

Each ligation mixture was transformed into DG101 competent cells and plated on R2-4 plates containing tetracycline at 15 ug/ml. The transformation with the vector ligating on itself gave six tetracycline resistant colonies. pALF20:lacUV5 gave 30 tetracycline resistant colonies, pALF20:tac gave 99. Cesium chloride ethidium bromide gradient purified DNA was prepared from three clones from the pALF20:lacUV5 transformation, designated pLac19, pLac20, and pLac21, and the two clones from the pALF20:tac transformation, designated pTac24 and pTac25. These plasmids were sequenced to determine the presence of an annealed oligonucleotide promoter insert:

| | |
|---|---|
| pLac21: | Contained the lacUV5 sequence with no errors. |
| pTac25: | Contained the tac promoter sequence with a 1 bp mismatch from G to A at the −47 position of the promoter. |

Plasmids pTac25 and pLac21 were selected to continue construction. Ten ug of each plasmid were digested to completion with SstI and then with BamHI. The approximately 1.5 kb fragments containing the ampicillin resistance gene attached to a heterologous promoter (tac or lac) were cut out of the gels, electroeluted into 0.1x TEA, extracted with phenol/chloroform, precipitated with sodium acetate in ethanol, and resuspended in Tris-EDTA buffer.

H. Ligations

The approximately 6.7 SamHI-partial SstI pACYC184:Pcs vector fragment (isolated in Section B) was ligated to the BamHI/SstI ampicillin resistance heterologous promoter fragments from pLac21 and pTac25 in two separate ligation reactions with insert to vector ratios of 7:1 and an ATP concentration of 0.2 mM at 16° C. for 24 hr. These two ligation mixtures were used to transform DG101 competent cells. The transformations yielded 786 ampicillin resistant transformants for pACYC184:Pcs:Lac21 and 803 ampicillin resistance transformants from pACY184:Pcs:Tac25. Cultures were grown in R2 with ampicillin at 50 ug/ml from 9 colonies from each transformation. Alkaline lysis mini-prep DNA was isolated from these cultures and analyzed by restriction digestion with the enzymes BamHI, HindIII, and SstI. DNAs which corresponded to the restriction map for the plasmids designated pLac21-7 and pTac25-1 in FIG. 9 were identified. These plasmids were used to transform 1306-21 electrocompetent cell stock. The resulting strains were subjected to Southern blot analysis to verify the chromosomal configuration of these strains, and then used in fermentation experiments to measure the levels of cellulose synthase activity and cellulose production.

These two strains, along with the untransformed host strain 1306-21, were tested using standard protocols. Strains were tested in duplicates for cell growth, cellulose production and in vitro cellulose synthase activity for days 1, 2 and 5. One hundred twenty five milliliter baffled flasks were inoculated with a 2% cellulase containing seed media. Standard flask media containing R70-2 with 10 uM FeCl3, 25 mM DMG, 1% TYE and 3% glucose was used in these studies.

The cultures for the enzyme assays were harvested, the cells passed through cheese cloth, and the cells were washed using previously described protocols. The cell pellets were frozen as the samples were collected. Later the cells were sonicated and then assayed for cellulose synthase activity, production of cellulose, and cell growth. Parallel sets of flasks were used to measure in vitro cellulose synthase activity.

The results of this experiment demonstrate that one can replace the Acetobacter chromosomal promoter of the cellulose synthase operon with an E. coli promoter and still obtain in vitro cellulose synthase activity and cellulose production. The in vitro cellulose synthase specific activity of the tac-promoter construct was similar to that of the wild-type cells throughout the fermentation, both in the activity of day-old cultures, and in the decline in activity in the two and five day-old cultures, while the activity of the lac promoter construct was lower than that of the wild-type strain. Its activity also declined between the first and second days.

Cell growth and cellulose production of the tac promoter construct were experimentally identical to that of the control. The lac promoter construct was lower in cellulose production, but not in cell growth, as compared to the control. This data suggests that production of cellulose in the lac promoter strain was limited by the in vivo activity of cellulose synthase.

Thus, as demonstrated herein, promoters of varying strength may give rise to different enzyme activities and cellulose to cell ratios.

EXAMPLE XVII

Construction of Promoter Replacement Vector pTLW70.5:P$_L$DraI

The construction of promoter replacement plasmid pTLW70.5:P$_L$DraI containing the P$_L$ promoter of the E. coli phage lambda and the intermediate vector used for its construction is described as follows.

A. Preparation of P$_L$ Promoter Fragment

Twenty ug of pDG160 (a derivative of pFC54.t except that the IL-2 coding seguence was substituted with the linker HindIII, SacI, NcoI, KpmI, SmaI, BamHI (Wang, et. al., (19B5) Science, 228:149-154) DNA were digested with EcoRI releasing a 773 bp EcoRI fragment. The DNA was then digested with BamHI releasing a 383 bp P$_L$ fragment and a 390 bp fragment carrying the cry terminator. The fragments were cut with DraI which cut the 390 bp fragment into 240 bp and 141 bp fragments and the fragments were gel purified. The 383 bp fragment carrying the P$_L$ promoter was isolated.

B. Preparation of pTLW70.5 Vector Fragment

Twenty ug of the promoter replacement vector pTLW70.5 (constructed by ligating an approximately 4.3 kb filled-in HindIII fragment from pTac25-1 to an approximately 1.9 kb filled-in EcoRI-BamHI fragment from pACYC184) was linearized by digestion with EcoRI. The DNA was digested with BamHI, gel purified and the 6.2 kb fragment was recovered.

C. Ligation and Transformation

The 383 bp fragment containing the lambda $P_L$ promoter from pDG160 was ligated to the pTLW70.5 EcoRI/BamHI cut vector in a reaction containing 0.1 mM ATP with an insert-to vector ratio of approximately 40 to 1. As a control, the pTLW70.5 EcoRI/BamHI cut DNA was ligated to itself under the same conditions with no insert DNA present. E. coli DG116 is an E. coli K12 strain with c1857 lambda repressor (Wittman and Wong, J. Bacteriol 170:3206–3612). Competent cells were transformed with each ligation mixture and then incubated on R2-4 plates with 50 ug/ml Amp. $Amp^R$ transformants were obtained and one of the clones was designated pTLW70.5:$P_L$DraI.

D. Colony Lifts to Screen For $P_L$ Insert

The transformation mixture for pTLW70.5:$P_L$DraI was plated on a nitrocellulose filter then laid over R2-4 media containing 50 ug/ml Amp. After overnight incubation, 39 colonies grew on the filter. The colonies were replica plated onto a second filter. The second filter was incubated at 30° C. overnight. The original filter was incubated at 30° C. for 3 hr.

GE349 is an 18-mer oligonucleotide [CAATGTG-CCAATCGCGGG —SEQ ID No: 15) comprising the PL promoter seguence. GE349 was labeled with $^{32}P$ gamma ATP in a reaction with polynucleotide kinase, then allowed to hybridize to the original filter at 50° C. for approximately 20 hr under standard hybridization conditions. The filters were washed successively for 10 min in 5X, 2X, 1X, and 0.5X SSC, 0.1% SDS at 50° C. The filter was exposed to Kodak XOMAT AR film at −70° C. overnight, and then developed. Eight colonies on the duplicate filter which corresponded to the darkest exposure spots on the film were picked individually into 350 mls of R2 with 50 ug/ml Amp and cultured with shaking at 30° C. for approximately 20 hr. Plasmid DNAs were isolated using CsCl gradients. DNA sequencing and restriction enzyme analysis indicated that all eight clones were carrying the $P_L$ insert. One plasmid was designated pTLW70.5:$P_L$DraI9.

E. Transformation of Acetobacter strains 1306-21 pTLW70.5:$P_L$DraI-19 DNA was linearized with XbaI and then about 5 ug of this linearized DNA was used to transform strain 1306-21 via electroporation under standard conditions. The electroporation mixture of strain 1306-21 pTLW70.5:$P_L$DraI-19 was resuspended in R20-2 with 0.2% cellulase and plated on R20-2 plates with 20 ug/ml Cm and 100 ug/ml Amp. Colonies arising on these plates appear to make cellulose. One of the colonies was picked and was designated as 1306-21 $P_L$.

F. Evaluation of Recombinant Strains

The cellulose production of recombinant strain 1306-21 $P_L$ was measured in flasks at low agitation in the presence of Floxan EA-1340. All seed cultures were grown in R70-3 plus 0.5% (w/v) TYE Ambrex 1003, 25 mM DMG, 0.1% (v/v) cellulase and 3% (w/v) glucose. The seed flasks were incubated at 30° C., 125 rpm overnight, and then the cell mass in each flask was determined by $OD_{680}$ measurements.

The test medium for the flask experiment was R70-3 plus 1 g/L Floxan EA-1340, 2% (v/v) CSL, 25 mM DMG and 10 g/L glucose. The growth of the control strain 1306-21 was under the same conditions for seed and test stages but without Amp.

The experiment was done in 125 ml baffled flasks (25 ml medium/flask). The test flasks were incubated at 30° C., 125 rpm for three days, and then the cellulose and cell mass were determined.

Cell growth and cellulose production of the 1306-21 $P_L$ and 1306-21 $P_L$ control cultures are given in the following table. All of the cultures had a final pH of 5.6–5.9.

| Cell Growth and Cellulose Production | | | | |
|---|---|---|---|---|
| | Average Cellulose (g/L) | Cellulose (g/L) | Cells (g/L) | Cellulose/Cells |
| 1306-21 Control | 5.39<br>5.38 | 5.39 | 1.58 | 3.41 |
| 1306-21 $P_L$ | 6.26<br>6.27 | 6.27 | 1.52 | 4.13 |

The data show that 1306-21 $P_L$ produced more cellulose than the 1306-21 control. For the cellulose synthase in vitro activity, the 1306-21 $P_L$ strains were grown as described in Example II with 50 ug/ml Amp added. Cellulose synthase activity was measured as described in Example VIII. Cellulose synthase in vitro activity in 1306-21 $P_L$ was 0.95 umole/mg cell hr (186%) while that for 1306-21 was 0.51 umole/mg cell-hr (100%). These results are compatible with the increase in cellulose production and cellulose to cell ratio in 1306-21 $P_L$.

G. Fermentation of 1306-21 $P_L$

The fermentation of 1306-21 $P_L$ was compared to 1306-21 in a SG14 Chemap fermentor. The medium used was R70-3 supplemented with 4% CSL and 30 g/L glucose, with additional glucose being fed to the culture during the fermentation to maintain an adequate supply. The medium also contained 1 g/L Floxan EA1340, an anionic polyacrylamide. The fermentor cultures were controlled at 32° C., at pH 5.0 with $H_2SO_4$ and $NH_4OH$, and at a dissolved oxygen concentration of 60% of air saturation. They were inoculated 5% v/v from flask cultures grown to approximately 1 OD (680 nm), in medium containing cellulase to suppress cellulose accumulation. Seed preparation is described in Example XV. The initial cell density was 16 mg dry weight per liter for 1306-21 ($P_L$), and 18 mg dry weight per liter for 1306-21. The fermentor agitation rate was increased manually from an initial set point of 400 rpm in order to maintain bulk mixing in the increasingly viscous broth.

Figure 12:
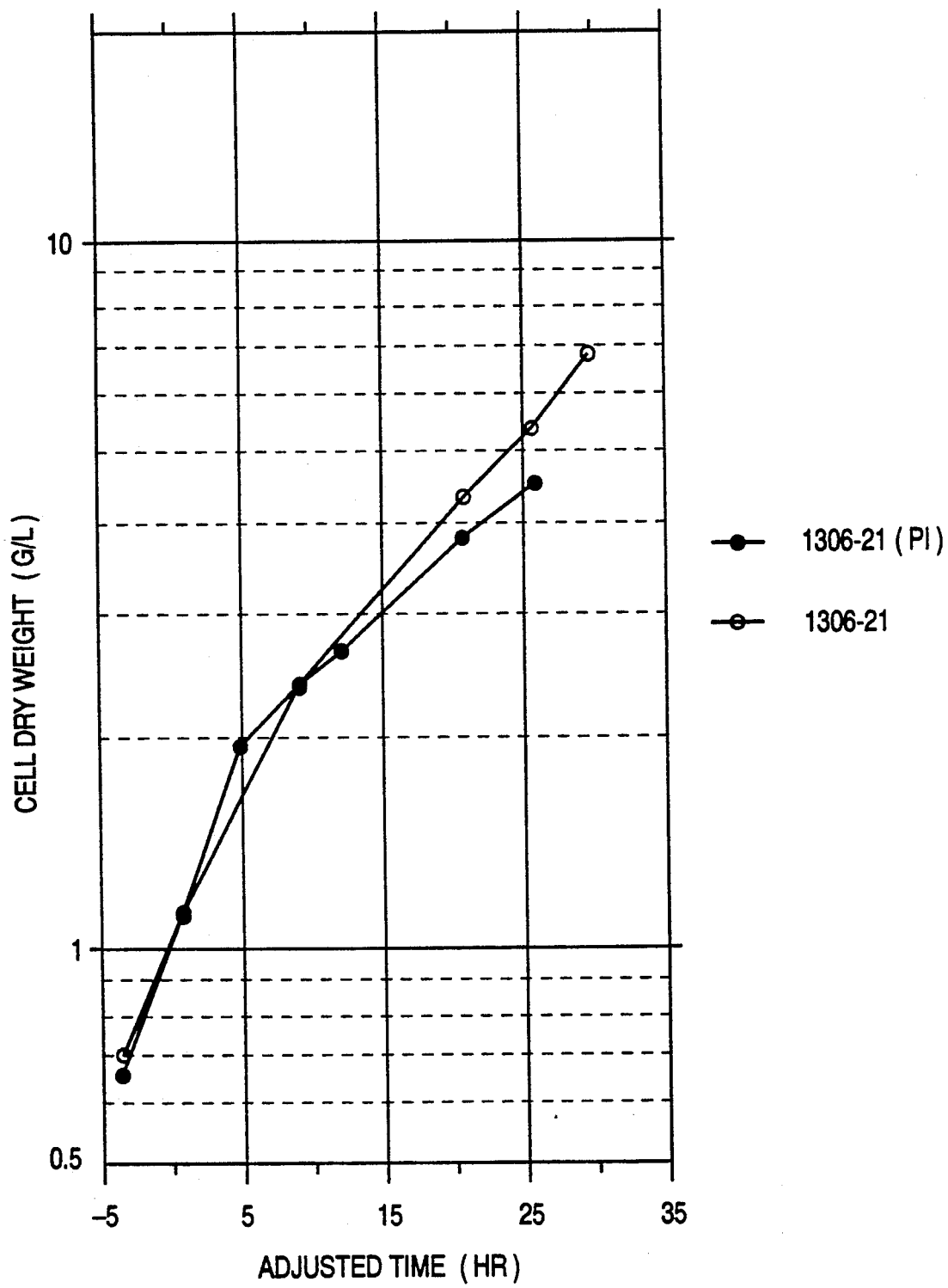
FIG. 12 illustrates the rate of cell growth of recombinant strain 1306-21 $P_L$ and control in the presence of an anionic polyacrylamide, Floxan EA1340.
Figure 13:
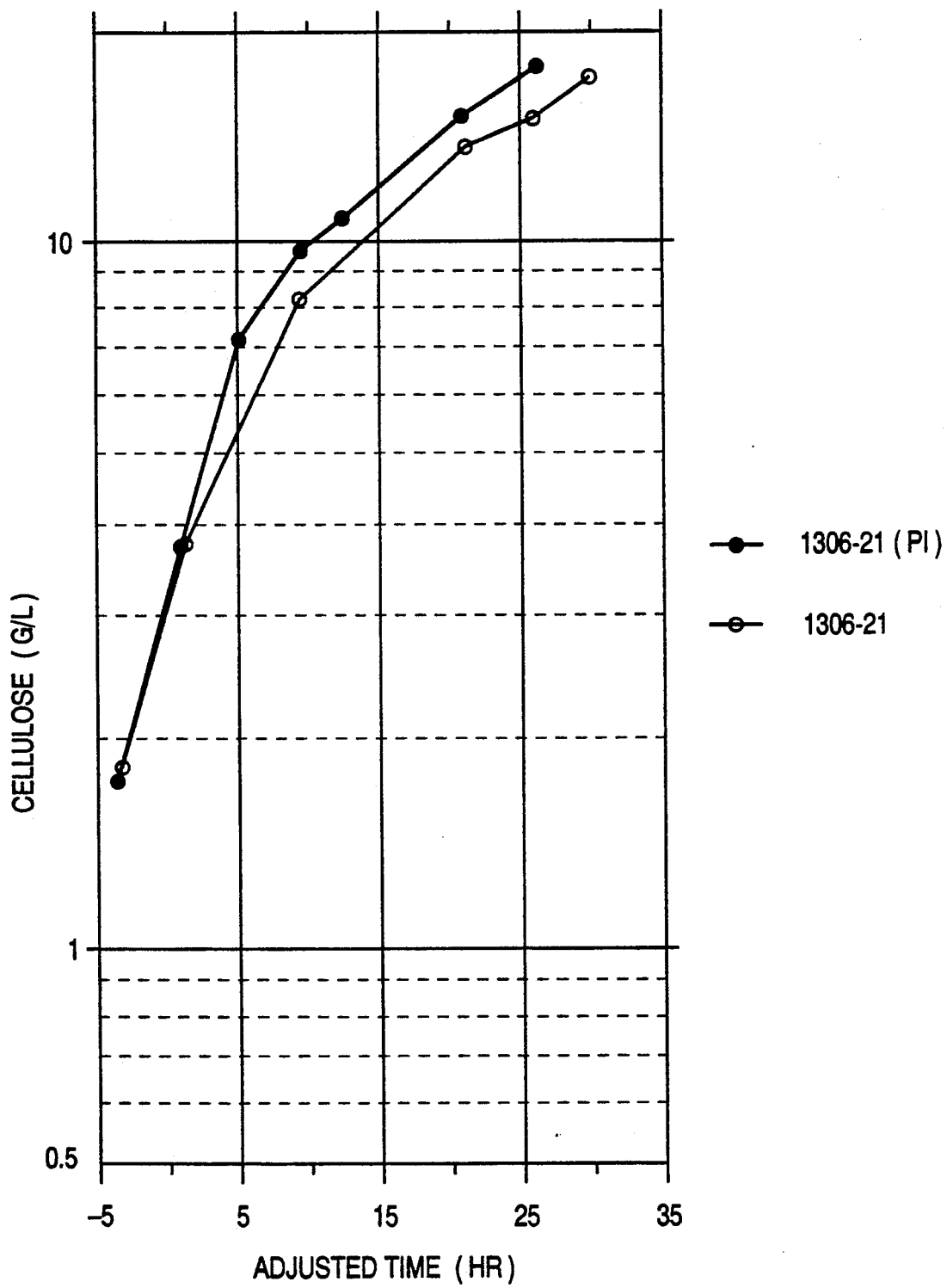
FIG. 13 illustrate the rate of cellulose produced from recombinant strain 1306-21 $P_L$ and control in the presense of the anionic polyacrylamide Floxan EA1340.
Figure 14:
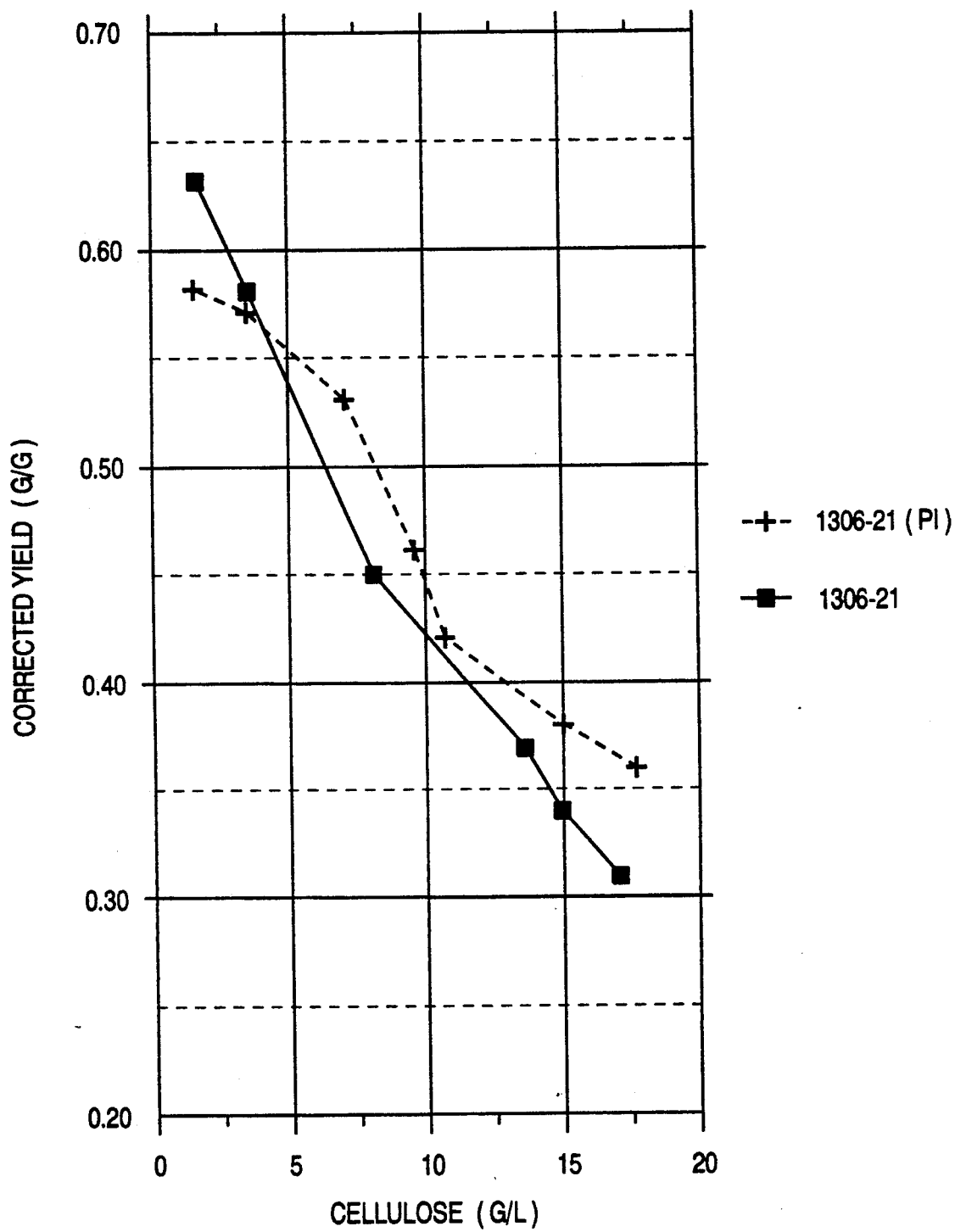
FIG. 14 shows the yield of cellulose on glucose averaged over two runs from recombinant strain 1306-21 $P_L$ and control.

The results are shown in FIGS. 12, 13, and 14 (the time scales have been adjusted such that at time zero the cell density was 1 g/L, to facilitate comparison). It can be seen that, although the recombinant strain grew slightly more slowly above 2 g/L (FIG. 12), its cellulose accumulation rate was slightly higher (FIG. 13). As a result, the peak volumetric productivity for the recombinant strain was 0.38 g/L-hr, versus 0.35 g/L-hr for the parent strain. These values do not take the difference in inoculum density into account, and therefore underestimate the true magnitude of the difference in volumetric productivity between the strains.

FIG. 14 shows the yield of cellulose on glucose for the two runs, corrected for the effects of sampling and of volume changes. It can be seen that the yield with the recombinant strain averages about 12% higher than the parental strain above 8 g/L. Thus the data indicates that the recombinant strain makes cellulose faster and more efficiently than the parental strain under these conditions.

EXAMPLE XVIII

Construction of Strains 1306-21R3 Carrying Regulatory Elements of the E. coli lac Operon An Acetobacter strain whose cellulose production can be switched off and on by simple manipulations of the growth media would facilitate the development of a two-stage fermentation process The first stage would involve Cel⁻ growth to high density without the physical limitations imposed by the presence of cellulose. In the second stage, cellulose production would be switched on in a high density culture, resulting in a high volumetric productivity at the end of a batch run.

The construction of a new strain to carry both the cellulose synthase operon under control of the E. coli tac promoter and the E. coli lacI gene on a plasmid derived from pKT230cos5 are described below.

A. Construction of tac Promoter Strains 1306-21 TaC+op-19 and 1306-21 Tac+op-22

1. Digestion of pTACNE01.3

The plasmid pTACNEO 1.3 (ATCC 37688) carries the full tac promoter seguence including the 27 bp operator region. Ten ug of pTACNEO plasmid DNA was completely digested with BamHI and used as the template DNA for the following PCR amplification.

2. PCR Amplification of the tac Promoter Region

The tac promoter region was amplified from the linearized pTACNEO plasmid in a PCR reaction with the primers LF07 (SEQ ID No: 11) and LF08 (SEQ ID No: 12). The sequences of these primers are:

```
LF07:  5'-GTTCAAGAATTCCCCGGGACAACGGTTCTGGCAAATATTC-3'
LF08:  5'-GTACCGGATCCTGTGTGAAATTGTTATCCGC-3'
```

The expected PCR product should carry the tac promoter seguence from −70 to +28 with the addition of an EcoRI and SmaI site at the −70 end from the primer LF07 and a BamHI site at the +28 end from the primer LF08.

This product was amplified in four separate PCR reactions each containing 100 ng of linearized pTACNEO DNA, 37.5 pmoles LF07, 37.5 pmoles LF08, 150 uM dNTPs, 10 units of Tag polymerease, and 1X Perkin Elmer-Cetus Reaction Buffer.

The amplification was carried out in a Perkin Elmer Cetus DNA Thermocycler for 10 cycles with a denaturation temperature of 94° C. for 1 min, an annealing temperature of 35° C. for one min, an extension temperature of 35° C. for 1 min, then 30 cycles with an annealing temperature of 60° C. for 1 min, and an extension temperature of 60° C. for 3 min.

One-tenth volume of each of the four PCR reactions (10 ul out of 100 ul) was run on a 12% acrylamide gel. For each reaction a major band was visible at approximately 116 bp.

Three of the four reactions were pooled, phenol and chloroform extracted, ethanol precipitated, resuspended in EcoRI buffer and completely digested first with EcoRI, then with BamHI and subsequently isolated.

3. Ligation, Transformation and Analysis

One-fourth of the digested PCR product was ligated to 1-2 ug of the EcoRI-BamHI-digested vector pTLW70.5 (prepared as described in Example XVII B). As a control, the same amount of vector DNA was ligated to itself with no insert present under the same conditions.

Each ligation mixture was used to transform E. coli DG101 competent cells. Alkaline lysis miniprep DNA was isolated from 18 Amp resistant transformants; six showed insertion of a 116 bp fragment with the correct seguence of the tac promoter with its lac operator seguence. Two of these six plasmids, pTLW70.5 Tac+op-19 and -22 were linearized with XbaI and used to transform 1306-21. Ampicillin resistant transformants were selected and purified.

B. Construction of Plasmid Carrying the E. coli Lactose Operon Repressor Gene lacIq

1. Digestion of pMC9

The plasmid pMC9 (Calos et al. Proc Natl Acad Sci U.S.A. 80:3015-3019) carries the E. coli lacIq gene complete with its promoter and entire coding seguence. Ten ug of pMC9 was digested with BamHI to prepare template DNA for the following PCR amplification.

2. PCR Amplification of the lacIq gene

The lacIq gene was amplified from the linearized pMC9 plasmid in a PCR reaction with the primers LF09 (SEQ ID No: 13) and LF010 (SEQ ID No: 14). The sequences of these primers are:

```
LF09:  5'-GTTCAAGAATTCCCCGGGGACACCATCGAATGGTGC-3'
LF10:  5'-GTACCGGATCCGCCGGAAGCATAAAGTGTAAAG-3'
```

The expected PCR product should carry the entire lacIq seguence from −40 of the lacIq promoter (complete with the I mutation in the promoter) to 69 bp 3' of the translation termination codon for lacIq (−16 in the lac promoter region), with the addition of an EcoRI and SmaI site at the lacIq promoter end from the primer LF09 and a BamHI site at the translation termination end from the primer LF10.

The promoter seguence was amplified in a similar manner as described above except that in the lacIq PCR reaction the annealing and extension temperatures were both 45° C. and the melting temperature was 94° C. for the first ten cycles. For each reaction a major band was visible at approximately 1.2 kb.

3. Preparation and Transformation

A 10.8 kb SmaI-BamHI fragment from pKT230cos5 was ligated to the recovered LF09:LF10 PCR product 1.2 kb SmaI-BamHI fragment at an ATP concentration of 1 mM, with 400 units of T4 DNA ligase, at 16° C. overnight. The ligation mixture was used to transform DG101 competent cells to obtain Str resistant colonies. Pooled plasmid DNAs isolated from 166 of these resistant colonies were designated pKT230cos5:lacI.

Calcium chloride competent cells were made from the strain CGSC 808 (also designated Monod strain 3.300) carrying the lac22 mutation (*E. coli* Genetic Stock Center). The strain was checked for the lacI$^-$ phenotype by plating on R17-3 plates. The strain turned the X-gal in the plates blue in the absence of an inducer.

Figure 15:
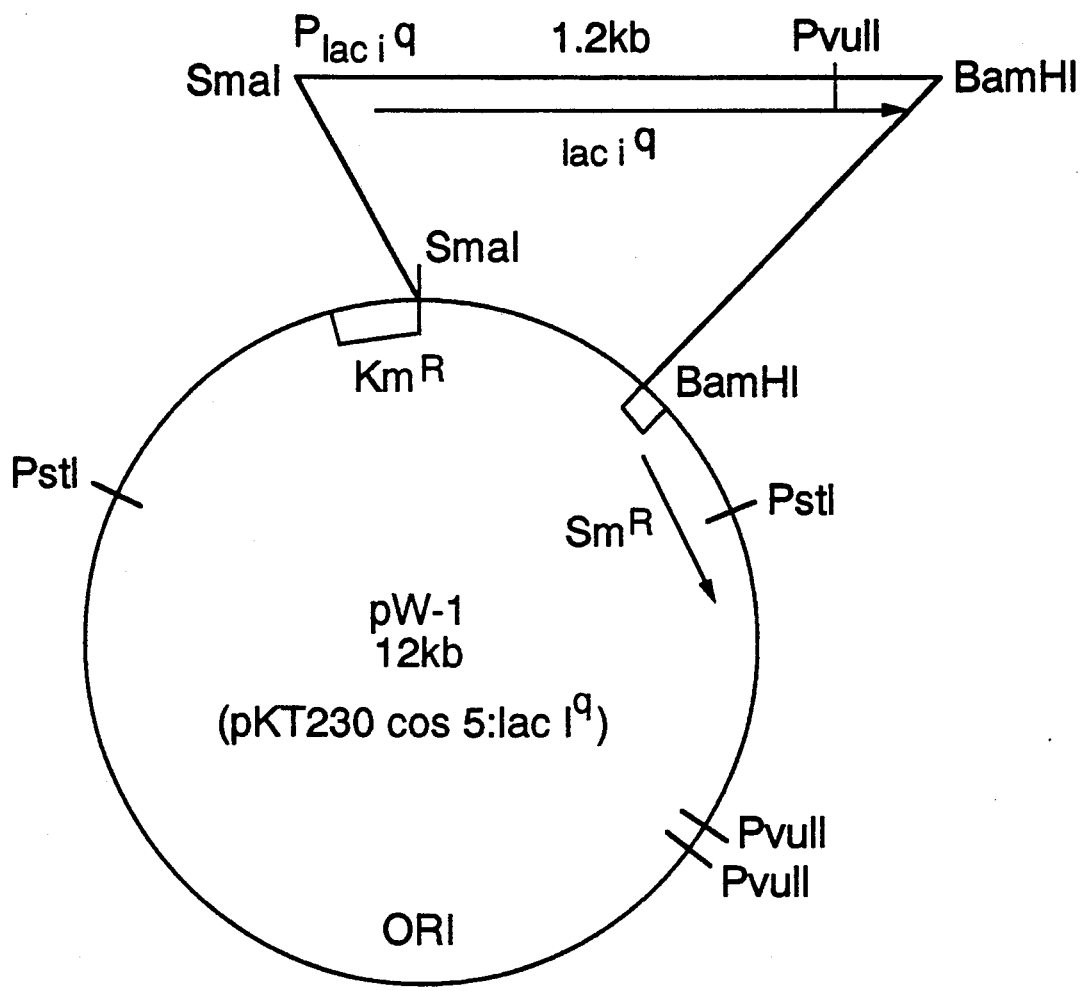
FIG. 15 is a restriction and functional map of plasmid pW1.

The CGSC-808 competent cells were transformed with 1 ug of the pKT230cos5:lacI pool DNA. Transformed cells were plated on R17-3 plates with Str at 100 ug/ml. Approximately 2,500 isolated Str resistant colonies arose on the plates. Nine of these colonies showed the white phenotype, while the remaining colonies showed the blue phenotype of the parent. Eight of the nine whites were isolated by streaking on fresh R17-3 plates with Str at 100 ug/ml. One single colony was picked from each streak and cultured in 350 ml of R2 with Str 50 ug/ml at 37° C. with shaking overnight. Frozen aliquots were stored of all eight cultures and cesium chloride ethidium bromide purified DNA isolated from each. These DNAs were designated pW1-8. All eight plasmids showed the restriction pattern for the plasmid shown in FIG. 15.

C. Transformation of 1306-21 Tac+op-19 and 1306-21 Tac+op-22 with Plasmid pW1

1. Electroporation

Two 5 ug aliquots of pW1 DNA were each dialyzed twice against 2 ml of H$_2$O in a Centricon 30. The washed DNA was dried in a speed vac and resuspended in 4 ul of H$_2$O. 40 ul of freshly thawed 1306-21 Tac+op-19 electrocompetent cells were added to 5 ug of DNA, and 40 ul of 1306-21 Tac+op-22 electrocompetent cells were added to the second 5 ug of DNA. Each of the DNA cell mixtures were electroporated under standard conditions, each resuspended in 1 ml R20-2 0.2% cellulase, each plated on R20-2 plates with Cm 20 ug/ml, plus Str 40 ug/ml and Amp 100 ug/ml and incubated at 30° C.

2. Colony Phenotypes

For strain 1306-21 Tac+op-19 transformed with pW1 at day 4 only two Amp$^R$Str$^R$ colonies were visible, both appeared to make very little or no cellulose. At day 6 these two colonies were larger but similar in Cel phenotype. Three additional colonies also appeared on the plates at day 6 but were too small to clearly distinguish their phenotype.

At day 6 the two Cel$^-$ colonies were streaked on R20-2 plates with Cm at 20 ug/ml, Str at 40 ug/ml, and Amp at 100 ug/ml. The two strains were designated 1306-21R1 and 1306-21R2.

For strain 1306 21 Tac+Op-22 transformed with pW1 at day 4 only one Amp$^R$Str$^R$ colony was visible and appeared to larger but similar in phenotype. Twenty-nine additional colonies also appeared on the plates but were too small to clearly distinguish their phenotype.

At day 6 the Cel$^-$ colony was streaked on R20-2 plates with Cm at 20 ug/ml, Str at 40 ug/ml, and Amp at 100 ug/ml. This strain was designated 1306-21R3.

D. Induction of the Cellulose Synthase Operon Regulated Strain 1306-21R3 with IPTG Strain 1306-21R3 was tested to see if it produced cellulose under normal growth conditions and if it could be induced to produce cellulose with lactose or IPTG (isopropyl-thio-$\beta$-D-galactoside) in the growth medium.

Single colonies from the streak of 1306-21R3 on R20-2 plates supplemented with Cm at 20 ug/ml, Str at 40 ug/ml and Amp at 100 ug/ml were streaked on media described in the above electroporation example with each of the following additions:

a) No addition
b) 2% lactose
c) 2mM IPTG
d) 5mM IPTG
e) 10mM IPTG

Plates were incubated for 5 days at 30° C. and examined for phenotype.

For 1306-21R3 one colony was picked from a streak on the R20-2 plates and inoculated into 1 ml R70-2 medium with 25 mM DMG, 0.5% TYE, 2% glucose, Amp at 50 ug/ml, Str at 40 ug/ml, and 0.2% cellulase and incubated at 30° C. with shaking. After 24 hr the culture was transferred to 10 ml of fresh media in 125 ml baffled flask and incubation continued for 48 hr. At 48 hr, the culture was dense but not saturated. The culture was used as seed for induction tests with lactose and IPTG and for the preparation of a frozen stock at 15% glycerol.

One ml of growing but not saturated culture for strains 306-21R1 and R3 were subcultured into 10 ml R70-2 25 mM DMG, 0.5% TYE, 2% glucose, Amp at 50 ug/ml, Str at 40 ug/ml with each of the above described additions.

Cultures were incubated in 125 ml snap cap baffled flasks at 30° C. and run at 175 rpm. Cultures were checked at day 3 for production of cellulose.

The results of growth with and without inducers on plates and in liquid media are summarized below.

|  | Plates | Liquid Media | |
|---|---|---|---|
|  | Cel phenotype | Descriptions of Cultures | Cellulose Production |
| No additives | 1306-21R3 | — | Little or No Visible Celluose | — |
| 2% Lactose | 1306-21R3 | — | Little or No Visible Cellulose | — |
| 2 mM IPTG | 1306-21R3 | + | Cellulose Pellets |  |
| 5 mM IPTG | 1306-21R3 | + | Cellulose Pellets |  |
| 10 mM IPTG | 1306-21R3 | + | Cellulose Pellets |  |

The uninduced strain 1306-21R3 appear to make little or no cellulose under the standard growth conditions tested. It appears that cellulose production is inhibited by the lac operon regulatory elements present in these strains. When grown in the presence of the inducer IPTG, however, these strains make cellulose. IPTG appears to be sufficient to inactivate the lac repressor in these strains when present in the growth medium at concentrations as low as 2 mM. Lactose was not sufficient to induce the strains to produce cellulose when present in the growth media at a 2% concentration.

E. Quantitation Evaluation of 1306-21R3 in Flasks

The experiment was done in R70-3 media plus 1% (v/v) E801A CSL, 10 g/l glucose, 25 mM DMG and 1 g/l Floxan EA-1340. The seeds were grown in R70-3 plus 0.5% (w/v) TYE, 30 g/l glucose, 25 mM DMG and 0.1% cellulase. The 1306-21R3 seed and test flasks also had 50 ug/ml Amp and 40 ug/ml Str. The seeds and the test flasks were incubated at 30° C., 125 rpm (1" throw).

As shown in the following table, strain 1306 21R3 with 2 mM IPTG had similar cell growth and cellulose production as compared to the 1306 21 control as measured at Day 3. Without IPTG cellulose production is low and cell growth is enhanced.

|  | Cellulose (g/L) | Average Cellulose | Cell Mass (g/L) | Cellulose/Cell Ratio |
|---|---|---|---|---|
| 1306-21 O IPTG | 6.06 6.04 | 6.05 | 1.12 | 5.40 |
| 1306-21R3 O IPTG | 1.44 1.50 | 1.47 | 2.32 | 0.63 |
| 1306-21R3 2 mM IPTG | 5.96 6.05 | 6.01 | 1.14 | 5.27 |

EXAMPLE XIX

Experiments With Cellulose Synthase D Gene

The purpose of this experiment was to construct a 1306-21 derivative strain for exploration of the function of the cellulose synthase operon D gene (SEQ ID No: 6). The strain constructed herein can produce a polypeptide from gene D, which lacks 16.5% of the C-terminus of the wild type protein. A second construction wherein the complete gene D is removed was also constructed. These strains were tested for their phenotype with respect to cellulose production.

A. Cloning of a 3.7 kb Fragment Containing Gene C and D Sequences into pACYC184

Twenty ug of pACYC184 DNA were digested with 200 units of EcoRV and 200 units of BamHI in a total volume of 300 ul at 37° C. for 2 hr. The DNA was treated with 14 units of calf intestinal alkaline phosphatase at 37° for 30 min, then run on a 1% GTG agarose gel. The approximately 4 kb EcoRV/BamHI fragment was cut from the gel, electroeluted into a small volume of 0.1X TEA at 100 volts for 1 hr, phenol and chloroform extracted, precipitated with sodium acetate in ethanol and resuspended in 10 ul Tris-EDTA buffer.

Fifty ug of pBR322:5.5 T19G9 DNA were digested to completion with SmaI, checked for complete linearization, and then digested with BamHI. (The 5.5 kb BamHI fragment from TRT11-4 (Example XIV.C) was cloned into the BamHI site of pBR322 to construct pBR322:5.5 T19G9.) The digested DNA was run on a 1% GTG agarose gel, the approximately 3.7 kb fragment (FIG. 1 nucleotides 6341-10164), containing the 3' portion of gene C (SEQ ID No: 5) and the complete gene D (SEQ ID No: 6), was cut from the gel and electroeluted into a small volume of 0.1X TEA at 100 volts for 1 hr. The DNA was then phenol/chloroform extracted, precipitated with sodium acetate in ethanol, and resuspended in 10 ul Tris EDTA.

Approximately 2 ug equivalents of the pACYC184 BamHI/EcoRV fragment were ligated to approximately 25 ug equivalents of the 3.7 kb BamHI/SmaI fragment, at an insert-to-vector ratio of approximately 3:1 with two units of T4 DNA ligase in a 20 ul volume at 16° C. for 3.5 hr at an ATP concentration of 100 uM. The ATP concentration was then increased to 1 mM and the ligation mixture incubated overnight at 16° C.

This ligation mixture was used to transform MM294 competent cells under standard conditions. The transformed cells were selected on R2-4 plates containing 20 ug/ml Cm and incubated at 37° C. overnight. $Cm^R$ transformants were obtained and clones were picked for preparation of alkaline lysis mini screen DNA. Clone pACYC184:3.7 carries a 3.7 kb SmaI-BamHI insert containing the 3' end of gene C and all of gene D, including the stem and loop terminator structure at the end of the operon. Cesium chloride ethidium bromide gradient purified DNA was isolated for pACYC184:3.7.

B. Interruption of Gene D Sequence

Twenty ug of pACYC184:3.7 DNA were digested to completion with EcoRV extracted with phenol/chloroform, precipitated and then resuspended in 20 ul of Tris-EDTA.

Five ug of pBR322 DNA was digested to completion with EcoRI and AlwNI. The DNA was precipitated and the sticky ends filled-in with Klenow in the presence of all four dNTPs.

The filled-in DNA was run on a 1% GTG agarose gel, the 1.5 kb $Amp^R$ fragment cut from the gel, electroeluted into 0.1X TEA, phenol/chloroform extracted, precipitated and resuspended in 5 ul Tris-EDTA buffer.

The 5 ug equivalents of pBR322 $Amp^R$ fragment DNA were ligated to 1 ug equivalent of the pACYC184:3.7 EcoRV-digested DNA at an insert to vector ratio of approximately 9:1 under standard ligation conditions. The ligation mixture was used to transform MM294 competent cells under standard conditions. The transformation was plated on R2-4 Amp 50 plates and incubated at 37° overnight. $Amp^R$ colonies were obtained and cultured. Cells were harvested from each culture and alkaline lysis mini-prep DNA was isolated from the cultures. One of the DNAs, designated pDI-2, was chosen for transformation of 1306-21. pDI2 contained the Amp resistant fragment from pBR322 inserted in the EcoRV site of pACYC184:3.7, interrupting gene D. Cesium chloride ethidium bromide gradient pDI-2 DNA was prepared. 10 ug of this DNA were digested to completion with XbaI. The digest was washed with 2 ml $H_2O$ by spinning at 5,000 rpm in a Centricon 30 (Amicon). The DNA was then dried in a speed vac and resuspended in 4 ul $H_2O$. Forty ul of electrocompetent 1306-21 cells were added to the digested DNA and the cells electroporated under standard conditions. One ml of R20-2 was added to the electroporated cells and the mixture plated immediately on R20-2 Amp 100 Cm 20 plates.

After four days incubation at 30° C., approximately 100,000 $Amp^R$ colonies appeared on the plates. These transformants appeared as weak cellulose producers. Similar results were obtained for the transformants wherein the entire cellulose synthase D gene was deleted. These findings suggest that the cellulose synthase D gene does play a role in cellulose synthesis.

EXAMPLE XX

Purification of Cellulose Synthase

Strain 1306-27 was grown on a 400 ml 4% fructose, 1% yeast extract, 0.5% Bactopeptone, 0.3% $NaH_2PO_4$ medium, at pH 5.0 in 1000 ml baffled flasks, for 24 hr. Growth media was removed from the cells by washing twice with buffer (50 mM $K_2HPO_4$, pH 6.0). About 14 g of dry cells were prepared.

Cell Membranes

Cells (25 mg cells/mL) were ruptured in a French press in the presence of polyethyleneglycol (PEG) and TME buffer, 20% PEG (w/v). The broken cells were centrifuged (12,000×g, for 10 min) and the pellet was resuspended in TME buffer to the same volume. This suspension was homogenized (Potter Elevehjem homogenizer) and the suspension was centrifuged (12,000×g, for 10 min). The resulting pellet contained the cellulose synthase activity. This sample (P-PEG) was resuspended in TME buffer to a concentration corresponding to 50 mg cell weight per ml and was frozen in liquid nitrogen and stored at −80° C.

Trypsin Treatment

P-PEG was centrifuged (12,000×g, 10 min) and the pellet was suspended in 0.1M Tris, pH 8.3, 20% sucrose to 10 mg cells dry weight/ml. A 1% volume of 8 mg/ml trypsin (Sigma) was added and the preparation incubated with gentle shaking for 1 hr at 4° C. A 1% volume of 2 mg/ml trypsin inhibitor was added and the preparation was incubated for 15 min on ice. After centrifugation (100,000×g, for 30 min) the pellet (TT-P-PEG) was stored frozen at −80° C.

Solubilization

A 10% solution of digitonin (Serva, Westbury, N.Y.) in TME buffer was prepared by heating for 5-10 min in a boiling bath and the preparation was then cooled to 4° C. The TT-P-PEG pellet was suspended to 1/10 the original volume in TME buffer containing 2% digitonin. The suspension was sonified at 4° C. for 2 min using a MSE Model 140 sonifier. Sonification was carried out on 30 ml portions in 30 sec shaken and mixed gently for 90 min and then centrifuged at 200,000×g for 60 min. The supernatant contained approximately 50% of original cellulose synthase activity When frozen and stored as above, activity was retained for several months.

Enzyme Concentration

The solubilized enzyme was concentrated 5-7 fold using Amicon cones (Filter 100K) to an activity of 10-16 enzyme units/ml (unit=1 nanomole/min). The concentrated enzyme was kept overnight at 4° C. or frozen as above.

Enzyme-product Entrapment

To the bottom of each of six 40 ml centrifuge tubes for the Contron TST 28 (swinging bucket) rotor, were added 26 ml of the glycerol-containing cushion (TME buffer (pH 8.5) containing 12-13% glycerol, 1 mM UDPG and 15 umole c-di-GMP) and 10 ml reaction mixture (50 ml solubilized enzyme, 6.25 mmole Tris-HC buffer, pH 9.6, 340 umole $CaCl_2$, 1 mmole $MgCl_2$, 0.6 umole c-di-GMP, and 60 umole UDPG to a final volume of 61 ml) were gently layered on it. The tubes were incubated for 15 min at 30° C., then placed on ice for 2.5 hr, and finally centrifuged in a TST-28 Contron rotor for 30 min at 20,000 rpm. (The centrifuge was set to decelerate to 350 rpm in 3-4 min.) The supernatants were carefully decanted. The pellets were combined and suspended in 15 ml TME with a manual homogenizer and recentrifuged. The final pellet was suspended in 5 ml TME. Before SDS-PAGE, the entrapped enzyme was washed once by centrifugation. The entrapped enzyme was stable for several weeks when frozen and stored as above. The activity yield of entrapped enzyme was about 45%.

1. Separation of Proteins on SDS-PAGE

Entrapped enzyme, containing 12-15% of original cellulose synthase activity, was dissolved in Laemmli's sample buffer (containing DTT), and subjected to SDS-PAGE in 10% acrylamide slab gels. The peptide bands were visualized by Coomassie-Blue staining and excised. Four major bands were observed, Band A 90-95 kd, Band B 65-68 kd, Band C 58-60 kd, and Band D 54-56 kd. The gel slices were sealed in plastic bags containing 10% acetic acid for storage.

Recovery of the Protein from the SDS-PAGE Gel Slices

The proteins were separated from the SDS-PAGE gel slices by electroelution, using a method modified from Hunkapiller, et al. (1983) *Methods in Enzymology*, 91:227-247. The method was adapted to result in a lower final SDS concentration. The modifications were: 1) substitution of elution buffer (0.1% SDS in 0.05M $NH_4HCO_3$) for the soaking buffer (2% SDS in 0.05M $NH_4HCO_3$); and 2) when replacing the elution buffer (0.1% SDS in 0.05M $NH_4HCO_3$) in the apparatus with dialysis buffer (0.02% SDS in 0.01M $NH_4HCO_3$), most of the buffer in the sample cell was also replaced, carefully avoiding disturbing the sample.

EXAMPLE XXI

N-Terminal Amino Acid Sequence of The Polypeptides Protein Isolated From The Cellulose Synthase Preparation The first 18 amino acids of the 90-95 kd protein and the first 16 amino acids of the 65-68 kd protein purified from Acetobacter strain 1306-27 were sequenced by automated Edman degradation on an Applied Biosystems model 470A Protein Sequencer, using the reagents and protocol supplied by the manufacturer. The 18 amino acids of the 90-95 kd protein match an amino acid sequence predicted from the DNA sequence of cellulose synthase obtained as described above. The match begins with the alanine residue indicated in FIG. 1. The amino-terminus obtained after purification may not be the actual in vivo N-terminus, but may reflect proteolysis at the lysine preceding this alanine. The deduced sequence of the cloned gene codes for a protein of 83 kd. Some additional peaks for the early amino acids near the N-terminus were present, possibly due to contamination.

The quality of the sequence obtained for the 65-68 kd protein was not as high as that obtained for the 90-95 kd protein, but a good match may be made between the 65-68 kd protein N-terminal sequence and the amino acids (designated by the brackets) from the sequence predicted in FIG. 1. Thus, the 65-68 kd protein appears to be a proteolytic fragment of the 90-95 kd protein.

The following cultures have been deposited at the American Type Culture Collection, (ATCC) Rockville, Md., U.S.A., under the terms of the Budapest Treaty on the International Recognition of the Deposit of Microorganisms for the Purposes of Patent Procedure and Regulations thereunder (Budapest Treaty) and are thus maintained and made available according to the terms of The Budapest Treaty. Availability of such strains is not to be construed as a license to practice the invention in contravention of the rights granted under the authority of any government in accordance with its patent laws.

The deposited cultures have been assigned the indicated ATCC deposit numbers. The cultures have also been deposited with the Master Culture Collection (CMCC) of Cetus Corporation, Emeryville, Calif., U.S.A., the assignee of the present application, and assigned the indicated CMCC deposit numbers:

| Culture | CMCC No. | ATCC No. |
|---|---|---|
| Acetobacter 1306-24 pUC18-824 FS6 | 3538 | 67925 |
| E. coli DG101 pUC18-824 FS6 | 3581 | 67926 |
| Acetobacter strain 1306-3 | 1909 | 53264 |
| Acetobacter strain 1306-11 | 2145 | 53263 |
| Acetobacter strain 1306-21 | 2618 | 53524 |
| E. coli DG98 | 1965 | 39768 |
| E. coli DG101 pUC18-824 pABCD | | 68264 |

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 9540 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: join(328..2589, 2594..4999, 5005..8961, 8964..9431)
        ( D ) OTHER INFORMATION:

( x i ) SEQUENCE DESCRIPTION: SEQ ID NO:1:

```
GGCTGGCCGC  CCCGTGCCGA  CCGACAACTC  CCCGACCCTG  ACCGAAGTGT  TCATGACCCT        60

TGGTGGTCGG  GCCACGGACC  GGTTGGTGCC  CAAGCCCAGC  CTGCGCGATG  CCCTGTTGCG       120

CAAGCGTGAA  GACGCGAACG  GCGACTCCTG  AAACCGTGCC  GGGGGCGACC  TGCTCCCGGC       180

ATGTCAGAGG  AAAGAAGGGG  GAAGGTTTTC  CCCGCCCCGC  ATCGCTGCGG  GCCGAAAGGC       240

GACATGACGG  ACCGAATGCG  TCTGACGGTT  TTCTTTTGAA  TATATAACGA  CCTGTTTTAC       300

CAGTATTTAT  TATCGGACGA  GCTATTG ATG TCA GAG GTT CAG TCG CCA GTA              351
                               Met Ser Glu Val Gln Ser Pro Val
                                1               5

CCC GCG GAG AGT AGG CTA GAC CGC TTT TCC AAC AAG ATA CTG TCA CTG             399
Pro Ala Glu Ser Arg Leu Asp Arg Phe Ser Asn Lys Ile Leu Ser Leu
        10                  15                  20

CGT GGG GCC AAC TAT ATA GTT GGA GCG CTG GGG CTT TGT GCA CTT ATC             447
Arg Gly Ala Asn Tyr Ile Val Gly Ala Leu Gly Leu Cys Ala Leu Ile
 25                  30                  35                  40

GCC GCA ACC ACG GTC ACG CTG TCC ATT AAT GAG CAG CTG ATT GTG GCA             495
Ala Ala Thr Thr Val Thr Leu Ser Ile Asn Glu Gln Leu Ile Val Ala
                 45                  50                  55

CTT GTG TGT GTG CTC GTC TTT TTT ATT GTC GGG CGC GGC AAG AGC CGC             543
Leu Val Cys Val Leu Val Phe Phe Ile Val Gly Arg Gly Lys Ser Arg
                 60                  65                  70

CGC ACC CAG ATC TTT CTC GAG GTG CTC TCG GCG CTG GTC TCC CTG CGT             591
Arg Thr Gln Ile Phe Leu Glu Val Leu Ser Ala Leu Val Ser Leu Arg
         75                  80                  85

TAC CTG ACA TGG CGC CTG ACC GAA ACG TTG GAC TTC GAT ACA TGG ATT             639
Tyr Leu Thr Trp Arg Leu Thr Glu Thr Leu Asp Phe Asp Thr Trp Ile
         90                  95                 100

CAG GGC GGG CTG GGC GTG ACC CTG CTC ATG GCC GAA CTC TAT GCC CTG             687
```

```
Gln Gly Gly Leu Gly Val Thr Leu Leu Met Ala Glu Leu Tyr Ala Leu
105                     110                 115                 120

TAC ATG CTG TTT CTC AGC TAT TTC CAG ACA ATC CAG CCA CTT CAT CGC    735
Tyr Met Leu Phe Leu Ser Tyr Phe Gln Thr Ile Gln Pro Leu His Arg
            125                 130                 135

GCG CCG CTG CCC CTG CCG GAC AAT GTT GAT GAC TGG CCA ACC GTC GAC    783
Ala Pro Leu Pro Leu Pro Asp Asn Val Asp Asp Trp Pro Thr Val Asp
                140                 145                 150

ATC TTC ATC CCG ACC TAT GAT GAA CAG CTC AGC ATC GTG CGC CTG ACC    831
Ile Phe Ile Pro Thr Tyr Asp Glu Gln Leu Ser Ile Val Arg Leu Thr
        155                 160                 165

GTG CTG GGC GCG CTG GGC ATC GAC TGG CCG CCC GAT AAA GTG AAT GTC    879
Val Leu Gly Ala Leu Gly Ile Asp Trp Pro Pro Asp Lys Val Asn Val
    170                 175                 180

TAT ATC CTT GAT GAT GGT GTG CGC CCC GAA TTT GAA CAG TTT GCC AAG    927
Tyr Ile Leu Asp Asp Gly Val Arg Pro Glu Phe Glu Gln Phe Ala Lys
185                 190                 195                 200

GAT TGC GGC GCT CTC TAC ATC GGG CGC GTC GAC AGT TCA CAC GCC AAG    975
Asp Cys Gly Ala Leu Tyr Ile Gly Arg Val Asp Ser Ser His Ala Lys
            205                 210                 215

GCG GGT AAC CTC AAC CAC GCC ATT AAG CGG ACA AGC GGC GAT TAC ATC    1023
Ala Gly Asn Leu Asn His Ala Ile Lys Arg Thr Ser Gly Asp Tyr Ile
                220                 225                 230

CTC ATC CTG GAT TGT GAC CAT ATT CCG ACA CGC GCG TTC CTG CAG ATC    1071
Leu Ile Leu Asp Cys Asp His Ile Pro Thr Arg Ala Phe Leu Gln Ile
        235                 240                 245

GCG ATG GGC TGG ATG GTC GCA GAC CGC AAG ATC GCC CTG ATG CAG ACG    1119
Ala Met Gly Trp Met Val Ala Asp Arg Lys Ile Ala Leu Met Gln Thr
    250                 255                 260

CCG CAT CAC TTC TAC TCC CCC GAT CCG TTC CAG CGT AAC TTG GCC GTG    1167
Pro His His Phe Tyr Ser Pro Asp Pro Phe Gln Arg Asn Leu Ala Val
265                 270                 275                 280

GGG TAT CGC ACC CCG CCG GAA GGC AAC CTG TTC TAC GGC GTC ATT CAG    1215
Gly Tyr Arg Thr Pro Pro Glu Gly Asn Leu Phe Tyr Gly Val Ile Gln
            285                 290                 295

GAT GGT AAC GAC TTC TGG GAT GCC ACC TTC TTC TGC GGC TCG TGC GCC    1263
Asp Gly Asn Asp Phe Trp Asp Ala Thr Phe Phe Cys Gly Ser Cys Ala
                300                 305                 310

ATC CTG CGG CGT GAA GCC ATT GAA TCG ATC GGC GGC TTC GCG GTT GAA    1311
Ile Leu Arg Arg Glu Ala Ile Glu Ser Ile Gly Gly Phe Ala Val Glu
        315                 320                 325

ACC GTG ACG GAA GAT GCC CAT ACC GCC CTG CGC ATG CAG CGC CGT GGC    1359
Thr Val Thr Glu Asp Ala His Thr Ala Leu Arg Met Gln Arg Arg Gly
    330                 335                 340

TGG TCC ACC GCC TAC CTG CGC ATT CCC GTT GCC AGT GGA CTG GCC ACC    1407
Trp Ser Thr Ala Tyr Leu Arg Ile Pro Val Ala Ser Gly Leu Ala Thr
345                 350                 355                 360

GAG CGA CTG ACA ACC CAT ATC GGC CAG CGC ATG CGC TGG GCA CGC GGC    1455
Glu Arg Leu Thr Thr His Ile Gly Gln Arg Met Arg Trp Ala Arg Gly
            365                 370                 375

ATG ATC CAG ATC TTC CGC GTG GAC AAC CCG ATG CTC GGG GGC GGC CTG    1503
Met Ile Gln Ile Phe Arg Val Asp Asn Pro Met Leu Gly Gly Gly Leu
                380                 385                 390

AAG CTT GGG CAG CGG CTG TGC TAT CTC TCG GCC ATG ACG TCG TTC TTC    1551
Lys Leu Gly Gln Arg Leu Cys Tyr Leu Ser Ala Met Thr Ser Phe Phe
        395                 400                 405

TTC GCC ATT CCG CGC GTC ATC TTC CTT GCC TCG CCG CTG GCG TTC CTG    1599
Phe Ala Ile Pro Arg Val Ile Phe Leu Ala Ser Pro Leu Ala Phe Leu
    410                 415                 420

TTT TTC GGC CAG AAC ATC ATC GCC GCC TCG CCG CTG GCC GTG CTG GCC    1647
Phe Phe Gly Gln Asn Ile Ile Ala Ala Ser Pro Leu Ala Val Leu Ala
425                 430                 435                 440
```

| | |
|---|---|
| TAC GCC ATT CCG CAC ATG TTC CAC TCC ATC GCG ACC GCC GCC AAG GTG<br>Tyr Ala Ile Pro His Met Phe His Ser Ile Ala Thr Ala Ala Lys Val<br>445 450 455 | 1695 |
| AAC AAG GGC TGG CGC TAT TCG TTC TGG AGT GAA GTG TAC GAA ACC ACC<br>Asn Lys Gly Trp Arg Tyr Ser Phe Trp Ser Glu Val Tyr Glu Thr Thr<br>460 465 470 | 1743 |
| ATG GCG CTG TTC CTG GTG CGC GTA ACC ATC ATC ACC CTG ATG TTC CCC<br>Met Ala Leu Phe Leu Val Arg Val Thr Ile Ile Thr Leu Met Phe Pro<br>475 480 485 | 1791 |
| TCC AAG GGC AAG TTC AAC GTG ACG GAA AAG GGT GGC GTG CTG GAG GAG<br>Ser Lys Gly Lys Phe Asn Val Thr Glu Lys Gly Gly Val Leu Glu Glu<br>490 495 500 | 1839 |
| GAA GAG TTC GAC CTT GGC GCG ACC TAC CCC AAC ATC ATT TTT GCC GGC<br>Glu Glu Phe Asp Leu Gly Ala Thr Tyr Pro Asn Ile Ile Phe Ala Gly<br>505 510 515 520 | 1887 |
| ATC ATG ACG TTG GGG CTG CTG ATC GGT CTG TTC GAA CTG ACC TTC CAC<br>Ile Met Thr Leu Gly Leu Leu Ile Gly Leu Phe Glu Leu Thr Phe His<br>525 530 535 | 1935 |
| TTC AAC CAG CTC GCG GGC ATT GCC AAG CGT GCT TAC CTG CTG AAC TGC<br>Phe Asn Gln Leu Ala Gly Ile Ala Lys Arg Ala Tyr Leu Leu Asn Cys<br>540 545 550 | 1983 |
| ATC TGG GCG ATG ATC AGT CTC ATC ATC CTC CTT GCC GCC ATT GCC GTG<br>Ile Trp Ala Met Ile Ser Leu Ile Ile Leu Leu Ala Ala Ile Ala Val<br>555 560 565 | 2031 |
| GGG CGT GAG ACC AAG CAG GTC CGT TAC AAC CAT CGT GTC GAG GCG CAT<br>Gly Arg Glu Thr Lys Gln Val Arg Tyr Asn His Arg Val Glu Ala His<br>570 575 580 | 2079 |
| ATC CCG GTA ACG GTT TAT GAA GCA CCG GTC GCG GGG CAG CCC AAT ACC<br>Ile Pro Val Thr Val Tyr Glu Ala Pro Val Ala Gly Gln Pro Asn Thr<br>585 590 595 600 | 2127 |
| TAC CAT AAT GCG ACA CCG GGC ATG ACC CAG GAT GTC TCC ATG GGT GGC<br>Tyr His Asn Ala Thr Pro Gly Met Thr Gln Asp Val Ser Met Gly Gly<br>605 610 615 | 2175 |
| GTT GCC GTC CAC ATG CCC TGG CCA GAT GTC AGC ACA GGA CCA GTC AAG<br>Val Ala Val His Met Pro Trp Pro Asp Val Ser Thr Gly Pro Val Lys<br>620 625 630 | 2223 |
| ACA CGC ATT CAT GCC GTG CTC GAT GGC GAG GAG ATC GAT ATT CCC GCC<br>Thr Arg Ile His Ala Val Leu Asp Gly Glu Glu Ile Asp Ile Pro Ala<br>635 640 645 | 2271 |
| ACC ATG CTG CGC TGC AAG AAT GGC AAG GCC GTG TTC ACA TGG GAC AAT<br>Thr Met Leu Arg Cys Lys Asn Gly Lys Ala Val Phe Thr Trp Asp Asn<br>650 655 660 | 2319 |
| AAT GAC CTT GAT ACG GAA CGC GAT ATT GTC CGC TTC GTG TTC GGG CGG<br>Asn Asp Leu Asp Thr Glu Arg Asp Ile Val Arg Phe Val Phe Gly Arg<br>665 670 675 680 | 2367 |
| GCC GAT GCC TGG CTG CAA TGG AAT AAT TAT GAG GAT GAC AGA CCG CTA<br>Ala Asp Ala Trp Leu Gln Trp Asn Asn Tyr Glu Asp Asp Arg Pro Leu<br>685 690 695 | 2415 |
| CGC AGT CTG TGG AGC CTG CTG CTC AGC ATT AAG GCG CTG TTC CGC AAA<br>Arg Ser Leu Trp Ser Leu Leu Leu Ser Ile Lys Ala Leu Phe Arg Lys<br>700 705 710 | 2463 |
| AAA GGC AAA ATG ATG GCC AAT AGT CGT CCA AAA AGA AAA CCA CTT GCC<br>Lys Gly Lys Met Met Ala Asn Ser Arg Pro Lys Arg Lys Pro Leu Ala<br>715 720 725 | 2511 |
| CTA CCG GTT GAG CGC AGG GAG CCC ACA ACC ATC CAG AGT GGA CAG ACA<br>Leu Pro Val Glu Arg Arg Glu Pro Thr Thr Ile Gln Ser Gly Gln Thr<br>730 735 740 | 2559 |
| CAG GAA GGA AAG ATC AGC CGT GCG GCC TCG TGAT ATG AAA ATG GTG TCC<br>Gln Glu Gly Lys Ile Ser Arg Ala Ala Ser Met Lys Met Val Ser<br>745 750 755 | 2608 |
| CTG ATC GCG CTG CTG GTC TTT GCA ACG GGC GCA CAG GCT GCG CCT GTT | 2656 |

```
Leu Ile Ala Leu Leu Val Phe Ala Thr Gly Ala Gln Ala Ala Pro Val
760             765             770             775

GCC TCC AAG GCA CCA GCC CCG CAG CCC GCA GGC TCA GAC CTG CCG CCC      2704
Ala Ser Lys Ala Pro Ala Pro Gln Pro Ala Gly Ser Asp Leu Pro Pro
            780             785             790

CTG CCT GCC GCG GCA TCG CAG GCT GCC ACG CCC GCT GCG GCA AGC GCG      2752
Leu Pro Ala Ala Ala Ser Gln Ala Ala Thr Pro Ala Ala Ala Ser Ala
            795             800             805

GAC CAG CCC GCC ACA ACC GCC CCG GCG GCG GAT GCC GCA TCA GCC AGT      2800
Asp Gln Pro Ala Thr Thr Ala Pro Ala Ala Asp Ala Ala Ser Ala Ser
            810             815             820

GCG GCT GAT GCG GTC GTG GAT AAT GCC GAG AAC GCC ATT GCC GCG TCT      2848
Ala Ala Asp Ala Val Val Asp Asn Ala Glu Asn Ala Ile Ala Ala Ser
            825             830             835

GAC GTG GCA ACG GTG CAT ACA TAC TCC CTC AAG GAG CTC GGT GCG CAG      2896
Asp Val Ala Thr Val His Thr Tyr Ser Leu Lys Glu Leu Gly Ala Gln
840             845             850             855

AGT GCC CTG AAA ATG CAG GGC GCC GCC ACG CTG CAG GGC CTG CAG TTC      2944
Ser Ala Leu Lys Met Gln Gly Ala Ala Thr Leu Gln Gly Leu Gln Phe
                860             865             870

GGC ATT CCG GCC GAC CAG CTG GTC ACG TCG GCA CGG CTT ATC GTG TCT      2992
Gly Ile Pro Ala Asp Gln Leu Val Thr Ser Ala Arg Leu Ile Val Ser
            875             880             885

GGA GCG ATG TCG CCC AGC CTC CAG CCT GAT ACC AGC GCG GTC ACG ATC      3040
Gly Ala Met Ser Pro Ser Leu Gln Pro Asp Thr Ser Ala Val Thr Ile
            890             895             900

ACG CTG AAC GAG CAG TTC ATC GGC ACG CTA CGC CCG GAC CCC ACC CAT      3088
Thr Leu Asn Glu Gln Phe Ile Gly Thr Leu Arg Pro Asp Pro Thr His
    905             910             915

CCT ACA TTT GGG CCG CTC TCG TTT GAT ATC AAC CCC ATC TTC TTC ATC      3136
Pro Thr Phe Gly Pro Leu Ser Phe Asp Ile Asn Pro Ile Phe Phe Ile
920             925             930             935

ACG GGC AAC CGG CTG AAC TTC AGC TTC GCT TCA AGC TCG AAG GGC TGC      3184
Thr Gly Asn Arg Leu Asn Phe Ser Phe Ala Ser Ser Ser Lys Gly Cys
            940             945             950

ACG GAC CCC AGC AAC GGA TTG CTC TGG GCC AGC GTG TCC GAA CAT TCC      3232
Thr Asp Pro Ser Asn Gly Leu Leu Trp Ala Ser Val Ser Glu His Ser
            955             960             965

GAA CTG CAG ATC ACC ACC ATA CCG CTT CCC CCG CGT CGT CAG CTC TCG      3280
Glu Leu Gln Ile Thr Thr Ile Pro Leu Pro Pro Arg Arg Gln Leu Ser
            970             975             980

CGC CTG CCC CAG CCG TTC TTC GAC AAG AAC GTA AAG CAG AAG ATC GTC      3328
Arg Leu Pro Gln Pro Phe Phe Asp Lys Asn Val Lys Gln Lys Ile Val
            985             990             995

ATT CCG TTC GTT CTT GCA CAG ACA TTT GAT CCC GAA GTG CTG AAG GCG      3376
Ile Pro Phe Val Leu Ala Gln Thr Phe Asp Pro Glu Val Leu Lys Ala
1000            1005            1010            1015

ACC GGC ATC CTG GCA TCG TGG TTC GGC CAG CAG ACC GAT TTC CGT GGC      3424
Thr Gly Ile Leu Ala Ser Trp Phe Gly Gln Gln Thr Asp Phe Arg Gly
            1020            1025            1030

GTT ACC TTC CCG GTC TTC TCC ACC ATT CCG CAA ACG GGC AAT GCC GTT      3472
Val Thr Phe Pro Val Phe Ser Thr Ile Pro Gln Thr Gly Asn Ala Val
            1035            1040            1045

GTC GTT GGC GTG GCT GAT GAA CTG CCT TCC GCC CTC GGG CGC CAG GCG      3520
Val Val Gly Val Ala Asp Glu Leu Pro Ser Ala Leu Gly Arg Gln Ala
            1050            1055            1060

GTC AAT GGC CCC ACG CTT ATG GAA GTG GCC AAT CCA TCC GAC CCC AAC      3568
Val Asn Gly Pro Thr Leu Met Glu Val Ala Asn Pro Ser Asp Pro Asn
            1065            1070            1075

GGC ACG GTG CTG CTC GTA ACG GGG CGT GAC CGT GAT GAA GTC ATC ACC      3616
Gly Thr Val Leu Leu Val Thr Gly Arg Asp Arg Asp Glu Val Ile Thr
1080            1085            1090            1095
```

| | | | | | | | | | | | | | | | | |
|---|---|---|---|---|---|---|---|---|---|---|---|---|---|---|---|---|
| GCG | AGC | AAG | GGC | ATC | GGC | TTT | GGC | TCG | AGC | GCC | CTG | CCA | ACA | GCC | AAC | 3664 |
| Ala | Ser | Lys | Gly | Ile | Gly | Phe | Gly | Ser | Ser | Ala | Leu | Pro | Thr | Ala | Asn | |
| | | | 1100 | | | | 1105 | | | | | 1110 | | | | |
| CGC | ATG | GAC | GTG | GCG | CCG | ATT | GAT | GTG | GGC | GCG | CGT | GTG | GCC | TAT | GAC | 3712 |
| Arg | Met | Asp | Val | Ala | Pro | Ile | Asp | Val | Gly | Ala | Arg | Val | Ala | Tyr | Asp | |
| | | | 1115 | | | | 1120 | | | | | 1125 | | | | |
| GCG | CCC | TCC | TTC | ATT | CCC | ACC | AAC | CGT | CCG | GTC | CGC | CTT | GGC | GAA | CTG | 3760 |
| Ala | Pro | Ser | Phe | Ile | Pro | Thr | Asn | Arg | Pro | Val | Arg | Leu | Gly | Glu | Leu | |
| | | | 1130 | | | | 1135 | | | | | 1140 | | | | |
| GTG | CCA | GAC | AGC | GCC | CTG | CAG | GCC | CAG | GGA | TAC | GCG | CCG | GGC | GCA | CTC | 3808 |
| Val | Pro | Asp | Ser | Ala | Leu | Gln | Ala | Gln | Gly | Tyr | Ala | Pro | Gly | Ala | Leu | |
| | | | 1145 | | | | 1150 | | | | | 1155 | | | | |
| TCG | GTG | CCG | TTC | CGT | GTC | TCG | CCC | GAT | CTG | TAT | ACC | TGG | CGT | GAT | CGA | 3856 |
| Ser | Val | Pro | Phe | Arg | Val | Ser | Pro | Asp | Leu | Tyr | Thr | Trp | Arg | Asp | Arg | |
| 1160 | | | | | 1165 | | | | | 1170 | | | | | 1175 | |
| CCG | TAC | AAG | CTG | AAC | GTC | CGT | TTC | CGC | GCA | CCG | CCA | GGA | CCG | ATT | GTC | 3904 |
| Pro | Tyr | Lys | Leu | Asn | Val | Arg | Phe | Arg | Ala | Pro | Pro | Gly | Pro | Ile | Val | |
| | | | 1180 | | | | 1185 | | | | | 1190 | | | | |
| GAT | GTG | TCG | CGC | TCG | TCT | CTC | AAC | GTC | GGT | ATC | AAC | GAT | ACC | TAT | CTT | 3952 |
| Asp | Val | Ser | Arg | Ser | Ser | Leu | Asn | Val | Gly | Ile | Asn | Asp | Thr | Tyr | Leu | |
| | | | 1195 | | | | 1200 | | | | | 1205 | | | | |
| GAG | GCC | TAT | CCG | CTG | CGT | GAG | CCG | GAT | TCA | ACG | CTG | GAC | CAG | ATC | CTG | 4000 |
| Glu | Ala | Tyr | Pro | Leu | Arg | Glu | Pro | Asp | Ser | Thr | Leu | Asp | Gln | Ile | Leu | |
| | | | 1210 | | | | 1215 | | | | | 1220 | | | | |
| CGG | CGC | GTG | GGC | CTG | GGC | CGT | GGC | GAT | GAC | AGC | GTG | CAG | AAG | CAC | ACC | 4048 |
| Arg | Arg | Val | Gly | Leu | Gly | Arg | Gly | Asp | Asp | Ser | Val | Gln | Lys | His | Thr | |
| | | | 1225 | | | | 1230 | | | | | 1235 | | | | |
| ATG | CCC | ATC | CCG | CCC | TAC | CGG | GTT | TTT | GGC | CAG | AAC | CAG | CTT | CTG | TTC | 4096 |
| Met | Pro | Ile | Pro | Pro | Tyr | Arg | Val | Phe | Gly | Gln | Asn | Gln | Leu | Leu | Phe | |
| 1240 | | | | | 1245 | | | | | 1250 | | | | | 1255 | |
| TAT | TTC | GAG | ATG | GCG | GCG | ATG | GCC | GAG | CCG | GGC | TGC | AAA | CCT | GGC | CCG | 4144 |
| Tyr | Phe | Glu | Met | Ala | Ala | Met | Ala | Glu | Pro | Gly | Cys | Lys | Pro | Gly | Pro | |
| | | | 1260 | | | | 1265 | | | | | 1270 | | | | |
| AGC | ACG | TTC | CAT | ATG | AGT | GTT | GAT | CCG | GAT | TCG | ACG | ATC | GAC | CTG | TCC | 4192 |
| Ser | Thr | Phe | His | Met | Ser | Val | Asp | Pro | Asp | Ser | Thr | Ile | Asp | Leu | Ser | |
| | | | 1275 | | | | 1280 | | | | | 1285 | | | | |
| AAC | TCC | TAT | CAT | ATC | ACG | CGC | ATG | CCC | AAC | CTC | GCC | TTC | ATG | GCC | AGT | 4240 |
| Asn | Ser | Tyr | His | Ile | Thr | Arg | Met | Pro | Asn | Leu | Ala | Phe | Met | Ala | Ser | |
| | | | 1290 | | | | 1295 | | | | | 1300 | | | | |
| GCG | GGC | TAT | CCG | TTC | ACG | ACC | TAT | GCC | GAC | CTG | TCG | CGC | TCG | GCC | GTG | 4288 |
| Ala | Gly | Tyr | Pro | Phe | Thr | Thr | Tyr | Ala | Asp | Leu | Ser | Arg | Ser | Ala | Val | |
| | | | 1305 | | | | 1310 | | | | | 1315 | | | | |
| GTG | CTG | CCC | GAC | CAC | CCC | AAT | GGC | ATG | GTC | GTC | AGC | GCC | TAT | CTT | GAT | 4336 |
| Val | Leu | Pro | Asp | His | Pro | Asn | Gly | Met | Val | Val | Ser | Ala | Tyr | Leu | Asp | |
| 1320 | | | | | 1325 | | | | | 1330 | | | | | 1335 | |
| CTC | ATG | GGC | TTC | ATG | GGC | GCG | ACG | ACA | TGG | TAT | CCG | GTG | TCC | GGC | GTG | 4384 |
| Leu | Met | Gly | Phe | Met | Gly | Ala | Thr | Thr | Trp | Tyr | Pro | Val | Ser | Gly | Val | |
| | | | 1340 | | | | 1345 | | | | | 1350 | | | | |
| GAT | GTG | GTC | TCG | AGC | GAC | CAT | GTA | AAT | GAT | GTG | GCG | GAC | CGG | AAC | CTG | 4432 |
| Asp | Val | Val | Ser | Ser | Asp | His | Val | Asn | Asp | Val | Ala | Asp | Arg | Asn | Leu | |
| | | | 1355 | | | | 1360 | | | | | 1365 | | | | |
| ATT | GTC | CTG | TCC | ACG | CTG | GCC | AAT | AGC | GGC | GAT | GTT | TCG | CAA | CTG | CTG | 4480 |
| Ile | Val | Leu | Ser | Thr | Leu | Ala | Asn | Ser | Gly | Asp | Val | Ser | Gln | Leu | Leu | |
| | | | 1370 | | | | 1375 | | | | | 1380 | | | | |
| AGC | AAA | TCG | TCC | TAT | CAG | ATT | TCT | GAC | GGG | CGG | CTG | CAC | ATG | GGG | CTG | 4528 |
| Ser | Lys | Ser | Ser | Tyr | Gln | Ile | Ser | Asp | Gly | Arg | Leu | His | Met | Gly | Leu | |
| | | | 1385 | | | | 1390 | | | | | 1395 | | | | |
| CGC | TCG | ACG | CTG | AGC | GGC | GTA | TGG | AAC | CTG | TTC | CAG | GAT | CCC | ATG | TCG | 4576 |
| Arg | Ser | Thr | Leu | Ser | Gly | Val | Trp | Asn | Leu | Phe | Gln | Asp | Pro | Met | Ser | |
| 1400 | | | | | 1405 | | | | | 1410 | | | | | 1415 | |
| GGC | ATC | AGC | AAT | ACG | GCC | CCG | ACC | GAT | GTC | GAG | AGC | ACG | CTG | ACC | GGG | 4624 |

-continued

| | |
|---|---|
| Gly Ile Ser Asn Thr Ala Pro Thr Asp Val Glu Ser Thr Leu Thr Gly<br>1420                          1425                  1430 | |
| GGG GTA GCC GCG ATG ATC GAG GCA GAA TCG CCT CTG GCA TCA GGC CGG<br>Gly Val Ala Ala Met Ile Glu Ala Glu Ser Pro Leu Ala Ser Gly Arg<br>1435                   1440                 1445 | 4672 |
| ACC GTG CTC GCG CTG CTT TCG GGT GAC GGG CAG GGG CTC AAC AAT CTT<br>Thr Val Leu Ala Leu Leu Ser Gly Asp Gly Gln Gly Leu Asn Asn Leu<br>1450                   1455               1460 | 4720 |
| GTG CAG ATC CTC GCA CAG CGT AAA AAC CAG GCC AAG ATC CAG GGC GAC<br>Val Gln Ile Leu Ala Gln Arg Lys Asn Gln Ala Lys Ile Gln Gly Asp<br>1465                   1470               1475 | 4768 |
| CTT GTG CTG GCG CAT GGC GAT GAT CTG ACA TCC TAC CGG AGT TCG CCG<br>Leu Val Leu Ala His Gly Asp Asp Leu Thr Ser Tyr Arg Ser Ser Pro<br>1480                   1485               1490               1495 | 4816 |
| CTG TAT ACG GTT GGC ACC GTG CCG CTG TGG CTC GAG CCT GAC TGG TAT<br>Leu Tyr Thr Val Gly Thr Val Pro Leu Trp Leu Glu Pro Asp Trp Tyr<br>1500                   1505               1510 | 4864 |
| ATG CAC AAC CAC CCC AGC CGC GTG ATC GTG GTG GGC CTG CTC GGG TGC<br>Met His Asn His Pro Ser Arg Val Ile Val Val Gly Leu Leu Gly Cys<br>1515                   1520               1525 | 4912 |
| ATT CTG ATT GTG GCC GTC ATG GTG CGC GCC CTG GCC AAG CAT GCT CTG<br>Ile Leu Ile Val Ala Val Met Val Arg Ala Leu Ala Lys His Ala Leu<br>1530                   1535               1540 | 4960 |
| CGC CGC CGT CGT GAG CTG CAG GAA GAA AGG CAG AGA ACG TGATC ATG<br>Arg Arg Arg Arg Glu Leu Gln Glu Glu Arg Gln Arg Thr      Met<br>1545                   1550               1555 | 5007 |
| AAC AGG CGA TAC GTC CTT TCG CTT TCT GGT GCC CTG CTG GCC AGC AGT<br>Asn Arg Arg Tyr Val Leu Ser Leu Ser Gly Ala Leu Leu Ala Ser Ser<br>1560                   1565               1570 | 5055 |
| TGC ATG ACG GTG CTG GTG GCG GTT CCT GTT GCG CGG GCG CAG CAG GCT<br>Cys Met Thr Val Leu Val Ala Val Pro Val Ala Arg Ala Gln Gln Ala<br>1575                   1580               1585 | 5103 |
| TCC ACC GCC ATG ACC ACC GCT GCC ACG AGC GCG ACT GCG GCA CCA CGG<br>Ser Thr Ala Met Thr Thr Ala Ala Thr Ser Ala Thr Ala Ala Pro Arg<br>1590                   1595               1600               1605 | 5151 |
| CAG ATC CTG TTG CAG CAG GCA CGC TTC TGG CTT CAG CAG CAG CAG TAT<br>Gln Ile Leu Leu Gln Gln Ala Arg Phe Trp Leu Gln Gln Gln Gln Tyr<br>1610                   1615               1620 | 5199 |
| GAC AAT GCC CGC CAG GCC TTG CAG AAC GCG GAG CGC ATC GCC CCC AAT<br>Asp Asn Ala Arg Gln Ala Leu Gln Asn Ala Glu Arg Ile Ala Pro Asn<br>1625                   1630               1635 | 5247 |
| TCC CCT GAC GTG CTG GAA GTG CTG GGT GAA TAC CAG ACG GCC ATT GGC<br>Ser Pro Asp Val Leu Glu Val Leu Gly Glu Tyr Gln Thr Ala Ile Gly<br>1640                   1645               1650 | 5295 |
| AAC CGC GAA GCC GCC GCC GAT ACG CTG CGC CAC CTG CAG CAG GTG GCG<br>Asn Arg Glu Ala Ala Ala Asp Thr Leu Arg His Leu Gln Gln Val Ala<br>1655                   1660               1665 | 5343 |
| CCG GGC AGT GCC GCG GCA GGT AAC CTG AAT GAC CTG CTC AGC GAG CGG<br>Pro Gly Ser Ala Ala Ala Gly Asn Leu Asn Asp Leu Leu Ser Glu Arg<br>1670                   1675               1680               1685 | 5391 |
| GCC ATC TCC CAA AGC GAC CTG TCG CAG ATC CGC' TCG CTG GCG GGT TCG<br>Ala Ile Ser Gln Ser Asp Leu Ser Gln Ile Arg Ser Leu Ala Gly Ser<br>1690                   1695               1700 | 5439 |
| GGC CAG AAC GCG CAG GCG GTG GCG GGC TAC CAG AAG CTG TTC CAC GGT<br>Gly Gln Asn Ala Gln Ala Val Ala Gly Tyr Gln Lys Leu Phe His Gly<br>1705                   1710               1715 | 5487 |
| GGC AAG CCG CCG CAT TCG CTC GCG GTG GAA TAC TAC CAG ACC ATG GCG<br>Gly Lys Pro Pro His Ser Leu Ala Val Glu Tyr Tyr Gln Thr Met Ala<br>1720                   1725               1730 | 5535 |
| GGC GTG CCG GCC CAG TGG GAC CAG GCC CGC GCC GGG CTT GCC GGG GTC<br>Gly Val Pro Ala Gln Trp Asp Gln Ala Arg Ala Gly Leu Ala Gly Val<br>1735                   1740               1745 | 5583 |

```
GTT GCG TCA AAC CCG CAG GAT TAC CGC GCC CAG CTC GCC TTT GCC CAG      5631
Val Ala Ser Asn Pro Gln Asp Tyr Arg Ala Gln Leu Ala Phe Ala Gln
1750                1755                1760                1765

GCC CTG ACC TAT AAT ACC TCG ACC CGC ATG GAA GGC CTG ACC CGG CTC      5679
Ala Leu Thr Tyr Asn Thr Ser Thr Arg Met Glu Gly Leu Thr Arg Leu
            1770                1775                1780

AAG GAT CTC CAG TCC TTC CGC AGC CAG GCC CCG GTC GAG GCG GCC GCC      5727
Lys Asp Leu Gln Ser Phe Arg Ser Gln Ala Pro Val Glu Ala Ala Ala
        1785                1790                1795

GCG GCG CAG TCC TAC CGC CAG ACC CTG AGC TGG CTG CCG GTC AAT CCT      5775
Ala Ala Gln Ser Tyr Arg Gln Thr Leu Ser Trp Leu Pro Val Asn Pro
    1800                1805                1810

GAG ACG CAG CCC CTC ATG GAG CAG TGG CTT TCC GCC CAC CCC AAT GAT      5823
Glu Thr Gln Pro Leu Met Glu Gln Trp Leu Ser Ala His Pro Asn Asp
1815                1820                1825

ACC GCG CTG CGC GAG CAT ATG CTC CAC CCC CCC GGT GGT CCG CCG GAC      5871
Thr Ala Leu Arg Glu His Met Leu His Pro Pro Gly Gly Pro Pro Asp
1830                1835                1840                1845

AAG GCC GGG CTT GCG CGC CAG GCA GGT TAC CAG CAG CTT AAC GCG GGC      5919
Lys Ala Gly Leu Ala Arg Gln Ala Gly Tyr Gln Gln Leu Asn Ala Gly
            1850                1855                1860

CGT CTT GCC GCA GCC GAG CAG TCT TTC CAG TCG GCG TTG CAG ATC AAT      5967
Arg Leu Ala Ala Ala Glu Gln Ser Phe Gln Ser Ala Leu Gln Ile Asn
            1865                1870                1875

TCC CAT GAT GCT GAT TCG CTT GGT GGC ATG GGG CTC GTA AGC ATG CGG      6015
Ser His Asp Ala Asp Ser Leu Gly Gly Met Gly Leu Val Ser Met Arg
        1880                1885                1890

CAG GGC GAT ACC GCG GAG GCG CGC CGC TAT TTT GAA GAA GCG ATG GCC      6063
Gln Gly Asp Thr Ala Glu Ala Arg Arg Tyr Phe Glu Glu Ala Met Ala
1895                1900                1905

GCC GAC CCC AAG ACC GCC GAT CGC TGG CGC CCG GCG CTT GCG GGC ATG      6111
Ala Asp Pro Lys Thr Ala Asp Arg Trp Arg Pro Ala Leu Ala Gly Met
1910                1915                1920                1925

GCC GTC AGC GGC GAG TAT GCT TCC GTT CGC CAG TTG ATT GCC GCC CAT      6159
Ala Val Ser Gly Glu Tyr Ala Ser Val Arg Gln Leu Ile Ala Ala His
            1930                1935                1940

CAA TAT ACC GAG GCC AAG CAG CAG CTT GCC ACG CTG GCC CGC CAG CCC      6207
Gln Tyr Thr Glu Ala Lys Gln Gln Leu Ala Thr Leu Ala Arg Gln Pro
        1945                1950                1955

GGC CAG TAT ACT GGC GCG ACC CTC ATG CTG GCC GAC CTG CAG CGC TCG      6255
Gly Gln Tyr Thr Gly Ala Thr Leu Met Leu Ala Asp Leu Gln Arg Ser
    1960                1965                1970

ACC GGC CAG ATT GCC GCC GCC GAG CAG GAA TAT CGT GGC ATC CTG TCG      6303
Thr Gly Gln Ile Ala Ala Ala Glu Gln Glu Tyr Arg Gly Ile Leu Ser
1975                1980                1985

CGT GAG CCC AAT AAC CAG TTG GCC CTC ATG GGG CTG GCC CGG GTA GAC      6351
Arg Glu Pro Asn Asn Gln Leu Ala Leu Met Gly Leu Ala Arg Val Asp
1990                1995                2000                2005

ATG GCG CAG GGC AAC ACG GCG GAA GCA CGC CAG CTC CTG TCG CGT GTC      6399
Met Ala Gln Gly Asn Thr Ala Glu Ala Arg Gln Leu Leu Ser Arg Val
            2010                2015                2020

GGC CCG CAA TAT GCA AGC CAG GTG GGC GAG ATC GAG GTT TCG GGC CTG      6447
Gly Pro Gln Tyr Ala Ser Gln Val Gly Glu Ile Glu Val Ser Gly Leu
            2025                2030                2035

ATG GCG GCT GCG TCC CAG ACA TCG GAT TCA GCG CGC AAG GTT TCC ATC      6495
Met Ala Ala Ala Ser Gln Thr Ser Asp Ser Ala Arg Lys Val Ser Ile
            2040                2045                2050

CTG CGC GAA GCG ATG GCC CAG GCC CCA CGT GAC CCC TGG GTG CGC ATC      6543
Leu Arg Glu Ala Met Ala Gln Ala Pro Arg Asp Pro Trp Val Arg Ile
    2055                2060                2065

AAC CTT GCC AAT GCG CTG CAG CAG CAG GGC GAC GTG GCC GAA GCC GGG      6591
```

|  |  |
|---|---:|
| Asn Leu Ala Asn Ala Leu Gln Gln Gln Gly Asp Val Ala Glu Ala Gly<br>2070                         2075                      2080                      2085 |  |
| CGC GTG ATG CAG CCC ATC CTG GCC AAT CCC GTC ACC GCG CAG GAC CGC<br>Arg Val Met Gln Pro Ile Leu Ala Asn Pro Val Thr Ala Gln Asp Arg<br>                2090                     2095                     2100 | 6639 |
| CAG GCC GGT ATC CTT TAT ACC TAT GGT AGT GGC AAT GAT GCG ATG ACC<br>Gln Ala Gly Ile Leu Tyr Thr Tyr Gly Ser Gly Asn Asp Ala Met Thr<br>                2105                     2110                     2115 | 6687 |
| CGC CAG CTT CTG GCT GGT CTG TCG CCT GCG GAT TAT TCT CCT GCC ATC<br>Arg Gln Leu Leu Ala Gly Leu Ser Pro Ala Asp Tyr Ser Pro Ala Ile<br>          2120                     2125                     2130 | 6735 |
| CGT TCC ATC GCC GAG GAA ATG GAA ATC AAG CAG GAT CTG GCC AGC CGC<br>Arg Ser Ile Ala Glu Glu Met Glu Ile Lys Gln Asp Leu Ala Ser Arg<br>             2135                     2140                     2145 | 6783 |
| CTG TCC ATG GTG TCC AAC CCG GTG CCG CTG ATC CGC GAG GCC CTG ACC<br>Leu Ser Met Val Ser Asn Pro Val Pro Leu Ile Arg Glu Ala Leu Thr<br>2150                         2155                      2160                      2165 | 6831 |
| CAG CCT GAT CCG ACC GGC GCG CGC GGC GTG GCG GTG GCT GAC CTG TTC<br>Gln Pro Asp Pro Thr Gly Ala Arg Gly Val Ala Val Ala Asp Leu Phe<br>                2170                     2175                     2180 | 6879 |
| CGC CAG CGT GGC GAC ATG GTG CAT GCC CGC ATG GCA CTG CGT ATC GCC<br>Arg Gln Arg Gly Asp Met Val His Ala Arg Met Ala Leu Arg Ile Ala<br>             2185                     2190                     2195 | 6927 |
| TCG ACG CGC ACC ATC GAT CTC TCG CCC GAC CAG CGC CTG TCC TAT GCC<br>Ser Thr Arg Thr Ile Asp Leu Ser Pro Asp Gln Arg Leu Ser Tyr Ala<br>        2200                     2205                     2210 | 6975 |
| ACC GAA TAC ATG AAG ATC AGC AAC CCG GTG GCC GCT GCG CGG CTG CTG<br>Thr Glu Tyr Met Lys Ile Ser Asn Pro Val Ala Ala Ala Arg Leu Leu<br>2215                         2220                      2225 | 7023 |
| GCC CCG CTG GGG GAT GGC ACG GGC TCG GCT ACA GGA AGC GCG TTG CTG<br>Ala Pro Leu Gly Asp Gly Thr Gly Ser Ala Thr Gly Ser Ala Leu Leu<br>2230                         2235                      2240                      2245 | 7071 |
| CCC GAG CAG GTG CAG ACG CTC CAG CAA CTG CGC ATG GGC ATC TCG GTG<br>Pro Glu Gln Val Gln Thr Leu Gln Gln Leu Arg Met Gly Ile Ser Val<br>             2250                     2255                     2260 | 7119 |
| GCG CAG TCC GAT CTG CTC AAC CAG CGT GGC GAC CAG GCG CAG GCC TAT<br>Ala Gln Ser Asp Leu Leu Asn Gln Arg Gly Asp Gln Ala Gln Ala Tyr<br>          2265                     2270                     2275 | 7167 |
| GAT CAT CTG GCC CCC GCG CTG CAG GCC GAC CCG GAG GCG ACA TCG CCC<br>Asp His Leu Ala Pro Ala Leu Gln Ala Asp Pro Glu Ala Thr Ser Pro<br>             2280                     2285                     2290 | 7215 |
| AAG CTG GCG CTC GCG CGG CTG TAT AAT GGC CAC GGC AAG CCG GGC AAG<br>Lys Leu Ala Leu Ala Arg Leu Tyr Asn Gly His Gly Lys Pro Gly Lys<br>        2295                     2300                     2305 | 7263 |
| GCG CTC GAG ATC GAC CTT GCG GTG CTG CGC CAC AAC CCG CAG GAC CTT<br>Ala Leu Glu Ile Asp Leu Ala Val Leu Arg His Asn Pro Gln Asp Leu<br>2310                         2315                      2320                      2325 | 7311 |
| GAT GCG CGA CAG GCT GCG GTG CAG GCG GCG GTC AAC AGC GAC CAC AAC<br>Asp Ala Arg Gln Ala Ala Val Gln Ala Ala Val Asn Ser Asp His Asn<br>             2330                     2335                     2340 | 7359 |
| AGC CTT GCC ACC CGC CTT GCC ATG GAT GGC GTG CAG GAA AGC CCG ATG<br>Ser Leu Ala Thr Arg Leu Ala Met Asp Gly Val Gln Glu Ser Pro Met<br>                2345                     2350                     2355 | 7407 |
| GAT GCC CGT GCC TGG CTG GCC ATG GCC GTG GCT GAC CAG GCC GAT GGC<br>Asp Ala Arg Ala Trp Leu Ala Met Ala Val Ala Asp Gln Ala Asp Gly<br>          2360                     2365                     2370 | 7455 |
| CAC GGG CAG CGC ACC ATC GAG GAT CTG CGC CGC GCC TAT GAC CTG CGC<br>His Gly Gln Arg Thr Ile Glu Asp Leu Arg Arg Ala Tyr Asp Leu Arg<br>             2375                     2380                     2385 | 7503 |
| CTG CAG CAG GTC GAG GGC ACG CGG GCC GCG TCT GGC GCG GGT GCT GCG<br>Leu Gln Gln Val Glu Gly Thr Arg Ala Ala Ser Gly Ala Gly Ala Ala<br>2390                         2395                      2400                      2405 | 7551 |

| | |
|---|---|
| CAG GAA GAT GCG CTT GCT CCG CCC TCG ACC AAC CCG TTC CGC CCG CGT<br>Gln Glu Asp Ala Leu Ala Pro Pro Ser Thr Asn Pro Phe Arg Pro Arg<br>2410 2415 2420 | 7599 |
| GGC TAC GGC CAC CAG ACG GAA CTT GGC GCG CCT GTG ACC GGT GGC TCC<br>Gly Tyr Gly His Gln Thr Glu Leu Gly Ala Pro Val Thr Gly Gly Ser<br>2425 2430 2435 | 7647 |
| TAC AGC GCC GAG GCG GCA TCG CCC GAT ACG TCG GAC CAG ATG CTC TCC<br>Tyr Ser Ala Glu Ala Ala Ser Pro Asp Thr Ser Asp Gln Met Leu Ser<br>2440 2445 2450 | 7695 |
| TCC ATC GCA GGC CAG ATC CGC ACG CTG CGT GAG AAC CTT GCC CCT TCC<br>Ser Ile Ala Gly Gln Ile Arg Thr Leu Arg Glu Asn Leu Ala Pro Ser<br>2455 2460 2465 | 7743 |
| ATC GAT GGT GGC CTC GGG TTC CGC TCG CGT TCG GGT GAG CAT GGC ATG<br>Ile Asp Gly Gly Leu Gly Phe Arg Ser Arg Ser Gly Glu His Gly Met<br>2470 2475 2480 2485 | 7791 |
| GGC CGC CTG ACG GAA GCG AAC ATT CCC ATC GTG GGC CGC CTG CCG CTG<br>Gly Arg Leu Thr Glu Ala Asn Ile Pro Ile Val Gly Arg Leu Pro Leu<br>2490 2495 2500 | 7839 |
| CAG GCC GGT GCT TCC GCC CTG ACC TTC TCG ATC ACG CCA ACC ATG ATC<br>Gln Ala Gly Ala Ser Ala Leu Thr Phe Ser Ile Thr Pro Thr Met Ile<br>2505 2510 2515 | 7887 |
| TGG TCG GGC AAC CTC AAC ACG GGT TCC GTC TAT GAT GTG CCG CGT TAT<br>Trp Ser Gly Asn Leu Asn Thr Gly Ser Val Tyr Asp Val Pro Arg Tyr<br>2520 2525 2530 | 7935 |
| GGC ACG ATG ATG GGC GTG CAG GCA TAT AAC CAG TAC GAT AGC TAT ACC<br>Gly Thr Met Met Gly Val Gln Ala Tyr Asn Gln Tyr Asp Ser Tyr Thr<br>2535 2540 2545 | 7983 |
| AAC GCG GGC AGG GAC CAG CAG CGC ATC GCC GCT GGC ACG GCC GAG GCC<br>Asn Ala Gly Arg Asp Gln Gln Arg Ile Ala Ala Gly Thr Ala Glu Ala<br>2550 2555 2560 2565 | 8031 |
| GGG TTT GCG CCG GAT GTG CAG TTT GGC AAT AGC TGG GTG CGG GCC GAT<br>Gly Phe Ala Pro Asp Val Gln Phe Gly Asn Ser Trp Val Arg Ala Asp<br>2570 2575 2580 | 8079 |
| GTG GGT GCG TCG CCC ATC GGC TTC CCC ATC ACC AAC GTG CTG GGC GGT<br>Val Gly Ala Ser Pro Ile Gly Phe Pro Ile Thr Asn Val Leu Gly Gly<br>2585 2590 2595 | 8127 |
| GTC GAG TTC TCG CCG CGC GTG GGT CCG GTC ACC TTC CGT GTC AGT GCC<br>Val Glu Phe Ser Pro Arg Val Gly Pro Val Thr Phe Arg Val Ser Ala<br>2600 2605 2610 | 8175 |
| GAG CGC CGG TCG ATC ACC AAC AGC GTG CTG TCC TAT GGC GGC CTG CGT<br>Glu Arg Arg Ser Ile Thr Asn Ser Val Leu Ser Tyr Gly Gly Leu Arg<br>2615 2620 2625 | 8223 |
| GAC ACG AAC TAC AAC AGC GCG CTT GGC CGG TAT GCC CGC CAG GTC TAC<br>Asp Thr Asn Tyr Asn Ser Ala Leu Gly Arg Tyr Ala Arg Gln Val Tyr<br>2630 2635 2640 2645 | 8271 |
| GGC CAG GCA CTG TCC AAG CAG TGG GGC AGC GAA TGG GGT GGC GTC GTG<br>Gly Gln Ala Leu Ser Lys Gln Trp Gly Ser Glu Trp Gly Gly Val Val<br>2650 2655 2660 | 8319 |
| ACC AAC CAC TTC CAT GGG CAG GTC GAG GCG ACA CTG GGC AAC ACC ATC<br>Thr Asn His Phe His Gly Gln Val Glu Ala Thr Leu Gly Asn Thr Ile<br>2665 2670 2675 | 8367 |
| CTG TAT GGT GGC GGT GGC TAC GCA ATC CAG ACC GGC AAG AAC GTG CAG<br>Leu Tyr Gly Gly Gly Gly Tyr Ala Ile Gln Thr Gly Lys Asn Val Gln<br>2680 2685 2690 | 8415 |
| CGC AAC AGC GAG CGT GAA GCG GGC ATC GGC GCC AAT ACG CTG GTG TGG<br>Arg Asn Ser Glu Arg Glu Ala Gly Ile Gly Ala Asn Thr Leu Val Trp<br>2695 2700 2705 | 8463 |
| CAT AAC GCC AAC ATG CTG GTG CGC ATT GGC GTG AGC CTG ACC TAT TTC<br>His Asn Ala Asn Met Leu Val Arg Ile Gly Val Ser Leu Thr Tyr Phe<br>2710 2715 2720 2725 | 8511 |
| GGT TAT GCC AAG AAC GAG GAT TTC TAC ACC TAC GGG CAG GGT GGT TAC | 8559 |

```
         Gly Tyr Ala Lys Asn Glu Asp Phe Tyr Thr Tyr Gly Gln Gly Gly Tyr
                     2730                2735                2740

TTC TCG CCG CAA TCC TAT TAC GCG GCG ACC GTG CCG GTG CGC TAT GCG         8607
Phe Ser Pro Gln Ser Tyr Tyr Ala Ala Thr Val Pro Val Arg Tyr Ala
            2745                2750                2755

GGC CAG CAC AAG CGG CTG GAC TGG GAC GTG ACG GGC AGC GTG GGC TAC         8655
Gly Gln His Lys Arg Leu Asp Trp Asp Val Thr Gly Ser Val Gly Tyr
            2760                2765                2770

CAG GTG TTC CAC GAG CAC TCG GCG CCC TTC TTC CCC ACG TCA TCG CTG         8703
Gln Val Phe His Glu His Ser Ala Pro Phe Phe Pro Thr Ser Ser Leu
    2775                2780                2785

CTG CAG TCC GGC GCC AAT ACC ATC GCG TCG AAT TAC TCG GCG AGC GCC         8751
Leu Gln Ser Gly Ala Asn Thr Ile Ala Ser Asn Tyr Ser Ala Ser Ala
2790                2795                2800                2805

ACG CCG GCG GAA TAT CTG TCG GAG GAA ACG GTG AAC AGC GCC TAC TAT         8799
Thr Pro Ala Glu Tyr Leu Ser Glu Glu Thr Val Asn Ser Ala Tyr Tyr
            2810                2815                2820

CCT GGG GAT AGT ATT GCT GGT CTT ACC GGT GGC TTT AAT GCT AGG GTG         8847
Pro Gly Asp Ser Ile Ala Gly Leu Thr Gly Gly Phe Asn Ala Arg Val
            2825                2830                2835

GGT TAT CGC TTT ACA CGC AAT GTT CGT CTT GAT CTC TCG GGG CGC TAT         8895
Gly Tyr Arg Phe Thr Arg Asn Val Arg Leu Asp Leu Ser Gly Arg Tyr
            2840                2845                2850

CAG AAG GCC GGT AAC TGG ACT GAA AGC GGC GCC ATG ATT TCC GCA CAC         8943
Gln Lys Ala Gly Asn Trp Thr Glu Ser Gly Ala Met Ile Ser Ala His
            2855                2860                2865

TAT CTT ATT ATG GAC CAG TA ATG ACA ACT TTG AAC GCA AAA CCG GAC          8990
Tyr Leu Ile Met Asp Gln     Met Thr Thr Leu Asn Ala Lys Pro Asp
2870                2875                2880

TTT TCG CTT TTC CTG CAG GCC CTG TCC TGG GAG ATC GAT GAT CAG GCC         9038
Phe Ser Leu Phe Leu Gln Ala Leu Ser Trp Glu Ile Asp Asp Gln Ala
2885                2890                2895                2900

GGG ATC GAG GTC CGC AAT GAC CTG TTG CGC GAG GTC GGC CGT GGT ATG         9086
Gly Ile Glu Val Arg Asn Asp Leu Leu Arg Glu Val Gly Arg Gly Met
            2905                2910                2915

GCT GGT CGT TTC CAG CCG CCG CTG TGC AAC ACC ATC CAC CAG CTC CAG         9134
Ala Gly Arg Phe Gln Pro Pro Leu Cys Asn Thr Ile His Gln Leu Gln
            2920                2925                2930

ATC GAG CTG AAC GCC CTG CTG GCC ATG ATC AAC TGG GGC TAC GTG AAG         9182
Ile Glu Leu Asn Ala Leu Leu Ala Met Ile Asn Trp Gly Tyr Val Lys
            2935                2940                2945

CTG GAC CTG CTG GCG GAA GAA CAG GCC ATG CGC ATC GTG CAT GAA GAC         9230
Leu Asp Leu Leu Ala Glu Glu Gln Ala Met Arg Ile Val His Glu Asp
    2950                2955                2960

CTG CCT CAG GTG GGC AGC GCA GGC GAG CCC GCC GGC ACG TGG CTT GCC         9278
Leu Pro Gln Val Gly Ser Ala Gly Glu Pro Ala Gly Thr Trp Leu Ala
2965                2970                2975                2980

CCG GTT CTG GAA GGG CTT TAT GGC CGC TGG ATC ACG TCG CAG CCC GGT         9326
Pro Val Leu Glu Gly Leu Tyr Gly Arg Trp Ile Thr Ser Gln Pro Gly
            2985                2990                2995

GCA TTT GGT GAT TAC GTC GTG ACG CGC GAT ATC GAC GCG GAA GAC CTG         9374
Ala Phe Gly Asp Tyr Val Val Thr Arg Asp Ile Asp Ala Glu Asp Leu
            3000                3005                3010

AAC TCG GTT CCG GCC CAG ACG ATC ATC CTT TAC ATG CGC ACC CGC AGC         9422
Asn Ser Val Pro Ala Gln Thr Ile Ile Leu Tyr Met Arg Thr Arg Ser
            3015                3020                3025

GCC GCG ACC TGATTCCTGC CAGTCGCGCC ATTTGCGTCA AAACCCTGCC                 9471
Ala Ala Thr
            3030

TACAGGCGTG TTCATGCCCT GTAGGCAGGG TTTTTGCATA TAGGGTTCCA CTCTTTGCCC       9531

TGTTTTTGC                                                               9540
```

( 2 ) INFORMATION FOR SEQ ID NO:2:

( i ) SEQUENCE CHARACTERISTICS:
        ( A ) LENGTH: 3031 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ser  Glu  Val  Gln  Ser  Pro  Val  Pro  Ala  Glu  Ser  Arg  Leu  Asp  Arg
 1              5                    10                       15

Phe  Ser  Asn  Lys  Ile  Leu  Ser  Leu  Arg  Gly  Ala  Asn  Tyr  Ile  Val  Gly
              20                    25                       30

Ala  Leu  Gly  Leu  Cys  Ala  Leu  Ile  Ala  Ala  Thr  Thr  Val  Thr  Leu  Ser
              35                    40                       45

Ile  Asn  Glu  Gln  Leu  Ile  Val  Ala  Leu  Val  Cys  Val  Leu  Val  Phe  Phe
         50                        55                   60

Ile  Val  Gly  Arg  Gly  Lys  Ser  Arg  Arg  Thr  Gln  Ile  Phe  Leu  Glu  Val
 65                       70                        75                       80

Leu  Ser  Ala  Leu  Val  Ser  Leu  Arg  Tyr  Leu  Thr  Trp  Arg  Leu  Thr  Glu
                   85                   90                        95

Thr  Leu  Asp  Phe  Asp  Thr  Trp  Ile  Gln  Gly  Gly  Leu  Gly  Val  Thr  Leu
              100                    105                      110

Leu  Met  Ala  Glu  Leu  Tyr  Ala  Leu  Tyr  Met  Leu  Phe  Leu  Ser  Tyr  Phe
              115                    120                      125

Gln  Thr  Ile  Gln  Pro  Leu  His  Arg  Ala  Pro  Leu  Pro  Leu  Pro  Asp  Asn
              130                    135                      140

Val  Asp  Asp  Trp  Pro  Thr  Val  Asp  Ile  Phe  Ile  Pro  Thr  Tyr  Asp  Glu
145                      150                       155                      160

Gln  Leu  Ser  Ile  Val  Arg  Leu  Thr  Val  Leu  Gly  Ala  Leu  Gly  Ile  Asp
                   165                  170                       175

Trp  Pro  Pro  Asp  Lys  Val  Asn  Val  Tyr  Ile  Leu  Asp  Asp  Gly  Val  Arg
              180                    185                      190

Pro  Glu  Phe  Glu  Gln  Phe  Ala  Lys  Asp  Cys  Gly  Ala  Leu  Tyr  Ile  Gly
              195                    200                      205

Arg  Val  Asp  Ser  Ser  His  Ala  Lys  Ala  Gly  Asn  Leu  Asn  His  Ala  Ile
210                      215                            220

Lys  Arg  Thr  Ser  Gly  Asp  Tyr  Ile  Leu  Ile  Leu  Asp  Cys  Asp  His  Ile
225                      230                       235                      240

Pro  Thr  Arg  Ala  Phe  Leu  Gln  Ile  Ala  Met  Gly  Trp  Met  Val  Ala  Asp
                   245                  250                       255

Arg  Lys  Ile  Ala  Leu  Met  Gln  Thr  Pro  His  His  Phe  Tyr  Ser  Pro  Asp
              260                    265                      270

Pro  Phe  Gln  Arg  Asn  Leu  Ala  Val  Gly  Tyr  Arg  Thr  Pro  Pro  Glu  Gly
              275                    280                      285

Asn  Leu  Phe  Tyr  Gly  Val  Ile  Gln  Asp  Gly  Asn  Asp  Phe  Trp  Asp  Ala
         290                        295                  300

Thr  Phe  Phe  Cys  Gly  Ser  Cys  Ala  Ile  Leu  Arg  Arg  Glu  Ala  Ile  Glu
305                      310                       315                      320

Ser  Ile  Gly  Gly  Phe  Ala  Val  Glu  Thr  Val  Thr  Glu  Asp  Ala  His  Thr
                   325                  330                       335

Ala  Leu  Arg  Met  Gln  Arg  Arg  Gly  Trp  Ser  Thr  Ala  Tyr  Leu  Arg  Ile
              340                    345                      350

Pro  Val  Ala  Ser  Gly  Leu  Ala  Thr  Glu  Arg  Leu  Thr  Thr  His  Ile  Gly
              355                    360                      365
```

| | | | | | | | | | | | | | | |
|---|---|---|---|---|---|---|---|---|---|---|---|---|---|---|
| Gln | Arg | Met | Arg | Trp | Ala | Arg | Gly | Met | Ile | Gln | Ile | Phe | Arg | Val | Asp |
| | 370 | | | | 375 | | | | | 380 | | | | | |
| Asn | Pro | Met | Leu | Gly | Gly | Gly | Leu | Lys | Leu | Gly | Gln | Arg | Leu | Cys | Tyr |
| 385 | | | | | 390 | | | | | 395 | | | | | 400 |
| Leu | Ser | Ala | Met | Thr | Ser | Phe | Phe | Phe | Ala | Ile | Pro | Arg | Val | Ile | Phe |
| | | | | 405 | | | | | 410 | | | | | 415 | |
| Leu | Ala | Ser | Pro | Leu | Ala | Phe | Leu | Phe | Phe | Gly | Gln | Asn | Ile | Ile | Ala |
| | | | 420 | | | | | 425 | | | | | 430 | | |
| Ala | Ser | Pro | Leu | Ala | Val | Leu | Ala | Tyr | Ala | Ile | Pro | His | Met | Phe | His |
| | | | 435 | | | | | 440 | | | | | 445 | | |
| Ser | Ile | Ala | Thr | Ala | Ala | Lys | Val | Asn | Lys | Gly | Trp | Arg | Tyr | Ser | Phe |
| | 450 | | | | | 455 | | | | | 460 | | | | |
| Trp | Ser | Glu | Val | Tyr | Glu | Thr | Thr | Met | Ala | Leu | Phe | Leu | Val | Arg | Val |
| 465 | | | | | 470 | | | | | 475 | | | | | 480 |
| Thr | Ile | Ile | Thr | Leu | Met | Phe | Pro | Ser | Lys | Gly | Lys | Phe | Asn | Val | Thr |
| | | | | 485 | | | | | 490 | | | | | 495 | |
| Glu | Lys | Gly | Gly | Val | Leu | Glu | Glu | Glu | Phe | Asp | Leu | Gly | Ala | Thr | |
| | | | 500 | | | | | 505 | | | | | 510 | | |
| Tyr | Pro | Asn | Ile | Ile | Phe | Ala | Gly | Ile | Met | Thr | Leu | Gly | Leu | Leu | Ile |
| | | | 515 | | | | | 520 | | | | | 525 | | |
| Gly | Leu | Phe | Glu | Leu | Thr | Phe | His | Phe | Asn | Gln | Leu | Ala | Gly | Ile | Ala |
| | 530 | | | | | 535 | | | | | 540 | | | | |
| Lys | Arg | Ala | Tyr | Leu | Leu | Asn | Cys | Ile | Trp | Ala | Met | Ile | Ser | Leu | Ile |
| 545 | | | | | 550 | | | | | 555 | | | | | 560 |
| Ile | Leu | Leu | Ala | Ala | Ile | Ala | Val | Gly | Arg | Glu | Thr | Lys | Gln | Val | Arg |
| | | | | 565 | | | | | 570 | | | | | 575 | |
| Tyr | Asn | His | Arg | Val | Glu | Ala | His | Ile | Pro | Val | Thr | Val | Tyr | Glu | Ala |
| | | | 580 | | | | | 585 | | | | | 590 | | |
| Pro | Val | Ala | Gly | Gln | Pro | Asn | Thr | Tyr | His | Asn | Ala | Thr | Pro | Gly | Met |
| | | 595 | | | | | 600 | | | | | 605 | | | |
| Thr | Gln | Asp | Val | Ser | Met | Gly | Gly | Val | Ala | Val | His | Met | Pro | Trp | Pro |
| | 610 | | | | | 615 | | | | | 620 | | | | |
| Asp | Val | Ser | Thr | Gly | Pro | Val | Lys | Thr | Arg | Ile | His | Ala | Val | Leu | Asp |
| 625 | | | | | 630 | | | | | 635 | | | | | 640 |
| Gly | Glu | Glu | Ile | Asp | Ile | Pro | Ala | Thr | Met | Leu | Arg | Cys | Lys | Asn | Gly |
| | | | | 645 | | | | | 650 | | | | | 655 | |
| Lys | Ala | Val | Phe | Thr | Trp | Asp | Asn | Asn | Asp | Leu | Asp | Thr | Glu | Arg | Asp |
| | | | 660 | | | | | 665 | | | | | 670 | | |
| Ile | Val | Arg | Phe | Val | Phe | Gly | Arg | Ala | Asp | Ala | Trp | Leu | Gln | Trp | Asn |
| | | 675 | | | | | 680 | | | | | 685 | | | |
| Asn | Tyr | Glu | Asp | Asp | Arg | Pro | Leu | Arg | Ser | Leu | Trp | Ser | Leu | Leu | Leu |
| | 690 | | | | | 695 | | | | | 700 | | | | |
| Ser | Ile | Lys | Ala | Leu | Phe | Arg | Lys | Lys | Gly | Lys | Met | Met | Ala | Asn | Ser |
| 705 | | | | | 710 | | | | | 715 | | | | | 720 |
| Arg | Pro | Lys | Arg | Lys | Pro | Leu | Ala | Leu | Pro | Val | Glu | Arg | Arg | Glu | Pro |
| | | | | 725 | | | | | 730 | | | | | 735 | |
| Thr | Thr | Ile | Gln | Ser | Gly | Gln | Thr | Gln | Glu | Gly | Lys | Ile | Ser | Arg | Ala |
| | | | 740 | | | | | 745 | | | | | 750 | | |
| Ala | Ser | Met | Lys | Met | Val | Ser | Leu | Ile | Ala | Leu | Leu | Val | Phe | Ala | Thr |
| | | | 755 | | | | | 760 | | | | | 765 | | |
| Gly | Ala | Gln | Ala | Ala | Pro | Val | Ala | Ser | Lys | Ala | Pro | Ala | Pro | Gln | Pro |
| | 770 | | | | | 775 | | | | | 780 | | | | |
| Ala | Gly | Ser | Asp | Leu | Pro | Pro | Leu | Pro | Ala | Ala | Ala | Ser | Gln | Ala | Ala |
| 785 | | | | | 790 | | | | | 795 | | | | | 800 |
| Thr | Pro | Ala | Ala | Ala | Ser | Ala | Asp | Gln | Pro | Ala | Thr | Thr | Ala | Pro | Ala |

-continued

|     |     | 805 |     |     |     |     | 810 |     |     |     |     | 815 |     |     |
| --- | --- | --- | --- | --- | --- | --- | --- | --- | --- | --- | --- | --- | --- | --- |

Ala Asp Ala Ala Ser Ala Ser Ala Ala Asp Ala Val Val Asp Asn Ala
            820                 825                 830

Glu Asn Ala Ile Ala Ala Ser Asp Val Ala Thr Val His Thr Tyr Ser
        835                 840                 845

Leu Lys Glu Leu Gly Ala Gln Ser Ala Leu Lys Met Gln Gly Ala Ala
    850                 855                 860

Thr Leu Gln Gly Leu Gln Phe Gly Ile Pro Ala Asp Gln Leu Val Thr
865                 870                 875                 880

Ser Ala Arg Leu Ile Val Ser Gly Ala Met Ser Pro Ser Leu Gln Pro
                885                 890                 895

Asp Thr Ser Ala Val Thr Ile Thr Leu Asn Glu Gln Phe Ile Gly Thr
            900                 905                 910

Leu Arg Pro Asp Pro Thr His Pro Thr Phe Gly Pro Leu Ser Phe Asp
        915                 920                 925

Ile Asn Pro Ile Phe Phe Ile Thr Gly Asn Arg Leu Asn Phe Ser Phe
    930                 935                 940

Ala Ser Ser Ser Lys Gly Cys Thr Asp Pro Ser Asn Gly Leu Leu Trp
945                 950                 955                 960

Ala Ser Val Ser Glu His Ser Glu Leu Gln Ile Thr Thr Ile Pro Leu
                965                 970                 975

Pro Pro Arg Arg Gln Leu Ser Arg Leu Pro Gln Pro Phe Phe Asp Lys
            980                 985                 990

Asn Val Lys Gln Lys Ile Val Ile Pro Phe Val Leu Ala Gln Thr Phe
        995                 1000                1005

Asp Pro Glu Val Leu Lys Ala Thr Gly Ile Leu Ala Ser Trp Phe Gly
    1010                1015                1020

Gln Gln Thr Asp Phe Arg Gly Val Thr Phe Pro Val Phe Ser Thr Ile
1025                1030                1035                1040

Pro Gln Thr Gly Asn Ala Val Val Val Gly Val Ala Asp Glu Leu Pro
            1045                1050                1055

Ser Ala Leu Gly Arg Gln Ala Val Asn Gly Pro Thr Leu Met Glu Val
            1060                1065                1070

Ala Asn Pro Ser Asp Pro Asn Gly Thr Val Leu Leu Val Thr Gly Arg
        1075                1080                1085

Asp Arg Asp Glu Val Ile Thr Ala Ser Lys Gly Ile Gly Phe Gly Ser
    1090                1095                1100

Ser Ala Leu Pro Thr Ala Asn Arg Met Asp Val Ala Pro Ile Asp Val
1105                1110                1115                1120

Gly Ala Arg Val Ala Tyr Asp Ala Pro Ser Phe Ile Pro Thr Asn Arg
            1125                1130                1135

Pro Val Arg Leu Gly Glu Leu Val Pro Asp Ser Ala Leu Gln Ala Gln
            1140                1145                1150

Gly Tyr Ala Pro Gly Ala Leu Ser Val Pro Phe Arg Val Ser Pro Asp
        1155                1160                1165

Leu Tyr Thr Trp Arg Asp Arg Pro Tyr Lys Leu Asn Val Arg Phe Arg
    1170                1175                1180

Ala Pro Pro Gly Pro Ile Val Asp Val Ser Arg Ser Ser Leu Asn Val
1185                1190                1195                1200

Gly Ile Asn Asp Thr Tyr Leu Glu Ala Tyr Pro Leu Arg Glu Pro Asp
            1205                1210                1215

Ser Thr Leu Asp Gln Ile Leu Arg Arg Val Gly Leu Gly Arg Gly Asp
            1220                1225                1230

Asp Ser Val Gln Lys His Thr Met Pro Ile Pro Pro Tyr Arg Val Phe
        1235                1240                1245

```
Gly Gln Asn Gln Leu Leu Phe Tyr Phe Glu Met Ala Ala Met Ala Glu
    1250                1255               1260
Pro Gly Cys Lys Pro Gly Pro Ser Thr Phe His Met Ser Val Asp Pro
1265            1270            1275            1280
Asp Ser Thr Ile Asp Leu Ser Asn Ser Tyr His Ile Thr Arg Met Pro
            1285                1290                1295
Asn Leu Ala Phe Met Ala Ser Ala Gly Tyr Pro Phe Thr Thr Tyr Ala
        1300                1305                1310
Asp Leu Ser Arg Ser Ala Val Val Leu Pro Asp His Pro Asn Gly Met
        1315                1320            1325
Val Val Ser Ala Tyr Leu Asp Leu Met Gly Phe Met Gly Ala Thr Thr
    1330                1335            1340
Trp Tyr Pro Val Ser Gly Val Asp Val Val Ser Ser Asp His Val Asn
1345            1350                1355            1360
Asp Val Ala Asp Arg Asn Leu Ile Val Leu Ser Thr Leu Ala Asn Ser
                1365            1370                1375
Gly Asp Val Ser Gln Leu Leu Ser Lys Ser Ser Tyr Gln Ile Ser Asp
            1380            1385                1390
Gly Arg Leu His Met Gly Leu Arg Ser Thr Leu Ser Gly Val Trp Asn
        1395                1400            1405
Leu Phe Gln Asp Pro Met Ser Gly Ile Ser Asn Thr Ala Pro Thr Asp
    1410                1415                1420
Val Glu Ser Thr Leu Thr Gly Gly Val Ala Ala Met Ile Glu Ala Glu
1425            1430                1435                1440
Ser Pro Leu Ala Ser Gly Arg Thr Val Leu Ala Leu Leu Ser Gly Asp
                1445            1450                1455
Gly Gln Gly Leu Asn Asn Leu Val Gln Ile Leu Ala Gln Arg Lys Asn
            1460            1465                1470
Gln Ala Lys Ile Gln Gly Asp Leu Val Leu Ala His Gly Asp Asp Leu
    1475                1480                1485
Thr Ser Tyr Arg Ser Ser Pro Leu Tyr Thr Val Gly Thr Val Pro Leu
    1490                1495            1500
Trp Leu Glu Pro Asp Trp Tyr Met His Asn His Pro Ser Arg Val Ile
1505            1510                1515                1520
Val Val Gly Leu Leu Gly Cys Ile Leu Ile Val Ala Val Met Val Arg
            1525                1530                1535
Ala Leu Ala Lys His Ala Leu Arg Arg Arg Arg Glu Leu Gln Glu Glu
        1540                1545                1550
Arg Gln Arg Thr Met Asn Arg Arg Tyr Val Leu Ser Leu Ser Gly Ala
            1555                1560            1565
Leu Leu Ala Ser Ser Cys Met Thr Val Leu Val Ala Val Pro Val Ala
    1570                1575                1580
Arg Ala Gln Gln Ala Ser Thr Ala Met Thr Thr Ala Ala Thr Ser Ala
1585            1590                1595                1600
Thr Ala Ala Pro Arg Gln Ile Leu Leu Gln Gln Ala Arg Phe Trp Leu
            1605                1610            1615
Gln Gln Gln Gln Tyr Asp Asn Ala Arg Gln Ala Leu Gln Asn Ala Glu
        1620                1625                1630
Arg Ile Ala Pro Asn Ser Pro Asp Val Leu Glu Val Leu Gly Glu Tyr
        1635                1640                1645
Gln Thr Ala Ile Gly Asn Arg Glu Ala Ala Ala Asp Thr Leu Arg His
    1650                1655                1660
Leu Gln Gln Val Ala Pro Gly Ser Ala Ala Ala Gly Asn Leu Asn Asp
1665            1670                1675                1680
```

```
Leu Leu Ser Glu Arg Ala Ile Ser Gln Ser Asp Leu Ser Gln Ile Arg
              1685                1690                1695

Ser Leu Ala Gly Ser Gly Gln Asn Ala Gln Ala Val Ala Gly Tyr Gln
              1700                1705                1710

Lys Leu Phe His Gly Gly Lys Pro Pro His Ser Leu Ala Val Glu Tyr
              1715                1720                1725

Tyr Gln Thr Met Ala Gly Val Pro Ala Gln Trp Asp Gln Ala Arg Ala
              1730                1735                1740

Gly Leu Ala Gly Val Val Ala Ser Asn Pro Gln Asp Tyr Arg Ala Gln
1745                1750                1755                1760

Leu Ala Phe Ala Gln Ala Leu Thr Tyr Asn Thr Ser Thr Arg Met Glu
              1765                1770                1775

Gly Leu Thr Arg Leu Lys Asp Leu Gln Ser Phe Arg Ser Gln Ala Pro
              1780                1785                1790

Val Glu Ala Ala Ala Ala Ala Gln Ser Tyr Arg Gln Thr Leu Ser Trp
              1795                1800                1805

Leu Pro Val Asn Pro Glu Thr Gln Pro Leu Met Glu Gln Trp Leu Ser
              1810                1815                1820

Ala His Pro Asn Asp Thr Ala Leu Arg Glu His Met Leu His Pro Pro
1825                1830                1835                1840

Gly Gly Pro Pro Asp Lys Ala Gly Leu Ala Arg Gln Ala Gly Tyr Gln
              1845                1850                1855

Gln Leu Asn Ala Gly Arg Leu Ala Ala Ala Glu Gln Ser Phe Gln Ser
              1860                1865                1870

Ala Leu Gln Ile Asn Ser His Asp Ala Asp Ser Leu Gly Gly Met Gly
              1875                1880                1885

Leu Val Ser Met Arg Gln Gly Asp Thr Ala Glu Ala Arg Arg Tyr Phe
              1890                1895                1900

Glu Glu Ala Met Ala Ala Asp Pro Lys Thr Ala Asp Arg Trp Arg Pro
1905                1910                1915                1920

Ala Leu Ala Gly Met Ala Val Ser Gly Glu Tyr Ala Ser Val Arg Gln
              1925                1930                1935

Leu Ile Ala Ala His Gln Tyr Thr Glu Ala Lys Gln Gln Leu Ala Thr
              1940                1945                1950

Leu Ala Arg Gln Pro Gly Gln Tyr Thr Gly Ala Thr Leu Met Leu Ala
              1955                1960                1965

Asp Leu Gln Arg Ser Thr Gly Gln Ile Ala Ala Ala Glu Gln Glu Tyr
              1970                1975                1980

Arg Gly Ile Leu Ser Arg Glu Pro Asn Asn Gln Leu Ala Leu Met Gly
1985                1990                1995                2000

Leu Ala Arg Val Asp Met Ala Gln Gly Asn Thr Ala Glu Ala Arg Gln
              2005                2010                2015

Leu Leu Ser Arg Val Gly Pro Gln Tyr Ala Ser Gln Val Gly Glu Ile
              2020                2025                2030

Glu Val Ser Gly Leu Met Ala Ala Ala Ser Gln Thr Ser Asp Ser Ala
              2035                2040                2045

Arg Lys Val Ser Ile Leu Arg Glu Ala Met Ala Gln Ala Pro Arg Asp
              2050                2055                2060

Pro Trp Val Arg Ile Asn Leu Ala Asn Ala Leu Gln Gln Gln Gly Asp
2065                2070                2075                2080

Val Ala Glu Ala Gly Arg Val Met Gln Pro Ile Leu Ala Asn Pro Val
              2085                2090                2095

Thr Ala Gln Asp Arg Gln Ala Gly Ile Leu Tyr Thr Tyr Gly Ser Gly
              2100                2105                2110

Asn Asp Ala Met Thr Arg Gln Leu Leu Ala Gly Leu Ser Pro Ala Asp
```

```
                    2115                    2120                         2125
Tyr  Ser  Pro  Ala  Ile  Arg  Ser  Ile  Ala  Glu  Glu  Met  Glu  Ile  Lys  Gln
              2130                    2135                    2140
Asp  Leu  Ala  Ser  Arg  Leu  Ser  Met  Val  Ser  Asn  Pro  Val  Pro  Leu  Ile
2145                    2150                    2155                         2160
Arg  Glu  Ala  Leu  Thr  Gln  Pro  Asp  Pro  Thr  Gly  Ala  Arg  Gly  Val  Ala
              2165                    2170                         2175
Val  Ala  Asp  Leu  Phe  Arg  Gln  Arg  Gly  Asp  Met  Val  His  Ala  Arg  Met
                   2180                    2185                    2190
Ala  Leu  Arg  Ile  Ala  Ser  Thr  Arg  Thr  Ile  Asp  Leu  Ser  Pro  Asp  Gln
              2195                    2200                    2205
Arg  Leu  Ser  Tyr  Ala  Thr  Glu  Tyr  Met  Lys  Ile  Ser  Asn  Pro  Val  Ala
              2210                    2215                    2220
Ala  Ala  Arg  Leu  Leu  Ala  Pro  Leu  Gly  Asp  Gly  Thr  Gly  Ser  Ala  Thr
2225                    2230                    2235                         2240
Gly  Ser  Ala  Leu  Leu  Pro  Glu  Gln  Val  Gln  Thr  Leu  Gln  Gln  Leu  Arg
              2245                    2250                         2255
Met  Gly  Ile  Ser  Val  Ala  Gln  Ser  Asp  Leu  Leu  Asn  Gln  Arg  Gly  Asp
                   2260                    2265                    2270
Gln  Ala  Gln  Ala  Tyr  Asp  His  Leu  Ala  Pro  Ala  Leu  Gln  Ala  Asp  Pro
              2275                    2280                    2285
Glu  Ala  Thr  Ser  Pro  Lys  Leu  Ala  Leu  Ala  Arg  Leu  Tyr  Asn  Gly  His
              2290                    2295                    2300
Gly  Lys  Pro  Gly  Lys  Ala  Leu  Glu  Ile  Asp  Leu  Ala  Val  Leu  Arg  His
2305                    2310                    2315                         2320
Asn  Pro  Gln  Asp  Leu  Asp  Ala  Arg  Gln  Ala  Ala  Val  Gln  Ala  Ala  Val
              2325                    2330                         2335
Asn  Ser  Asp  His  Asn  Ser  Leu  Ala  Thr  Arg  Leu  Ala  Met  Asp  Gly  Val
              2340                    2345                    2350
Gln  Glu  Ser  Pro  Met  Asp  Ala  Arg  Ala  Trp  Leu  Ala  Met  Ala  Val  Ala
              2355                    2360                    2365
Asp  Gln  Ala  Asp  Gly  His  Gly  Gln  Arg  Thr  Ile  Glu  Asp  Leu  Arg  Arg
              2370                    2375                    2380
Ala  Tyr  Asp  Leu  Arg  Leu  Gln  Gln  Val  Glu  Gly  Thr  Arg  Ala  Ala  Ser
2385                    2390                    2395                         2400
Gly  Ala  Gly  Ala  Ala  Gln  Glu  Asp  Ala  Leu  Ala  Pro  Pro  Ser  Thr  Asn
                   2405                    2410                    2415
Pro  Phe  Arg  Pro  Arg  Gly  Tyr  Gly  His  Gln  Thr  Glu  Leu  Gly  Ala  Pro
              2420                    2425                    2430
Val  Thr  Gly  Gly  Ser  Tyr  Ser  Ala  Glu  Ala  Ala  Ser  Pro  Asp  Thr  Ser
              2435                    2440                    2445
Asp  Gln  Met  Leu  Ser  Ser  Ile  Ala  Gly  Gln  Ile  Arg  Thr  Leu  Arg  Glu
              2450                    2455                    2460
Asn  Leu  Ala  Pro  Ser  Ile  Asp  Gly  Gly  Leu  Gly  Phe  Arg  Ser  Arg  Ser
2465                    2470                    2475                         2480
Gly  Glu  His  Gly  Met  Gly  Arg  Leu  Thr  Glu  Ala  Asn  Ile  Pro  Ile  Val
                   2485                    2490                    2495
Gly  Arg  Leu  Pro  Leu  Gln  Ala  Gly  Ala  Ser  Ala  Leu  Thr  Phe  Ser  Ile
              2500                    2505                    2510
Thr  Pro  Thr  Met  Ile  Trp  Ser  Gly  Asn  Leu  Asn  Thr  Gly  Ser  Val  Tyr
              2515                    2520                    2525
Asp  Val  Pro  Arg  Tyr  Gly  Thr  Met  Met  Gly  Val  Gln  Ala  Tyr  Asn  Gln
              2530                    2535                    2540
Tyr  Asp  Ser  Tyr  Thr  Asn  Ala  Gly  Arg  Asp  Gln  Gln  Arg  Ile  Ala  Ala
2545                    2550                    2555                         2560
```

-continued

```
Gly Thr Ala Glu Ala Gly Phe Ala Pro Asp Val Gln Phe Gly Asn Ser
             2565                2570                2575
Trp Val Arg Ala Asp Val Gly Ala Ser Pro Ile Gly Phe Pro Ile Thr
             2580                2585                2590
Asn Val Leu Gly Gly Val Glu Phe Ser Pro Arg Val Gly Pro Val Thr
             2595                2600                2605
Phe Arg Val Ser Ala Glu Arg Arg Ser Ile Thr Asn Ser Val Leu Ser
             2610                2615                2620
Tyr Gly Gly Leu Arg Asp Thr Asn Tyr Asn Ser Ala Leu Gly Arg Tyr
2625             2630                2635                     2640
Ala Arg Gln Val Tyr Gly Gln Ala Leu Ser Lys Gln Trp Gly Ser Glu
             2645                2650                2655
Trp Gly Gly Val Val Thr Asn His Phe His Gly Gln Val Glu Ala Thr
             2660                2665                2670
Leu Gly Asn Thr Ile Leu Tyr Gly Gly Gly Gly Tyr Ala Ile Gln Thr
             2675                2680                2685
Gly Lys Asn Val Gln Arg Asn Ser Glu Arg Glu Ala Gly Ile Gly Ala
             2690                2695                2700
Asn Thr Leu Val Trp His Asn Ala Asn Met Leu Val Arg Ile Gly Val
2705             2710                2715                     2720
Ser Leu Thr Tyr Phe Gly Tyr Ala Lys Asn Glu Asp Phe Tyr Thr Tyr
             2725                2730                2735
Gly Gln Gly Gly Tyr Phe Ser Pro Gln Ser Tyr Tyr Ala Ala Thr Val
             2740                2745                2750
Pro Val Arg Tyr Ala Gly Gln His Lys Arg Leu Asp Trp Asp Val Thr
             2755                2760                2765
Gly Ser Val Gly Tyr Gln Val Phe His Glu His Ser Ala Pro Phe Phe
             2770                2775                2780
Pro Thr Ser Ser Leu Leu Gln Ser Gly Ala Asn Thr Ile Ala Ser Asn
2785             2790                2795                     2800
Tyr Ser Ala Ser Ala Thr Pro Ala Glu Tyr Leu Ser Glu Glu Thr Val
             2805                2810                2815
Asn Ser Ala Tyr Tyr Pro Gly Asp Ser Ile Ala Gly Leu Thr Gly Gly
             2820                2825                2830
Phe Asn Ala Arg Val Gly Tyr Arg Phe Thr Arg Asn Val Arg Leu Asp
             2835                2840                2845
Leu Ser Gly Arg Tyr Gln Lys Ala Gly Asn Trp Thr Glu Ser Gly Ala
             2850                2855                2860
Met Ile Ser Ala His Tyr Leu Ile Met Asp Gln Met Thr Thr Leu Asn
2865             2870                2875                     2880
Ala Lys Pro Asp Phe Ser Leu Phe Leu Gln Ala Leu Ser Trp Glu Ile
             2885                2890                2895
Asp Asp Gln Ala Gly Ile Glu Val Arg Asn Asp Leu Leu Arg Glu Val
             2900                2905                2910
Gly Arg Gly Met Ala Gly Arg Phe Gln Pro Pro Leu Cys Asn Thr Ile
             2915                2920                2925
His Gln Leu Gln Ile Glu Leu Asn Ala Leu Leu Ala Met Ile Asn Trp
             2930                2935                2940
Gly Tyr Val Lys Leu Asp Leu Leu Ala Glu Glu Gln Ala Met Arg Ile
2945             2950                2955                     2960
Val His Glu Asp Leu Pro Gln Val Gly Ser Ala Gly Glu Pro Ala Gly
             2965                2970                2975
Thr Trp Leu Ala Pro Val Leu Glu Gly Leu Tyr Gly Arg Trp Ile Thr
             2980                2985                2990
```

| Ser | Gln | Pro | Gly | Ala | Phe | Gly | Asp | Tyr | Val | Val | Thr | Arg | Asp | Ile | Asp |
|---|---|---|---|---|---|---|---|---|---|---|---|---|---|---|---|
| | 2995 | | | | | 3000 | | | | | | 3005 | | | |

| Ala | Glu | Asp | Leu | Asn | Ser | Val | Pro | Ala | Gln | Thr | Ile | Ile | Leu | Tyr | Met |
|---|---|---|---|---|---|---|---|---|---|---|---|---|---|---|---|
| 3010 | | | | | 3015 | | | | | 3020 | | | | | |

| Arg | Thr | Arg | Ser | Ala | Ala | Thr |
|---|---|---|---|---|---|---|
| 3025 | | | | 3030 | | |

( 2 ) INFORMATION FOR SEQ ID NO:3:

( i ) SEQUENCE CHARACTERISTICS:
        ( A ) LENGTH: 2262 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
ATGTCAGAGG TTCAGTCGCC AGTACCCGCG GAGAGTAGGC TAGACCGCTT TTCCAACAAG       60
ATACTGTCAC TGCGTGGGGC CAACTATATA GTTGGAGCGC TGGGGCTTTG TGCACTTATC      120
GCCGCAACCA CGGTCACGCT GTCCATTAAT GAGCAGCTGA TTGTGGCACT TGTGTGTGTG      180
CTCGTCTTTT TTATTGTCGG GCGCGGCAAG AGCCGCCGCA CCCAGATCTT TCTCGAGGTG      240
CTCTCGGCGC TGGTCTCCCT GCGTTACCTG ACATGGCGCC TGACCGAAAC GTTGGACTTC      300
GATACATGGA TTCAGGGCGG GCTGGGCGTG ACCCTGCTCA TGGCCGAACT CTATGCCCTG      360
TACATGCTGT TTCTCAGCTA TTTCCAGACA ATCCAGCCAC TTCATCGCGC GCCGCTGCCC      420
CTGCCGGACA ATGTTGATGA CTGGCCAACC GTCGACATCT TCATCCCGAC CTATGATGAA      480
CAGCTCAGCA TCGTGCGCCT GACCGTGCTG GGCGCGCTGG GCATCGACTG GCCGCCCGAT      540
AAAGTGAATG TCTATATCCT TGATGATGGT GTGCGCCCCG AATTTGAACA GTTTGCCAAG      600
GATTGCGGCG CTCTCTACAT CGGGCGCGTC GACAGTTCAC ACGCCAAGGC GGGTAACCTC      660
AACCACGCCA TTAAGCGGAC AAGCGGCGAT TACATCCTCA TCCTGGATTG TGACCATATT      720
CCGACACGCG CGTTCCTGCA GATCGCGATG GGCTGGATGG TCGCAGACCG CAAGATCGCC      780
CTGATGCAGA CGCCGCATCA CTTCTACTCC CCCGATCCGT TCCAGCGTAA CTTGGCCGTG      840
GGGTATCGCA CCCCGCCGGA AGGCAACCTG TTCTACGGCG TCATTCAGGA TGGTAACGAC      900
TTCTGGGATG CCACCTTCTT CTGCGGCTCG TGCGCCATCC TGCGGCGTGA AGCCATTGAA      960
TCGATCGGCG GCTTCGCGGT TGAAACCGTG ACGGAAGATG CCCATACCGC CCTGCGCATG     1020
CAGCGCCGTG GCTGGTCCAC CGCCTACCTG CGCATTCCCG TTGCCAGTGG ACTGGCCACC     1080
GAGCGACTGA CAACCCATAT CGGCCAGCGC ATGCGCTGGG CACGCGGCAT GATCCAGATC     1140
TTCCGCGTGG ACAACCCGAT GCTCGGGGGC GGCCTGAAGC TTGGGCAGCG GCTGTGCTAT     1200
CTCTCGGCCA TGACGTCGTT CTTCTTCGCC ATTCCGCGCG TCATCTTCCT TGCCTCGCCG     1260
CTGGCGTTCC TGTTTTTCGG CCAGAACATC ATCGCCGCCT CGCCGCTGGC CGTGCTGGCC     1320
TACGCCATTC CGCACATGTT CCACTCCATC GCGACGCCCG CCAAGGTGAA CAAGGGCTGG     1380
CGCTATTCGT TCTGGAGTGA AGTGTACGAA ACCACCATGG CGCTGTTCCT GGTGCGCGTA     1440
ACCATCATCA CCCTGATGTT CCCCTCCAAG GGCAAGTTCA ACGTGACGGA AAAGGGTGGC     1500
GTGCTGGAGG AGGAAGAGTT CGACCTTGGC GCGACCTACC CCAACATCAT TTTTGCCGGC     1560
ATCATGACGT TGGGGCTGCT GATCGGTCTG TTCGAACTGA CCTTCCACTT CAACCAGCTC     1620
GCGGGCATTG CCAAGCGTGC CTTACCTGCTG AACTGCATCT GGGCGATGAT CAGTCTCATC     1680
ATCCTCCTTG CCGCCATTGC CGTGGGGCGT GAGACCAAGC AGGTCCGTTA CAACCATCGT     1740
GTCGAGGCGC ATATCCCGGT AACGGTTTAT GAAGCACCGG TCGCGGGGCA GCCCAATACC     1800
```

|            |            |            |            |            |            |      |
|------------|------------|------------|------------|------------|------------|------|
| TACCATAATG | CGACACCGGG | CATGACCCAG | GATGTCTCCA | TGGGTGGCGT | TGCCGTCCAC | 1860 |
| ATGCCCTGGC | CAGATGTCAG | CACAGGACCA | GTCAAGACAC | GCATTCATGC | CGTGCTCGAT | 1920 |
| GGCGAGGAGA | TCGATATTCC | CGCCACCATG | CTGCGCTGCA | AGAATGGCAA | GGCCGTGTTC | 1980 |
| ACATGGGACA | ATAATGACCT | TGATACGGAA | CGCGATATTG | TCCGCTTCGT | GTTCGGGCGG | 2040 |
| GCCGATGCCT | GGCTGCAATG | GAATAATTAT | GAGGATGACA | GACCGCTACG | CAGTCTGTGG | 2100 |
| AGCCTGCTGC | TCAGCATTAA | GGCGCTGTTC | CGCAAAAAAG | GCAAAATGAT | GGCCAATAGT | 2160 |
| CGTCCAAAAA | GAAAACCACT | TGCCCTACCG | GTTGAGCGCA | GGGAGCCCAC | AACCATCCAG | 2220 |
| AGTGGACAGA | CACAGGAAGG | AAAGATCAGC | CGTGCGGCCT | CG         |            | 2262 |

( 2 ) INFORMATION FOR SEQ ID NO:4:

( i ) SEQUENCE CHARACTERISTICS:
        ( A ) LENGTH: 2406 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

|            |            |            |            |            |            |      |
|------------|------------|------------|------------|------------|------------|------|
| ATGAAAATGG | TGTCCCTGAT | CGCGCTGCTG | GTCTTTGCAA | CGGGCGCACA | GGCTGCGCCT | 60   |
| GTTGCCTCCA | AGGCACCAGC | CCCGCAGCCC | GCAGGCTCAG | ACCTGCCGCC | CCTGCCTGCC | 120  |
| GCGGCATCGC | AGGCTGCCAC | GCCCGCTGCG | GCAAGCGCGG | ACCAGCCCGC | CACAACCGCC | 180  |
| CCGGCGGCGG | ATGCCGCATC | AGCCAGTGCG | GCTGATGCGG | TCGTGGATAA | TGCCGAGAAC | 240  |
| GCCATTGCCG | CGTCTGACGT | GGCAACGGTG | CATACATACT | CCCTCAAGGA | GCTCGGTGCG | 300  |
| CAGAGTGCCC | TGAAAATGCA | GGGCGCCGCC | ACGCTGCAGG | GCCTGCAGTT | CGGCATTCCG | 360  |
| GCCGACCAGC | TGGTCACGTC | GGCACGGCTT | ATCGTGTCTG | GAGCGATGTC | GCCCAGCCTC | 420  |
| CAGCCTGATA | CCAGCGCGGT | CACGATCACG | CTGAACGAGC | AGTTCATCGG | CACGCTACGC | 480  |
| CCGGACCCCA | CCCATCCTAC | ATTTGGGCCG | CTCTCGTTTG | ATATCAACCC | CATCTTCTTC | 540  |
| ATCACGGGCA | ACCGGCTGAA | CTTCAGCTTC | GCTTCAAGCT | CGAAGGGCTG | CACGGACCCC | 600  |
| AGCAACGGAT | TGCTCTGGGC | CAGCGTGTCC | GAACATTCCG | AACTGCAGAT | CACCACCATA | 660  |
| CCGCTTCCCC | CGCGTCGTCA | GCTCTCGCGC | CTGCCCCAGC | CGTTCTTCGA | CAAGAACGTA | 720  |
| AAGCAGAAGA | TCGTCATTCC | GTTCGTTCTT | GCACAGACAT | TTGATCCCGA | AGTGCTGAAG | 780  |
| GCGACCGGCA | TCCTGGCATC | GTGGTTCGGC | CAGCAGACCG | ATTTCCGTGG | CGTTACCTTC | 840  |
| CCGGTCTTCT | CCACCATTCC | GCAAACGGGC | AATGCCGTTG | TCGTTGGCGT | GGCTGATGAA | 900  |
| CTGCCTTCCG | CCCTCGGGCG | CCAGGCGGTC | AATGGCCCCA | CGCTTATGGA | AGTGGCCAAT | 960  |
| CCATCCGACC | CCAACGGCAC | GGTGCTGCTC | GTAACGGGGC | GTGACCGTGA | TGAAGTCATC | 1020 |
| ACCGCGAGCA | AGGGCATCGG | CTTTGGCTCG | AGCGCCCTGC | AACAGCCAA  | CCGCATGGAC | 1080 |
| GTGGCGCCGA | TTGATGTGGG | CGCGCGTGTG | GCCTATGACG | CGCCTCCTT  | CATTCCCACC | 1140 |
| AACCGTCCGG | TCCGCCTTGG | CGAACTGGTG | CCAGACAGCG | CCCTGCAGGC | CAGGGATAC  | 1200 |
| GCGCCGGGCG | CACTCTCGGT | GCCGTTCCGT | GTCTCGCCCG | ATCTGTATAC | CTGGCGTGAT | 1260 |
| CGACCGTACA | AGCTGAACGT | CCGTTTCCGC | GCACCGCCAG | GACCGATTGT | CGATGTGTCG | 1320 |
| CGCTCGTCTC | TCAACGTCGG | TATCAACGAT | ACCTATCTTG | AGGCCTATCC | GCTGCGTGAG | 1380 |
| CCGGATTCAA | CGCTGGACCA | GATCCTGCGG | CGCGTGGGCC | TGGGCCGTGG | CGATGACAGC | 1440 |
| GTGCAGAAGC | ACACCATGCC | CATCCCGCCC | TACCGGGTTT | TTGGCCAGAA | CCAGCTTCTG | 1500 |
| TTCTATTTCG | AGATGGCGGC | GATGGCCGAG | CCGGGCTGCA | AACCTGGCCC | GAGCACGTTC | 1560 |
| CATATGAGTG | TTGATCCGGA | TTCGACGATC | GACCTGTCCA | ACTCCTATCA | TATCACGCGC | 1620 |

| | | | | | |
|---|---|---|---|---|---|
| ATGCCCAACC | TCGCCTTCAT | GGCCAGTGCG | GGCTATCCGT | TCACGACCTA | TGCCGACCTG | 1680 |
| TCGCGCTCGG | CCGTGGTGCT | GCCCGACCAC | CCCAATGGCA | TGGTCGTCAG | CGCCTATCTT | 1740 |
| GATCTCATGG | GCTTCATGGG | CGCGACGACA | TGGTATCCGG | TGTCCGGCGT | GGATGTGGTC | 1800 |
| TCGAGCGACC | ATGTAAATGA | TGTGGCGGAC | CGGAACCTGA | TTGTCCTGTC | CACGCTGGCC | 1860 |
| AATAGCGGCG | ATGTTCGCA | ACTGCTGAGC | AAATCGTCCT | ATCAGATTTC | TGACGGGCGG | 1920 |
| CTGCACATGG | GGCTGCGCTC | GACGCTGAGC | GGCGTATGGA | ACCTGTTCCA | GGATCCCATG | 1980 |
| TCGGGCATCA | GCAATACGGC | CCCGACCGAT | GTCGAGAGCA | CGCTGACCGG | GGGGGTAGCC | 2040 |
| GCGATGATCG | AGGCAGAATC | GCCTCTGGCA | TCAGGCCGGA | CCGTGCTCGC | GCTGCTTTCG | 2100 |
| GGTGACGGGC | AGGGGCTCAA | CAATCTTGTG | CAGATCCTCG | CACAGCGTAA | AAACCAGGCC | 2160 |
| AAGATCCAGG | GCGACCTTGT | GCTGGCGCAT | GGCGATGATC | TGACATCCTA | CCGGAGTTCG | 2220 |
| CCGCTGTATA | CGGTTGGCAC | CGTGCCGCTG | TGGCTCGAGC | CTGACTGGTA | TATGCACAAC | 2280 |
| CACCCCAGCC | GCGTGATCGT | GGTGGGCCTG | CTCGGGTGCA | TTCTGATTGT | GGCCGTCATG | 2340 |
| GTGCGCGCCC | TGGCCAAGCA | TGCTCTGCGC | CGCCGTCGTG | AGCTGCAGGA | AGAAAGGCAG | 2400 |
| AGAACG | | | | | | 2406 |

( 2 ) INFORMATION FOR SEQ ID NO:5:

( i ) SEQUENCE CHARACTERISTICS:
       ( A ) LENGTH: 3957 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:5:

| | | | | | |
|---|---|---|---|---|---|
| ATGAACAGGC | GATACGTCCT | TTCGCTTTCT | GGTGCCCTGC | TGGCCAGCAG | TTGCATGACG | 60 |
| GTGCTGGTGG | CGGTTCCTGT | TGCGCGGGCG | CAGCAGGCTT | CCACCGCCAT | GACCACCGCT | 120 |
| GCCACGAGCG | CGACTGCGGC | ACCACGGCAG | ATCCTGTTGC | AGCAGGCACG | CTTCTGGCTT | 180 |
| CAGCAGCAGC | AGTATGACAA | TGCCCGCCAG | GCCTTGCAGA | ACGCGGAGCG | CATCGCCCCC | 240 |
| AATTCCCCTG | ACGTGCTGGA | AGTGCTGGGT | GAATACCAGA | CGGCCATTGG | CAACCGCGAA | 300 |
| GCCGCCGCCG | ATACGCTGCG | CCACCTGCAG | CAGGTGGCGC | CGGGCAGTGC | CGCGGCAGGT | 360 |
| AACCTGAATG | ACCTGCTCAG | CGAGCGGGCC | ATCTCCCAAA | GCGACCTGTC | GCAGATCCGC | 420 |
| TCGCTGGCGG | GTTCGGGCCA | GAACGCGCAG | GCGGTGGCGG | GCTACCAGAA | GCTGTTCCAC | 480 |
| GGTGGCAAGC | CGCCGCATTC | GCTCGCGGTG | GAATACTACC | AGACCATGGC | GGGCGTGCCG | 540 |
| GCCCAGTGGG | ACCAGGCCCG | CGCCGGGCTT | GCCGGGGTCG | TTGCGTCAAA | CCCGCAGGAT | 600 |
| TACCGCGCCC | AGCTCGCCTT | TGCCCAGGCC | CTGACCTATA | ATACCTCGAC | CCGCATGGAA | 660 |
| GGCCTGACCC | GGCTCAAGGA | TCTCCAGTCC | TTCCGCAGCC | AGGCCCCGGT | CGAGGCGGCC | 720 |
| GCCGCGGCGC | AGTCCTACCG | CCAGACCCTG | AGCTGGCTGC | CGGTCAATCC | TGAGACGCAG | 780 |
| CCCCTCATGG | AGCAGTGGCT | TTCCGCCCAC | CCCAATGATA | CCGCGCTGCG | CGAGCATATG | 840 |
| CTCCACCCCC | CCGGTGGTCC | GCCGGACAAG | GCCGGGCTTG | CGCGCCAGGC | AGGTTACCAG | 900 |
| CAGCTTAACG | CGGGCCGTCT | TGCCGCAGCC | GAGCAGTCTT | CCAGTCGGC | GTTGCAGATC | 960 |
| AATTCCCATG | ATGCTGATTC | GCTTGGTGGC | ATGGGGCTCG | TAAGCATGCG | GCAGGGCGAT | 1020 |
| ACCGCGGAGG | CGCGCCGCTA | TTTTGAAGAA | GCGATGGCCG | CCGACCCCAA | GACCGCCGAT | 1080 |
| CGCTGGCGCC | CGGCGCTTGC | GGGCATGGCC | GTCAGCGGCG | AGTATGCTTC | CGTTCGCCAG | 1140 |
| TTGATTGCCG | CCCATCAATA | TACCGAGGCC | AAGCAGCAGC | TTGCCACGCT | GGCCCGCCAG | 1200 |

-continued

```
CCCGGCCAGT ATACTGGCGC GACCCTCATG CTGGCCGACC TGCAGCGCTC GACCGGCCAG    1260
ATTGCCGCCG CCGAGCAGGA ATATCGTGGC ATCCTGTCGC GTGAGCCCAA TAACCAGTTG    1320
GCCCTCATGG GGCTGGCCCG GGTAGACATG GCGCAGGGCA ACACGGCGGA AGCACGCCAG    1380
CTCCTGTCGC GTGTCGGCCC GCAATATGCA AGCCAGGTGG GCGAGATCGA GGTTTCGGGC    1440
CTGATGGCGG CTGCGTCCCA GACATCGGAT TCAGCGCGCA AGGTTTCCAT CCTGCGCGAA    1500
GCGATGGCCC AGGCCCCACG TGACCCCTGG GTGCGCATCA ACCTTGCCAA TGCGCTGCAG    1560
CAGCAGGGCG ACGTGGCCGA AGCCGGGCGC GTGATGCAGC CCATCCTGGC CAATCCCGTC    1620
ACCGCGCAGG ACCGCCAGGC CGGTATCCTT TATACCTATG GTAGTGGCAA TGATGCGATG    1680
ACCCGCCAGC TTCTGGCTGG TCTGTCGCCT GCGGATTATT CTCCTGCCAT CCGTTCCATC    1740
GCCGAGGAAA TGGAAATCAA GCAGGATCTG GCCAGCCGCC TGTCCATGGT GTCCAACCCG    1800
GTGCCGCTGA TCCGCGAGGC CCTGACCCAG CCTGATCCGA CCGGCGCGCG CGGCGTGGCG    1860
GTGGCTGACC TGTTCCGCCA GCGTGGCGAC ATGGTGCATG CCCGCATGGC ACTGCGTATC    1920
GCCTCGACGC GCACCATCGA TCTCTCGCCC GACCAGCGCC TGTCCTATGC CACCGAATAC    1980
ATGAAGATCA GCAACCCGGT GGCCGCTGCG CGGCTGCTGG CCCCGCTGGG GGATGGCACG    2040
GGCTCGGCTA CAGGAAGCGC GTTGCTGCCC GAGCAGGTGC AGACGCTCCA GCAACTGCGC    2100
ATGGGCATCT CGGTGGCGCA GTCCGATCTG CTCAACCAGC GTGGCGACCA GGCGCAGGCC    2160
TATGATCATC TGGCCCCCGC GCTGCAGGCC GACCCGGAGG CGACATCGCC CAAGCTGGCG    2220
CTCGCGCGGC TGTATAATGG CCACGGCAAG CCGGGCAAGG CGCTCGAGAT CGACCTTGCG    2280
GTGCTGCGCC ACAACCCGCA GGACCTTGAT GCGCGACAGG CTGCGGTGCA GGCGGCGGTC    2340
AACAGCGACC ACAACAGCCT TGCCACCCGC CTTGCCATGG ATGGCGTGCA GGAAAGCCCG    2400
ATGGATGCCC GTGCCTGGCT GGCCATGGCC GTGGCTGACC AGGCCGATGG CCACGGGCAG    2460
CGCACCATCG AGGATCTGCG CCGCGCCTAT GACCTGCGCC TGCAGCAGGT CGAGGGCACG    2520
CGGGCCGCGT CTGGCGCGGG TGCTGCGCAG GAAGATGCGC TTGCTCCGCC CTCGACCAAC    2580
CCGTTCCGCC CGCGTGGCTA CGGCCACCAG ACGGAACTTG GCGCGCCTGT GACCGGTGGC    2640
TCCTACAGCG CCGAGGCGGC ATCGCCCGAT ACGTCGGACC AGATGCTCTC CTCCATCGCA    2700
GGCCAGATCC GCACGCTGCG TGAGAACCTT GCCCCTTCCA TCGATGGTGG CCTCGGGTTC    2760
CGCTCGCGTT CGGGTGAGCA TGGCATGGGC CGCCTGACGG AAGCGAACAT TCCCATCGTG    2820
GGCCGCCTGC CGCTGCAGGC CGGTGCTTCC GCCCTGACCT TCTCGATCAC GCCAACCATG    2880
ATCTGGTCGG GCAACCTCAA CACGGGTTCC GTCTATGATG TGCCGCGTTA TGGCACGATG    2940
ATGGGCGTGC AGGCATATAA CCAGTACGAT AGCTATACCA ACGCGGGCAG GGACCAGCAG    3000
CGCATCGCCG CTGGCACGGC CGAGGCCGGG TTTGCGCCGG ATGTGCAGTT TGGCAATAGC    3060
TGGGTGCGGG CCGATGTGGG TGCGTCGCCC ATCGGCTTCC CCATCACCAA CGTGCTGGGC    3120
GGTGTCGAGT TCTCGCCGCG CGTGGGTCCG GTCACCTTCC GTGTCAGTGC CGAGCGCCGG    3180
TCGATCACCA ACAGCGTGCT GTCCTATGGC GGCCTGCGTG ACACGAACTA CAACAGCGCG    3240
CTTGGCCGGT ATGCCCGCCA GGTCTACGGC CAGGCACTGT CCAAGCAGTG GGGCAGCGAA    3300
TGGGGTGGCG TCGTGACCAA CCACTTCCAT GGGCAGGTCG AGGCGACACT GGGCAACACC    3360
ATCCTGTATG GTGGCGGTGG CTACGCAATC CAGACCGGCA AGAACGTGCA GCGCAACAGC    3420
GAGCGTGAAG CGGGCATCGG CGCCAATACG CTGGTGTGGC ATAACGCCAA CATGCTGGTG    3480
CGCATTGGCG TGAGCCTGAC CTATTTCGGT TATGCCAAGA ACGAGGATTT CTACACCTAC    3540
GGGCAGGGTG GTTACTTCTC GCCGCAATCC TATTACGCGG CGACCGTGCC GGTGCGCTAT    3600
GCGGGCCAGC ACAAGCGGCT GGACTGGGAC GTGACGGGCA GCGTGGGCTA CCAGGTGTTC    3660
```

| | | | | | |
|---|---|---|---|---|---|
| CACGAGCACT | CGGCGCCCTT | CTTCCCCACG | TCATCGCTGC | TGCAGTCCGG | CGCCAATACC | 3720
| ATCGCGTCGA | ATTACTCGGC | GAGCGCCACG | CCGGCGGAAT | ATCTGTCGGA | GGAAACGGTG | 3780
| AACAGCGCCT | ACTATCCTGG | GGATAGTATT | GCTGGTCTTA | CCGGTGGCTT | TAATGCTAGG | 3840
| GTGGGTTATC | GCTTTACACG | CAATGTTCGT | CTTGATCTCT | CGGGGCGCTA | TCAGAAGGCC | 3900
| GGTAACTGGA | CTGAAAGCGG | CGCCATGATT | TCCGCACACT | ATCTTATTAT | GGACCAG | 3957

(2) INFORMATION FOR SEQ ID NO:6:

(i) SEQUENCE CHARACTERISTICS:
        (A) LENGTH: 468 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

| | | | | | |
|---|---|---|---|---|---|
| ATGACAACTT | TGAACGCAAA | ACCGGACTTT | TCGCTTTTCC | TGCAGGCCCT | GTCCTGGGAG | 60
| ATCGATGATC | AGGCCGGGAT | CGAGGTCCGC | AATGACCTGT | TGCGCGAGGT | CGGCCGTGGT | 120
| ATGGCTGGTC | GTTTCCAGCC | GCCGCTGTGC | AACACCATCC | ACCAGCTCCA | GATCGAGCTG | 180
| AACGCCCTGC | TGGCCATGAT | CAACTGGGGC | TACGTGAAGC | TGGACCTGCT | GGCGGAAGAA | 240
| CAGGCCATGC | GCATCGTGCA | TGAAGACCTG | CCTCAGGTGG | GCAGCGCAGG | CGAGCCCGCC | 300
| GGCACGTGGC | TTGCCCCGGT | TCTGGAAGGG | CTTTATGGCC | GCTGGATCAC | GTCGCAGCCC | 360
| GGTGCATTTG | GTGATTACGT | CGTGACGCGC | GATATCGACG | CGGAAGACCT | GAACTCGGTT | 420
| CCGGCCCAGA | CGATCATCCT | TTACATGCGC | ACCCGCAGCG | CCGCGACC | | 468

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TGCCCTGGCC AGATGTCAGC A                                              21

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

TGCGGCGATA AGTGCACA                                                  18

(2) INFORMATION FOR SEQ ID NO:9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

-continued

GAATATATAA CGGAGCTCCC GGGATCCACC TGTTTTACC 39

( 2 ) INFORMATION FOR SEQ ID NO:10:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:10:

CGGAGCTCCC GGGATCCAC 19

( 2 ) INFORMATION FOR SEQ ID NO:11:

( i ) SEQUENCE CHARACTERISTICS:
      ( A ) LENGTH: 40 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:11:

GTTCAAGAAT TCCCCGGGAC AACGGTTCTG GCAAATATTC 40

( 2 ) INFORMATION FOR SEQ ID NO:12:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:12:

GTACCGGATC CTGTGTGAAA TTGTTATCCG C 31

( 2 ) INFORMATION FOR SEQ ID NO:13:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:13:

GTTCAAGAAT TCCCCGGGGA CACCATCGAA TGGTGC 36

( 2 ) INFORMATION FOR SEQ ID NO:14:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:14:

GTACCGGATC CGCCGGAAGC ATAAAGTGTA AAG 33

( 2 ) INFORMATION FOR SEQ ID NO:15:

( i ) SEQUENCE CHARACTERISTICS:
      ( A ) LENGTH: 18 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:15:

CAATGTGCCA ATCGCGGG                                                                 18

While the present invention has been illustrated above by certain specific embodiments, it is not intended that these specific examples the scope of the invention as described in the appended claims.

We claim:

1. An isolated polynucleotide acid segment consisting essentially of contiguous nucleic acid sequences encoding a bacterial cellulose synthase operon (SEQ ID No: 1), wherein said polynucleotide acid segment is capable of hybridizing to one or more of the four genes of Sequence ID No: 1 under stringent conditions.

2. The polynucleotide of claim 1 which is derived from the genome of Acetobacter.

3. The polynucleotide of claim 1 which comprises four contiguous genes, wherein, with reference to FIG. 1, the first gene corresponds substantially to nucleotides 328 to 2589, the second gene corresponds substantially to 2594 to 4999, the third gene corresponds substantially to nucleotides 5005 to 8961, and the fourth gene corresponds substantially to nucleotides 8964 to 9431.

4. The polynucleotide of claim 1 which further comprises a DNA sequence encoding a promoter located adjacent to and upstream from the first gene of said operon.

5. The polynucleotide of claim 4 wherein said promoter is endogenous to Acetobacter.

6. The polynucleotide of claim 5 wherein said endogenous promoter is derived from the cellulose synthase operon.

7. The polynucleotide of claim 4 wherein said promoter is a heterologous bacterial promoter.

8. The polynucleotide of claim 7 wherein said heterologous promoter is selected from the group comprising $P_L$, tac and lac.

9. The polynucleotide of claim 1 which further comprises a DNA sequence encoding a transcription terminator.

10. The polynucleotide of claim 1 which is operably linked to a bacterial control sequence for expression.

11. The polynucleotide of claim 10 wherein the bacterial control sequence is selected from the group consisting of Acetobacter, Escherichia and Bacillus.

12. Recombinant bacterial host cells transformed with the polynucleotide of claim 10.

13. The transformed host cell of claim 12 which is an E. coli or Acetobacter cell.

14. An isolated polynucleotide substantially corresponding to the nucleotide segment consisting essentially of the nucleic acid sequence encoding cellulose synthase A (SEQ ID No: 3) wherein said polynucleotide acid segment is capable of hybridizing to the polynucleotide of Sequence ID No: 3 under stringent conditions.

15. The polynucleotide of claim 14 substantially corresponding to nucleotides 328 to 2589 as shown in FIG. 1.

16. An isolated polynucleotide substantially corresponding to the nucleotide segment consisting essentially of the nucleic acid sequence encoding cellulose synthase B (SEQ ID No: 4) wherein said polynucleotide acid segment is capable of hybridizing to the polynucleotide of Sequence ID No: 4 under stringent conditions.

17. The polynucleotide of claim 16 substantially corresponding to nucleotides 2594 and 4999, as shown in FIG. 1.

18. An isolated polynucleotide substantially corresponding to the nucleotide segment consisting essentially of the nucleic acid sequence encoding cellulose synthase C (SEQ ID No: 5) wherein said polynucleotide acid segment is capable of hybridizing to the polynucleotide of Sequence ID No: 5 under stringent conditions.

19. The polynucleotide of claim 18 substantially corresponding to nucleotides 5005 to 8961, as shown in FIG. 1.

20. An isolated, polynucleotide substantially corresponding to the nucleotide segment consisting essentially of the nucleic acid sequence encoding cellulose synthase D (SEQ ID No: 6) wherein said polynucleotide acid segment is capable of hybridizing to the polynucleotide of Sequence ID No: 6 under stringent conditions.

21. The polynucleotide of claim 20 substantially corresponding to nucleotides 8964 to 9431, as shown in FIG. 1.

22. The polynucleotide of claim 14 which is operatively linked to a control sequence for expression.

23. The polynucleotide of claim 16 which is operatively linked to a control sequence for expression.

24. The polynucleotide of claim 18 which is operatively linked to a control sequence for expression.

25. The polynucleotide of claim 20 which is operatively linked to a control sequence for expression.

26. A recombinant host cell transformed with the polynucleotide of claim 22.

27. A recombinant host cell transformed with the polynucleotide of claim 23.

28. A recombinant host cell transformed with the polynucleotide of claim 24.

29. A recombinant host cell transformed with the polynucleotide of claim 25.

30. A method for producing bacterial cellulose synthase comprising culturing the transformed cells of claim 12 under conditions suitable for the expression of bacterial cellulose synthase, and recovering the expressed bacterial cellulose synthase from the culture.

31. A method for producing bacterial cellulose synthase comprising culturing the transformed cell of claim 27 under conditions suitable for the expression of bacterial cellulose synthase, and recovering the expressed bacterial cellulose synthase from the culture.

32. A method for increasing cellulose production in a recombinant microorganism, which method comprises:
   a) transforming a strain of a cellulose producing species of bacteria with a vector comprising at least one gene derived from the cellulose synthase operon, selected from the group consisting of cellulose synthase genes B, C, D, taken singly, and mixtures of genes A, B, C, and D; and (b) culturing said transformed microorganism under conditions suitable for the production of cellulose; and (c) recovering the cellulose.

33. The method of claim 32 wherein said DNA comprises the four genes encoded by the cellulose synthase operon.

34. The method of claim 32 wherein said polynucleotide is operably linked to a control sequence for expression of said cellulose synthase operon.

35. The method of claim 34 wherein said control sequence comprises a heterologous promoter and optionally, an operator.

36. The method of claim 35 wherein said heterologous promoter is a regulated promoter.

37. The method of claim 36 wherein said regulated promoter is selected from the group consisting of $P_L$, lac and tac promoters.

38. The method of claim 37 wherein said regulated promoter is the tac promoter and the recombinant microorganism further comprises a polynucleotide encoding the lacI gene product.

39. The method of claim 36 wherein said regulated promoter is the $P_L$ promoter and the recombinant microorganism further comprises a polynucleotide encoding the cI gene product.

40. The method of claim 39 wherein said bacterial cell is an Acetobacter cell.

41. The method of claim 40 wherein said Acetobacter cell has a cellulose synthase positive phenotype.

42. The process of claim 40 wherein said Acetobacter cell has a cellulose synthase positive phenotype.

43. A recombinant DNA vector comprising:
a) a functional Acetobacter origin of replication-containing fragment of plasmid p824, and
b) one or more DNA segments that convey resistance to at least one antibiotic when transformed into a sensitive host cell that is susceptible to transformation, cell division and culture.

44. The recombinant DNA vector of claim 43 which further comprises a functional replicon of an E. coli plasmid.

45. The recombinant DNA vector of claim 43 which further comprises a nucleic acid sequence encoding the bacterial cellulose synthase operon which is operably linked to a control sequence for expression.

46. The recombinant DNA vector of claim 45 which is pUC18-824 FS1 or pUC18-824 FS6.

47. Recombinant bacterial host cells transformed with the recombinant DNA vector of claim 43.

48. The recombinant bacterial host cell of claim 47 which is an Acetobacter or Escherichia species.

49. An isolated protein having the amino acid sequence of an Acetobacter cellulose synthase B (SEQ ID No:2 residues 755-1556) and allelic variants thereof.

50. An isolated protein having the amino acid sequence of an Acetobacter cellulose synthase A (SEQ ID No:2 residue 1-754) and allelic variants thereof.

51. An isolated protein having the amino acid sequence of an Acetobacter cellulose synthase C (SEQ ID No:2 residues 1557-2875) and allelic variants thereof.

52. An isolated protein having the amino acid sequence of an Acetobacter cellulose synthase D (SEQ ID No:2 residues 2876-3031) and allelic variants thereof.

53. A method according to claim 36 wherein said vector comprises genes A and B.

* * * * *